US011439378B2

(12) United States Patent
Gianotti et al.

(10) Patent No.: US 11,439,378 B2
(45) Date of Patent: Sep. 13, 2022

(54) CLOSURE DEVICES AND METHODS

(71) Applicant: Abbott Vascular Inc., Santa Clara, CA (US)

(72) Inventors: Marc G. Gianotti, Wiesendangen (CH); Aaron M. Fortson, Fremont, CA (US)

(73) Assignee: ABBOTT CARDIOVASCULAR SYSTEMS, INC., Santa Clara, CA (US)

( * ) Notice: Subject to any disclaimer, the term of this patent is extended or adjusted under 35 U.S.C. 154(b) by 302 days.

(21) Appl. No.: 16/737,604

(22) Filed: Jan. 8, 2020

(65) Prior Publication Data
US 2020/0138424 A1    May 7, 2020

Related U.S. Application Data

(60) Continuation of application No. 15/344,978, filed on Nov. 7, 2016, now Pat. No. 10,537,313, which is a
(Continued)

(51) Int. Cl.
*A61B 17/00* (2006.01)
*A61B 17/04* (2006.01)

(52) U.S. Cl.
CPC .......... *A61B 17/0057* (2013.01); *A61B 17/04* (2013.01); *A61B 17/0401* (2013.01);
(Continued)

(58) Field of Classification Search
CPC . A61B 17/0057; A61B 17/04; A61B 17/0401; A61B 17/0469; A61B 17/0482;
(Continued)

(56) References Cited

U.S. PATENT DOCUMENTS

| 287,046 A | 10/1883 | Norton |
| 438,400 A | 10/1890 | Brennen |

(Continued)

FOREIGN PATENT DOCUMENTS

| AU | 2003297432 A1 | 7/2004 |
| CA | 233960 A | 9/1923 |

(Continued)

OTHER PUBLICATIONS

Office Action received for U.S. Appl. No. 12/684,470, dated Aug. 26, 2015.
(Continued)

*Primary Examiner* — Julian W Woo
(74) *Attorney, Agent, or Firm* — Workman Nydegger; Randy Shen

(57) ABSTRACT

A method for closing a puncture in tissue that includes advancing a guide member into proximity with the tissue, the guide member having a needle guide, positioning a distal end of the guide member with the needle guide toward the tissue to present an opening of the needle guide toward the tissue the needle guide cooperating with a suture securing device that is slidably coupled to the guide member and a suture attached to the suture securing device, deploying the suture securing device, the suture securing device comprising a body with an anchor point for the suture and features that allow the suture securing device to pierce the tissue and resist retraction through the tissue, and establishing tension in the suture to move the suture securing device toward another suture securing device to thereby close the puncture in the tissue.

16 Claims, 18 Drawing Sheets

Related U.S. Application Data division of application No. 13/112,618, filed on May 20, 2011, now Pat. No. 9,486,191, which is a continuation-in-part of application No. 12/684,470, filed on Jan. 8, 2010, now Pat. No. 9,414,820.

(60) Provisional application No. 61/143,751, filed on Jan. 9, 2009.

(52) U.S. Cl.
CPC ...... *A61B 17/0469* (2013.01); *A61B 17/0482* (2013.01); *A61B 17/0483* (2013.01); *A61B 17/0487* (2013.01); *A61B 2017/00619* (2013.01); *A61B 2017/00623* (2013.01); *A61B 2017/00659* (2013.01); *A61B 2017/00663* (2013.01); *A61B 2017/00867* (2013.01); *A61B 2017/0409* (2013.01); *A61B 2017/0437* (2013.01); *A61B 2017/0464* (2013.01); *A61B 2017/0472* (2013.01)

(58) Field of Classification Search
CPC ............ A61B 17/0483; A61B 17/0487; A61B 2017/00619; A61B 2017/00623; A61B 2017/00659; A61B 2017/00663; A61B 2017/0409

See application file for complete search history.

(56) References Cited

U.S. PATENT DOCUMENTS

| | | | |
|---|---|---|---|
| 556,082 | A | 3/1896 | Boeddinghaus |
| 1,088,393 | A | 2/1914 | Backus |
| 1,123,290 | A | 1/1915 | Von Herff |
| 1,242,139 | A | 10/1917 | Callahan |
| 1,331,401 | A | 2/1920 | Summers |
| 1,426,111 | A | 8/1922 | Sacker |
| 1,480,935 | A | 1/1924 | Gleason |
| 1,516,990 | A | 11/1924 | Silverman |
| 1,596,004 | A | 8/1926 | De Bengoa |
| 1,647,958 | A | 11/1927 | Ciarlante |
| 1,847,347 | A | 3/1932 | Maisto |
| 1,852,098 | A | 4/1932 | Anderson |
| 1,880,569 | A | 10/1932 | Weis |
| 2,075,508 | A | 3/1937 | Davidson |
| 2,087,074 | A | 7/1937 | Tucker |
| 2,108,206 | A | 2/1938 | Mecker |
| 2,210,061 | A | 8/1940 | Caminez |
| 2,254,620 | A | 9/1941 | Miller |
| 2,316,297 | A | 4/1943 | Southerland et al. |
| 2,371,978 | A | 3/1945 | Perham |
| 2,453,227 | A | 11/1948 | Janes |
| 2,583,625 | A | 1/1952 | Bergan |
| 2,610,631 | A | 9/1952 | Calicchio |
| 2,684,070 | A | 7/1954 | Kelsey |
| 2,755,699 | A | 7/1956 | Forster |
| 2,756,748 | A | 7/1956 | Ferguson |
| 2,910,067 | A | 10/1959 | White |
| 2,944,311 | A | 7/1960 | Schneckenberger |
| 2,951,482 | A | 9/1960 | Sullivan |
| 2,969,887 | A | 1/1961 | Darmstadt et al. |
| 3,014,483 | A | 12/1961 | McCarthy |
| 3,015,403 | A | 1/1962 | Fuller |
| 3,029,754 | A | 4/1962 | Doyle |
| 3,113,379 | A | 12/1963 | Frank |
| 3,120,230 | A | 2/1964 | Skold |
| 3,142,878 | A | 8/1964 | Santora |
| 3,209,754 | A | 10/1965 | Brown |
| 3,209,784 | A | 10/1965 | Schwartz |
| 3,348,595 | A | 10/1967 | Stevens, Jr. |
| 3,357,070 | A | 12/1967 | Soloan |
| 3,482,428 | A | 12/1969 | Kapitanov et al. |
| 3,494,533 | A | 2/1970 | Green et al. |
| 3,494,553 | A | 2/1970 | Nelson |
| 3,495,586 | A | 2/1970 | Eberhard |
| 3,510,923 | A | 5/1970 | Blake |
| 3,513,848 | A | 5/1970 | Winston et al. |
| 3,517,128 | A | 6/1970 | Hines |
| 3,523,351 | A | 8/1970 | Filia |
| 3,525,340 | A | 8/1970 | Gilbert |
| 3,557,794 | A | 1/1971 | Van Patten |
| 3,586,002 | A | 6/1971 | Wood |
| 3,604,425 | A | 9/1971 | Le Roy |
| 3,618,447 | A | 11/1971 | Goins |
| 3,664,345 | A | 5/1972 | Dabbs et al. |
| 3,677,243 | A | 7/1972 | Nerz |
| 3,682,180 | A | 8/1972 | McFarlane |
| 3,732,719 | A | 5/1973 | Pallotta |
| 3,750,650 | A | 8/1973 | Ruttgers |
| 3,753,438 | A | 8/1973 | Wood et al. |
| 3,757,629 | A | 9/1973 | Schneider |
| 3,799,172 | A | 3/1974 | Szpur |
| 3,805,337 | A | 4/1974 | Branstetter |
| 3,814,104 | A | 6/1974 | Irnich et al. |
| 3,823,719 | A | 7/1974 | Cummings |
| 3,828,791 | A | 8/1974 | Santos |
| 3,831,608 | A | 8/1974 | Kletschka et al. |
| 3,856,016 | A | 12/1974 | Davis |
| 3,874,388 | A | 4/1975 | King et al. |
| 3,908,662 | A | 9/1975 | Razgulov et al. |
| 3,926,194 | A | 12/1975 | Greenberg et al. |
| 3,931,821 | A | 1/1976 | Kletschka et al. |
| 3,939,820 | A | 2/1976 | Grayzel |
| 3,944,114 | A | 3/1976 | Coppens |
| 3,960,147 | A | 6/1976 | Murray |
| 3,976,079 | A | 8/1976 | Samuels et al. |
| 3,985,138 | A | 10/1976 | Jarvik |
| 4,007,743 | A | 2/1977 | Blake |
| 4,011,872 | A | 3/1977 | Komiya |
| 4,014,492 | A | 3/1977 | Rothfuss |
| 4,018,228 | A | 4/1977 | Goosen |
| 4,046,150 | A | 9/1977 | Schwartz et al. |
| 4,047,533 | A | 9/1977 | Perciaccante et al. |
| 4,064,881 | A | 12/1977 | Meredith |
| 4,112,944 | A | 9/1978 | Williams |
| 4,153,321 | A | 5/1979 | Pombrol |
| 4,162,673 | A | 7/1979 | Patel |
| 4,169,476 | A | 10/1979 | Hiltebrandt |
| 4,189,808 | A | 2/1980 | Brown |
| 4,192,315 | A | 3/1980 | Hilzinger et al. |
| 4,201,215 | A | 5/1980 | Crossett et al. |
| 4,204,541 | A | 5/1980 | Kapitanov |
| 4,207,870 | A | 6/1980 | Eldridge |
| 4,214,587 | A | 7/1980 | Sakura, Jr. |
| 4,215,699 | A | 8/1980 | Patel |
| 4,217,902 | A | 8/1980 | March |
| 4,267,995 | A | 5/1981 | McMillan |
| 4,273,129 | A | 6/1981 | Boebel |
| 4,274,415 | A | 6/1981 | Kanamoto et al. |
| 4,278,091 | A | 7/1981 | Borzone |
| 4,287,489 | A | 9/1981 | Pinkham |
| 4,291,698 | A | 9/1981 | Fuchs et al. |
| 4,317,445 | A | 3/1982 | Robinson |
| 4,317,451 | A | 3/1982 | Cerwin et al. |
| 4,318,401 | A | 3/1982 | Zimmerman |
| 4,327,485 | A | 5/1982 | Rix |
| 4,345,606 | A | 8/1982 | Littleford |
| 4,368,736 | A | 1/1983 | Kaster |
| 4,387,489 | A | 6/1983 | Dudek |
| 4,396,139 | A | 8/1983 | Hall et al. |
| 4,400,879 | A | 8/1983 | Hildreth |
| 4,407,286 | A | 10/1983 | Noiles et al. |
| 4,411,654 | A | 10/1983 | Boarini et al. |
| 4,412,832 | A | 11/1983 | Kling et al. |
| 4,428,376 | A | 1/1984 | Mericle |
| 4,440,170 | A | 4/1984 | Golden et al. |
| 4,449,531 | A | 5/1984 | Cerwin et al. |
| 4,475,544 | A | 10/1984 | Reis |
| 4,480,356 | A | 11/1984 | Martin |
| 4,485,816 | A | 12/1984 | Krumme |
| 4,501,276 | A | 2/1985 | Lombardi |
| RE31,855 | E | 3/1985 | Osborne et al. |
| 4,505,273 | A | 3/1985 | Braun et al. |

(56) References Cited

U.S. PATENT DOCUMENTS

| | | |
|---|---|---|
| 4,505,274 A | 3/1985 | Speelman |
| 4,523,591 A | 6/1985 | Kaplan et al. |
| 4,523,695 A | 6/1985 | Braun et al. |
| 4,525,157 A | 6/1985 | Vaillancourt |
| 4,526,174 A | 7/1985 | Froehlich |
| 4,570,633 A | 2/1986 | Golden |
| 4,577,635 A | 3/1986 | Meredith |
| 4,586,503 A | 5/1986 | Kirsch et al. |
| 4,592,498 A | 6/1986 | Braun et al. |
| 4,595,559 A | 6/1986 | Planchamp |
| 4,596,559 A | 6/1986 | Fleischhacker |
| 4,607,638 A | 8/1986 | Crainich |
| 4,610,251 A | 9/1986 | Kumar |
| 4,610,252 A | 9/1986 | Catalano |
| 4,635,634 A | 1/1987 | Santos |
| 4,635,637 A | 1/1987 | Schreiber |
| 4,644,956 A | 2/1987 | Morgenstern |
| 4,651,737 A | 3/1987 | Deniega |
| 4,664,305 A | 5/1987 | Blake et al. |
| 4,665,906 A | 5/1987 | Jervis |
| 4,667,675 A | 5/1987 | Davis |
| 4,683,895 A | 8/1987 | Pohndorf |
| 4,687,469 A | 8/1987 | Osypka |
| 4,693,249 A | 9/1987 | Schenck et al. |
| 4,697,312 A | 10/1987 | Freyer |
| 4,719,917 A | 1/1988 | Barrows et al. |
| 4,724,840 A | 2/1988 | McVay et al. |
| 4,738,658 A | 4/1988 | Magro et al. |
| 4,744,364 A | 5/1988 | Kensey |
| 4,747,407 A | 5/1988 | Liu et al. |
| 4,750,492 A | 6/1988 | Jacobs |
| 4,759,364 A | 7/1988 | Boebel |
| 4,771,782 A | 9/1988 | Millar |
| 4,772,266 A | 9/1988 | Groshong |
| 4,773,421 A | 9/1988 | Davis |
| 4,777,950 A | 10/1988 | Kees, Jr. |
| 4,789,090 A | 12/1988 | Blake, III |
| 4,813,586 A | 3/1989 | Seifert |
| 4,823,794 A | 4/1989 | Pierce |
| 4,830,002 A | 5/1989 | Semm |
| 4,832,688 A | 5/1989 | Sagae et al. |
| 4,836,204 A | 6/1989 | Landymore et al. |
| 4,852,568 A | 8/1989 | Kensey |
| 4,860,746 A | 8/1989 | Yoon |
| 4,865,026 A | 9/1989 | Barrett |
| 4,866,818 A | 9/1989 | Thompson |
| 4,874,122 A | 10/1989 | Froehlich et al. |
| 4,878,915 A | 11/1989 | Brantigan |
| 4,885,003 A | 12/1989 | Hillstead |
| 4,886,067 A | 12/1989 | Palermo |
| 4,887,601 A | 12/1989 | Richards |
| 4,890,612 A | 1/1990 | Kensey |
| 4,902,508 A | 2/1990 | Badylak et al. |
| 4,917,087 A | 4/1990 | Walsh et al. |
| 4,917,089 A | 4/1990 | Sideris |
| 4,929,240 A | 5/1990 | Kirsch et al. |
| 4,934,364 A | 6/1990 | Green |
| 4,950,258 A | 8/1990 | Kawai et al. |
| 4,957,499 A | 9/1990 | Lipatov et al. |
| 4,961,729 A | 10/1990 | Vaillancourt |
| 4,967,949 A | 11/1990 | Sandhaus |
| 4,976,721 A | 12/1990 | Blasnik et al. |
| 4,983,176 A | 1/1991 | Cushman et al. |
| 4,997,436 A | 3/1991 | Oberlander |
| 4,997,439 A | 3/1991 | Chen |
| 4,997,736 A | 3/1991 | Kawamura et al. |
| 5,002,562 A | 3/1991 | Oberlander |
| 5,007,921 A | 4/1991 | Brown |
| 5,009,663 A | 4/1991 | Broome |
| 5,011,487 A | 4/1991 | Shichman |
| 5,015,247 A | 5/1991 | Michelson |
| 5,021,059 A | 6/1991 | Kensey et al. |
| 5,026,390 A | 6/1991 | Brown |
| 5,030,226 A | 7/1991 | Green et al. |
| 5,032,127 A | 7/1991 | Frazee et al. |
| 5,035,692 A | 7/1991 | Lyon et al. |
| 5,041,129 A | 8/1991 | Hayhurst et al. |
| 5,042,707 A | 8/1991 | Taheri |
| 5,047,047 A | 9/1991 | Yoon |
| 5,053,008 A | 10/1991 | Bajaj |
| 5,059,201 A | 10/1991 | Asnis |
| 5,061,274 A | 10/1991 | Kensey |
| 5,061,283 A | 10/1991 | Silvestrini |
| 5,071,430 A | 12/1991 | De et al. |
| 5,074,871 A | 12/1991 | Groshong |
| 5,078,731 A | 1/1992 | Hayhurst |
| 5,092,941 A | 3/1992 | Miura |
| 5,100,418 A | 3/1992 | Yoon et al. |
| 5,100,422 A | 3/1992 | Berguer et al. |
| 5,108,420 A | 4/1992 | Marks |
| 5,108,421 A | 4/1992 | Fowler |
| 5,114,032 A | 5/1992 | Laidlaw |
| 5,114,065 A | 5/1992 | Storace |
| 5,116,349 A | 5/1992 | Aranyi |
| 5,122,122 A | 6/1992 | Allgood |
| 5,122,156 A | 6/1992 | Granger et al. |
| 5,131,379 A | 7/1992 | Sewell, Jr. |
| 5,141,520 A | 8/1992 | Goble et al. |
| 5,147,381 A | 9/1992 | Heimerl et al. |
| 5,156,609 A | 10/1992 | Nakao et al. |
| 5,158,566 A | 10/1992 | Francesco |
| 5,160,339 A | 11/1992 | Chen et al. |
| 5,163,343 A | 11/1992 | Gish |
| 5,167,634 A | 12/1992 | Corrigan et al. |
| 5,167,643 A | 12/1992 | Lynn |
| 5,171,249 A | 12/1992 | Stefanchik et al. |
| 5,171,250 A | 12/1992 | Yoon |
| 5,171,251 A | 12/1992 | Bregen et al. |
| 5,171,259 A | 12/1992 | Inoue |
| 5,176,648 A | 1/1993 | Holmes et al. |
| 5,176,682 A | 1/1993 | Chow |
| 5,176,691 A | 1/1993 | Pierce |
| 5,178,625 A | 1/1993 | Groshong |
| 5,192,287 A | 3/1993 | Fournier et al. |
| 5,192,288 A | 3/1993 | Thompson et al. |
| 5,192,300 A | 3/1993 | Fowler |
| 5,192,301 A | 3/1993 | Kamiya et al. |
| 5,192,302 A | 3/1993 | Kensey et al. |
| 5,192,602 A | 3/1993 | Spencer et al. |
| 5,193,533 A | 3/1993 | Body et al. |
| 5,197,971 A | 3/1993 | Bonutti |
| 5,203,787 A | 4/1993 | Noblitt et al. |
| 5,209,756 A | 5/1993 | Seedhom et al. |
| 5,211,651 A | 5/1993 | Reger et al. |
| 5,217,024 A | 6/1993 | Dorsey et al. |
| 5,217,471 A | 6/1993 | Burkhart |
| 5,219,359 A | 6/1993 | McQuilkin et al. |
| 5,222,971 A | 6/1993 | Willard et al. |
| 5,222,974 A | 6/1993 | Kensey et al. |
| 5,226,908 A | 7/1993 | Yoon |
| 5,234,449 A | 8/1993 | Bruker et al. |
| 5,236,435 A | 8/1993 | Sewell, Jr. |
| 5,236,445 A | 8/1993 | Hayhurst et al. |
| 5,237,996 A | 8/1993 | Waldman et al. |
| 5,242,456 A | 9/1993 | Nash et al. |
| 5,242,457 A | 9/1993 | Akopov et al. |
| 5,242,459 A | 9/1993 | Buelna |
| 5,243,857 A | 9/1993 | Janota |
| 5,246,156 A | 9/1993 | Rothfuss et al. |
| 5,246,443 A | 9/1993 | Mai |
| 5,250,058 A | 10/1993 | Miller et al. |
| 5,254,105 A | 10/1993 | Haaga |
| 5,255,679 A | 10/1993 | Imran |
| 5,258,015 A | 11/1993 | Li et al. |
| 5,269,792 A | 12/1993 | Kloeckl et al. |
| 5,275,610 A | 1/1994 | Eberbach |
| 5,275,616 A | 1/1994 | Fowler |
| 5,281,422 A | 1/1994 | Badylak et al. |
| 5,282,808 A | 2/1994 | Kovac et al. |
| 5,282,827 A | 2/1994 | Kensey et al. |
| 5,282,832 A | 2/1994 | Toso et al. |
| 5,284,488 A | 2/1994 | Sideris |
| 5,289,963 A | 3/1994 | McGarry et al. |
| 5,290,243 A | 3/1994 | Chodorow et al. |

(56) References Cited

U.S. PATENT DOCUMENTS

| | | |
|---|---|---|
| 5,290,310 A | 3/1994 | Makower et al. |
| 5,292,309 A | 3/1994 | Van et al. |
| 5,292,332 A | 3/1994 | Lee |
| 5,304,183 A | 4/1994 | Gourlay et al. |
| 5,304,184 A | 4/1994 | Hathaway et al. |
| 5,304,204 A | 4/1994 | Bregen |
| 5,306,254 A | 4/1994 | Nash et al. |
| 5,306,280 A | 4/1994 | Bregen et al. |
| 5,309,927 A | 5/1994 | Welch |
| 5,318,542 A | 6/1994 | Hirsch et al. |
| 5,320,639 A | 6/1994 | Rudnick |
| 5,322,694 A | 6/1994 | Sixsmith |
| 5,327,908 A | 7/1994 | Gerry |
| 5,328,472 A | 7/1994 | Steinke et al. |
| 5,330,442 A | 7/1994 | Green et al. |
| 5,330,445 A | 7/1994 | Haaga |
| 5,330,503 A | 7/1994 | Yoon |
| 5,334,216 A | 8/1994 | Vidal et al. |
| 5,334,217 A | 8/1994 | Das |
| 5,335,680 A | 8/1994 | Moore |
| 5,340,360 A | 8/1994 | Stefanchik |
| 5,342,393 A | 8/1994 | Stack |
| 5,344,439 A | 9/1994 | Otten |
| 5,350,399 A | 9/1994 | Erlebacher et al. |
| 5,352,229 A | 10/1994 | Goble et al. |
| 5,354,279 A | 10/1994 | Hofling |
| 5,364,406 A | 11/1994 | Sewell, Jr. |
| 5,364,408 A | 11/1994 | Gordon |
| 5,366,458 A | 11/1994 | Korthoff et al. |
| 5,366,479 A | 11/1994 | McGarry et al. |
| 5,376,101 A | 12/1994 | Green et al. |
| 5,383,896 A | 1/1995 | Gershony et al. |
| 5,383,897 A | 1/1995 | Wholey |
| 5,383,905 A | 1/1995 | Golds et al. |
| RE34,866 E | 2/1995 | Kensey et al. |
| 5,391,173 A | 2/1995 | Wilk |
| 5,391,174 A | 2/1995 | Weston |
| 5,392,978 A | 2/1995 | Velez et al. |
| 5,395,030 A | 3/1995 | Kuramoto et al. |
| 5,397,355 A | 3/1995 | Marin et al. |
| 5,403,330 A | 4/1995 | Tuason |
| 5,403,331 A | 4/1995 | Chesterfield et al. |
| 5,404,621 A | 4/1995 | Heinke |
| 5,409,499 A | 4/1995 | Yi |
| 5,411,520 A | 5/1995 | Nash et al. |
| 5,413,571 A | 5/1995 | Katsaros et al. |
| 5,413,584 A | 5/1995 | Schulze |
| 5,416,584 A | 5/1995 | Kay |
| 5,417,699 A | 5/1995 | Klein et al. |
| 5,419,765 A | 5/1995 | Weldon et al. |
| 5,419,777 A | 5/1995 | Hofling |
| 5,421,832 A | 6/1995 | Lefebvre |
| 5,423,857 A | 6/1995 | Rosenman et al. |
| 5,425,489 A | 6/1995 | Shichman et al. |
| 5,425,740 A | 6/1995 | Hutchinson, Jr. |
| 5,431,639 A | 7/1995 | Shaw |
| 5,431,667 A | 7/1995 | Thompson et al. |
| 5,433,721 A | 7/1995 | Hooven et al. |
| 5,437,631 A | 8/1995 | Janzen |
| 5,439,479 A | 8/1995 | Shichman et al. |
| 5,443,477 A | 8/1995 | Marin et al. |
| 5,443,481 A | 8/1995 | Lee |
| 5,445,167 A | 8/1995 | Yoon et al. |
| 5,449,359 A | 9/1995 | Groiso |
| 5,451,235 A | 9/1995 | Lock et al. |
| 5,454,413 A | 10/1995 | Morelli |
| 5,456,400 A | 10/1995 | Shichman et al. |
| 5,462,558 A | 10/1995 | Kolesa et al. |
| 5,462,561 A | 10/1995 | Voda |
| 5,464,413 A | 11/1995 | Siska et al. |
| 5,464,416 A | 11/1995 | Steckel |
| 5,466,241 A | 11/1995 | Leroy et al. |
| 5,470,010 A | 11/1995 | Rothfuss et al. |
| 5,471,982 A | 12/1995 | Edwards et al. |
| 5,474,557 A | 12/1995 | Mai |
| 5,474,569 A | 12/1995 | Zinreich et al. |
| 5,474,572 A | 12/1995 | Hayhurst |
| 5,476,505 A | 12/1995 | Limon |
| 5,478,352 A | 12/1995 | Fowler |
| 5,478,353 A | 12/1995 | Yoon |
| 5,478,354 A | 12/1995 | Tovey et al. |
| 5,478,853 A | 12/1995 | Regnier et al. |
| 5,484,420 A | 1/1996 | Russo |
| 5,486,195 A | 1/1996 | Myers et al. |
| 5,492,119 A | 2/1996 | Abrams |
| 5,496,332 A | 3/1996 | Sierra et al. |
| 5,497,933 A | 3/1996 | DeFonzo et al. |
| 5,501,698 A | 3/1996 | Roth et al. |
| 5,507,744 A | 4/1996 | Tay et al. |
| 5,507,755 A | 4/1996 | Gresl et al. |
| 5,510,115 A | 4/1996 | Breillatt et al. |
| 5,514,159 A | 5/1996 | Matula et al. |
| 5,521,184 A | 5/1996 | Zimmermann |
| 5,522,840 A | 6/1996 | Krajicek |
| 5,527,322 A | 6/1996 | Klein et al. |
| 5,536,251 A | 7/1996 | Evard et al. |
| 5,536,267 A | 7/1996 | Edwards et al. |
| 5,540,712 A | 7/1996 | Kleshinski et al. |
| 5,540,716 A | 7/1996 | Hlavacek |
| 5,543,520 A | 8/1996 | Zimmermann |
| 5,544,802 A | 8/1996 | Crainich |
| 5,545,178 A | 8/1996 | Kensey et al. |
| 5,547,474 A | 8/1996 | Kloeckl et al. |
| 5,560,532 A | 10/1996 | DeFonzo et al. |
| 5,562,684 A | 10/1996 | Kammerer |
| 5,571,120 A | 11/1996 | Yoon |
| 5,573,540 A | 11/1996 | Yoon |
| 5,573,784 A | 11/1996 | Badylak et al. |
| 5,575,771 A | 11/1996 | Walinsky |
| 5,582,616 A | 12/1996 | Bolduc et al. |
| 5,584,879 A | 12/1996 | Reimold et al. |
| 5,591,205 A | 1/1997 | Fowler |
| 5,593,412 A | 1/1997 | Martinez et al. |
| 5,593,422 A | 1/1997 | Muijs et al. |
| 5,593,425 A | 1/1997 | Bonutti et al. |
| 5,601,602 A | 2/1997 | Fowler |
| 5,609,597 A | 3/1997 | Lehrer |
| 5,611,986 A | 3/1997 | Datta et al. |
| 5,613,974 A | 3/1997 | Andreas et al. |
| 5,613,975 A | 3/1997 | Christy |
| 5,618,291 A | 4/1997 | Thompson et al. |
| 5,618,306 A | 4/1997 | Roth et al. |
| 5,620,452 A | 4/1997 | Yoon |
| 5,620,461 A | 4/1997 | Muijs et al. |
| 5,626,614 A | 5/1997 | Hart |
| 5,630,824 A | 5/1997 | Hart |
| 5,634,936 A | 6/1997 | Linden et al. |
| 5,643,318 A | 7/1997 | Tsukernik et al. |
| 5,645,553 A | 7/1997 | Kolesa et al. |
| 5,645,565 A | 7/1997 | Rudd et al. |
| 5,645,566 A | 7/1997 | Brenneman et al. |
| 5,645,567 A | 7/1997 | Crainich |
| 5,647,372 A | 7/1997 | Tovey et al. |
| 5,649,959 A | 7/1997 | Hannam et al. |
| D383,539 S | 9/1997 | Croley et al. |
| 5,669,917 A | 9/1997 | Sauer et al. |
| 5,669,935 A | 9/1997 | Rosenman et al. |
| 5,672,174 A | 9/1997 | Gough et al. |
| 5,674,231 A | 10/1997 | Green et al. |
| 5,674,244 A | 10/1997 | Mathys |
| 5,676,689 A | 10/1997 | Kensey et al. |
| 5,676,974 A | 10/1997 | Valdes et al. |
| 5,678,572 A | 10/1997 | Shaw et al. |
| 5,681,280 A | 10/1997 | Rusk et al. |
| 5,681,334 A | 10/1997 | Evans et al. |
| 5,681,351 A | 10/1997 | Jamiolkowski et al. |
| 5,683,405 A | 11/1997 | Yacoubian et al. |
| 5,690,674 A | 11/1997 | Diaz |
| 5,693,061 A | 12/1997 | Pierce et al. |
| 5,695,504 A | 12/1997 | Gifford et al. |
| 5,695,505 A | 12/1997 | Yoon |
| 5,695,524 A | 12/1997 | Kelley et al. |
| 5,697,943 A | 12/1997 | Sauer et al. |
| 5,700,270 A | 12/1997 | Peyser et al. |

(56) References Cited

U.S. PATENT DOCUMENTS

| | | | |
|---|---|---|---|
| 5,700,273 A | 12/1997 | Buelna et al. |
| 5,709,224 A | 1/1998 | Behl et al. |
| 5,709,708 A | 1/1998 | Thal |
| 5,713,899 A | 2/1998 | Marnay et al. |
| 5,715,987 A | 2/1998 | Kelley et al. |
| 5,716,375 A | 2/1998 | Fowler |
| 5,720,755 A | 2/1998 | Dakov |
| 5,720,765 A | 2/1998 | Thal |
| 5,725,498 A | 3/1998 | Janzen et al. |
| 5,725,552 A | 3/1998 | Kotula et al. |
| 5,725,554 A | 3/1998 | Simon et al. |
| 5,725,556 A | 3/1998 | Moser et al. |
| 5,728,109 A | 3/1998 | Schulze et al. |
| 5,728,110 A | 3/1998 | Vidal et al. |
| 5,728,114 A | 3/1998 | Evans et al. |
| 5,728,116 A | 3/1998 | Rosenman |
| 5,728,122 A | 3/1998 | Leschinsky et al. |
| 5,728,132 A | 3/1998 | Van et al. |
| 5,728,133 A | 3/1998 | Kontos |
| 5,728,143 A | 3/1998 | Gough et al. |
| 5,732,872 A | 3/1998 | Bolduc et al. |
| 5,735,736 A | 4/1998 | Volk |
| 5,735,873 A | 4/1998 | MacLean |
| 5,735,875 A | 4/1998 | Bonutti et al. |
| 5,735,877 A | 4/1998 | Pagedas |
| 5,746,753 A | 5/1998 | Sullivan et al. |
| 5,749,826 A | 5/1998 | Faulkner |
| 5,749,898 A | 5/1998 | Schulze et al. |
| 5,752,966 A | 5/1998 | Chang |
| 5,755,726 A | 5/1998 | Pratt et al. |
| 5,755,727 A | 5/1998 | Kontos |
| 5,755,778 A | 5/1998 | Kleshinski |
| 5,759,189 A | 6/1998 | Ferragamo et al. |
| 5,762,872 A | 6/1998 | Buehler et al. |
| 5,766,217 A | 6/1998 | Christy |
| 5,766,246 A | 6/1998 | Mulhauser et al. |
| 5,769,862 A | 6/1998 | Kammerer et al. |
| 5,769,870 A | 6/1998 | Salahieh et al. |
| 5,776,147 A | 7/1998 | Dolendo |
| 5,776,150 A | 7/1998 | Nolan et al. |
| 5,779,707 A | 7/1998 | Bertholet et al. |
| 5,780,807 A | 7/1998 | Saunders |
| 5,782,844 A | 7/1998 | Yoon et al. |
| 5,782,860 A | 7/1998 | Epstein et al. |
| 5,782,861 A | 7/1998 | Cragg et al. |
| 5,782,864 A | 7/1998 | Lizardi |
| 5,795,958 A | 8/1998 | Rao et al. |
| 5,797,928 A | 8/1998 | Kogasaka |
| 5,797,929 A | 8/1998 | Andreas et al. |
| 5,797,931 A | 8/1998 | Bito et al. |
| 5,797,933 A | 8/1998 | Snow et al. |
| 5,797,958 A | 8/1998 | Yoon |
| 5,797,960 A | 8/1998 | Stevens et al. |
| 5,810,776 A | 9/1998 | Bacich et al. |
| 5,810,846 A | 9/1998 | Virnich et al. |
| 5,810,851 A | 9/1998 | Yoon |
| 5,810,877 A | 9/1998 | Roth et al. |
| 5,814,069 A | 9/1998 | Schulze et al. |
| 5,817,113 A | 10/1998 | Gifford et al. |
| 5,820,631 A | 10/1998 | Nobles |
| 5,823,189 A | 10/1998 | Kordis |
| 5,827,298 A | 10/1998 | Hart et al. |
| 5,830,125 A | 11/1998 | Scribner et al. |
| 5,830,217 A | 11/1998 | Ryan |
| 5,830,221 A | 11/1998 | Stein et al. |
| 5,833,698 A | 11/1998 | Hinchliffe et al. |
| 5,843,164 A | 12/1998 | Frantzen et al. |
| 5,843,167 A | 12/1998 | Dwyer et al. |
| 5,845,657 A | 12/1998 | Carberry et al. |
| 5,846,254 A | 12/1998 | Schulze et al. |
| 5,853,421 A | 12/1998 | Leschinsky et al. |
| 5,853,422 A | 12/1998 | Huebsch et al. |
| 5,855,312 A | 1/1999 | Toledano |
| 5,855,576 A | 1/1999 | Leveen et al. |
| 5,858,082 A | 1/1999 | Cruz et al. |
| 5,860,991 A | 1/1999 | Klein et al. |
| 5,861,003 A | 1/1999 | Latson et al. |
| 5,861,005 A | 1/1999 | Kontos |
| 5,865,791 A | 2/1999 | Whayne et al. |
| 5,868,755 A | 2/1999 | Kanner et al. |
| 5,868,762 A * | 2/1999 | Cragg ............. A61B 17/0469 606/144 |
| 5,868,763 A | 2/1999 | Spence et al. |
| 5,871,474 A | 2/1999 | Hermann et al. |
| 5,871,490 A | 2/1999 | Schulze et al. |
| 5,871,501 A | 2/1999 | Leschinsky et al. |
| 5,871,525 A | 2/1999 | Edwards et al. |
| 5,873,876 A | 2/1999 | Christy |
| 5,873,891 A | 2/1999 | Sohn |
| 5,879,366 A | 3/1999 | Shaw et al. |
| 5,891,088 A | 4/1999 | Thompson et al. |
| 5,893,592 A | 4/1999 | Schulze et al. |
| 5,897,487 A | 4/1999 | Ouchi |
| 5,902,310 A | 5/1999 | Foerster et al. |
| 5,904,696 A | 5/1999 | Rosenman |
| 5,904,697 A | 5/1999 | Gifford et al. |
| 5,904,703 A | 5/1999 | Gilson |
| 5,906,631 A | 5/1999 | Imran |
| 5,907,893 A | 6/1999 | Zadno-Azizi et al. |
| 5,908,149 A | 6/1999 | Welch et al. |
| 5,910,155 A | 6/1999 | Ratcliff et al. |
| 5,919,207 A | 7/1999 | Taheri |
| 5,919,208 A | 7/1999 | Valenti |
| 5,922,009 A | 7/1999 | Epstein et al. |
| 5,928,208 A | 7/1999 | Chu et al. |
| 5,928,231 A | 7/1999 | Klein et al. |
| 5,928,251 A | 7/1999 | Aranyi et al. |
| 5,928,260 A | 7/1999 | Chin et al. |
| 5,935,147 A | 8/1999 | Kensey et al. |
| 5,938,667 A | 8/1999 | Peyser et al. |
| 5,941,890 A | 8/1999 | Voegele et al. |
| 5,947,999 A | 9/1999 | Groiso |
| 5,948,001 A | 9/1999 | Larsen |
| 5,951,518 A | 9/1999 | Licata et al. |
| 5,951,547 A | 9/1999 | Gough et al. |
| 5,951,575 A | 9/1999 | Bolduc et al. |
| 5,951,576 A | 9/1999 | Wakabayashi |
| 5,951,589 A | 9/1999 | Epstein et al. |
| 5,954,732 A | 9/1999 | Hart et al. |
| 5,957,900 A | 9/1999 | Ouchi |
| 5,957,936 A | 9/1999 | Yoon et al. |
| 5,957,938 A | 9/1999 | Zhu et al. |
| 5,957,940 A | 9/1999 | Tanner et al. |
| 5,964,782 A | 10/1999 | Lafontaine et al. |
| 5,972,023 A | 10/1999 | Tanner et al. |
| 5,976,159 A | 11/1999 | Bolduc et al. |
| 5,976,161 A | 11/1999 | Kirsch et al. |
| 5,976,174 A | 11/1999 | Ruiz |
| 5,980,517 A | 11/1999 | Gough |
| 5,984,934 A | 11/1999 | Ashby et al. |
| 5,984,948 A | 11/1999 | Hasson |
| 5,984,949 A | 11/1999 | Levin |
| 5,993,466 A | 11/1999 | Yoon |
| 5,993,468 A | 11/1999 | Rygaard |
| 5,993,476 A | 11/1999 | Groiso |
| 6,001,110 A | 12/1999 | Adams |
| 6,004,341 A | 12/1999 | Zhu et al. |
| 6,007,563 A | 12/1999 | Nash et al. |
| 6,007,574 A | 12/1999 | Pulnev et al. |
| 6,009,877 A | 1/2000 | Edwards |
| 6,010,517 A | 1/2000 | Baccaro |
| 6,013,084 A | 1/2000 | Ken et al. |
| 6,015,815 A | 1/2000 | Mollison |
| 6,019,779 A | 2/2000 | Thorud et al. |
| 6,022,372 A | 2/2000 | Kontos |
| 6,024,747 A | 2/2000 | Kontos |
| 6,024,750 A | 2/2000 | Mastri et al. |
| 6,024,756 A | 2/2000 | Huebsch et al. |
| 6,024,758 A | 2/2000 | Thal |
| 6,030,364 A | 2/2000 | Durgin et al. |
| 6,030,413 A | 2/2000 | Lazarus |
| 6,033,427 A | 3/2000 | Lee |
| 6,036,703 A | 3/2000 | Evans et al. |
| 6,036,720 A | 3/2000 | Abrams et al. |

(56) References Cited

U.S. PATENT DOCUMENTS

| | | | |
|---|---|---|---|
| 6,045,570 | A | 4/2000 | Epstein et al. |
| 6,048,358 | A | 4/2000 | Barak |
| 6,056,688 | A | 5/2000 | Benderev et al. |
| 6,056,744 | A | 5/2000 | Edwards |
| 6,056,768 | A | 5/2000 | Cates et al. |
| 6,056,769 | A | 5/2000 | Epstein et al. |
| 6,056,770 | A | 5/2000 | Epstein et al. |
| 6,059,800 | A | 5/2000 | Hart et al. |
| 6,059,825 | A | 5/2000 | Hobbs et al. |
| 6,063,085 | A | 5/2000 | Tay et al. |
| 6,063,114 | A | 5/2000 | Nash et al. |
| 6,066,160 | A | 5/2000 | Colvin et al. |
| 6,068,603 | A | 5/2000 | Suzuki |
| 6,071,300 | A | 6/2000 | Brenneman et al. |
| 6,074,395 | A | 6/2000 | Trott et al. |
| 6,074,409 | A | 6/2000 | Goldfarb |
| 6,077,281 | A | 6/2000 | Das |
| 6,077,291 | A | 6/2000 | Das |
| 6,080,182 | A | 6/2000 | Shaw et al. |
| 6,080,183 | A | 6/2000 | Tsugita et al. |
| 6,083,242 | A | 7/2000 | Cook |
| 6,086,608 | A | 7/2000 | Ek et al. |
| 6,090,130 | A | 7/2000 | Nash et al. |
| 6,092,561 | A | 7/2000 | Schmid |
| 6,095,155 | A | 8/2000 | Criscuolo |
| 6,099,553 | A | 8/2000 | Hart et al. |
| 6,102,271 | A | 8/2000 | Longo et al. |
| 6,105,217 | A | 8/2000 | Caradine et al. |
| 6,106,545 | A | 8/2000 | Egan |
| 6,110,184 | A | 8/2000 | Weadock |
| 6,113,610 | A | 9/2000 | Poncet |
| 6,113,611 | A | 9/2000 | Allen et al. |
| 6,113,612 | A | 9/2000 | Swanson et al. |
| 6,117,125 | A | 9/2000 | Rothbarth et al. |
| 6,117,144 | A | 9/2000 | Nobles et al. |
| 6,117,148 | A | 9/2000 | Ravo et al. |
| 6,117,157 | A | 9/2000 | Tekulve |
| 6,117,159 | A | 9/2000 | Huebsch et al. |
| 6,120,513 | A | 9/2000 | Bailey et al. |
| 6,120,524 | A | 9/2000 | Taheri |
| 6,126,675 | A | 10/2000 | Shchervinsky et al. |
| 6,126,677 | A | 10/2000 | Ganaja et al. |
| 6,136,010 | A | 10/2000 | Modesitt et al. |
| 6,143,004 | A | 11/2000 | Davis et al. |
| 6,143,017 | A | 11/2000 | Thal |
| 6,146,385 | A | 11/2000 | Torrie et al. |
| 6,149,660 | A | 11/2000 | Laufer et al. |
| 6,149,667 | A | 11/2000 | Hovland et al. |
| 6,152,144 | A | 11/2000 | Lesh et al. |
| 6,152,934 | A | 11/2000 | Harper et al. |
| 6,152,936 | A | 11/2000 | Christy et al. |
| 6,152,937 | A | 11/2000 | Peterson et al. |
| 6,159,234 | A | 12/2000 | Bonutti et al. |
| 6,161,263 | A | 12/2000 | Anderson |
| 6,165,204 | A | 12/2000 | Levinson et al. |
| 6,171,277 | B1 | 1/2001 | Ponzi |
| 6,171,329 | B1 | 1/2001 | Shaw et al. |
| 6,174,322 | B1 | 1/2001 | Schneidt |
| 6,174,324 | B1 | 1/2001 | Egan et al. |
| 6,179,849 | B1 | 1/2001 | Yencho et al. |
| 6,179,860 | B1 | 1/2001 | Fulton et al. |
| 6,183,775 | B1 | 2/2001 | Ventouras |
| 6,193,708 | B1 | 2/2001 | Ken et al. |
| 6,193,734 | B1 | 2/2001 | Bolduc et al. |
| 6,197,042 | B1 | 3/2001 | Ginn et al. |
| 6,198,974 | B1 | 3/2001 | Webster, Jr. |
| 6,200,329 | B1 | 3/2001 | Fung et al. |
| 6,200,330 | B1 | 3/2001 | Benderev et al. |
| 6,203,565 | B1 | 3/2001 | Bonutti et al. |
| 6,206,895 | B1 | 3/2001 | Levinson |
| 6,206,913 | B1 | 3/2001 | Yencho et al. |
| 6,206,931 | B1 | 3/2001 | Cook et al. |
| 6,210,407 | B1 | 4/2001 | Webster |
| 6,210,418 | B1 | 4/2001 | Storz et al. |
| 6,217,554 | B1 | 4/2001 | Green |
| 6,220,248 | B1 | 4/2001 | Voegele et al. |
| 6,221,084 | B1 | 4/2001 | Fleenor |
| 6,221,102 | B1 | 4/2001 | Baker et al. |
| 6,231,561 | B1 | 5/2001 | Frazier et al. |
| 6,231,592 | B1 | 5/2001 | Bonutti et al. |
| 6,238,705 | B1 | 5/2001 | Liu et al. |
| 6,241,740 | B1 | 6/2001 | Davis et al. |
| 6,245,079 | B1 | 6/2001 | Nobles et al. |
| 6,248,124 | B1 | 6/2001 | Pedros et al. |
| 6,254,615 | B1 | 7/2001 | Bolduc et al. |
| 6,254,617 | B1 | 7/2001 | Spence et al. |
| 6,254,642 | B1 | 7/2001 | Taylor |
| 6,258,115 | B1 | 7/2001 | Dubrul |
| 6,267,773 | B1 | 7/2001 | Gadberry et al. |
| 6,273,903 | B1 | 8/2001 | Wilk |
| 6,276,704 | B1 | 8/2001 | Suiter |
| 6,277,140 | B2 | 8/2001 | Ginn et al. |
| 6,280,460 | B1 | 8/2001 | Bolduc et al. |
| 6,287,322 | B1 | 9/2001 | Zhu et al. |
| 6,287,335 | B1 | 9/2001 | Drasler et al. |
| 6,290,674 | B1 | 9/2001 | Roue et al. |
| 6,296,657 | B1 | 10/2001 | Brucker |
| 6,302,870 | B1 | 10/2001 | Jacobsen et al. |
| 6,302,898 | B1 | 10/2001 | Edwards et al. |
| 6,305,891 | B1 | 10/2001 | Burlingame |
| 6,306,081 | B1 | 10/2001 | Ishikawa et al. |
| 6,309,416 | B1 | 10/2001 | Swanson et al. |
| 6,319,258 | B1 | 11/2001 | McAllen et al. |
| 6,322,580 | B1 | 11/2001 | Kanner |
| 6,328,727 | B1 | 12/2001 | Frazier et al. |
| 6,329,386 | B1 | 12/2001 | Mollison |
| 6,334,865 | B1 | 1/2002 | Redmond et al. |
| 6,348,064 | B1 | 2/2002 | Kanner |
| 6,355,052 | B1 | 3/2002 | Neuss et al. |
| 6,355,061 | B1 | 3/2002 | Quiachon et al. |
| 6,358,258 | B1 | 3/2002 | Arcia et al. |
| 6,375,671 | B1 | 4/2002 | Kobayashi et al. |
| D457,958 | S | 5/2002 | Dycus et al. |
| 6,383,208 | B1 | 5/2002 | Sancoff et al. |
| 6,391,048 | B1 | 5/2002 | Ginn et al. |
| 6,395,015 | B1 | 5/2002 | Borst et al. |
| 6,397,110 | B1 | 5/2002 | Kuzma |
| 6,398,752 | B1 | 6/2002 | Sweezer et al. |
| 6,402,765 | B1 | 6/2002 | Monassevitch et al. |
| 6,409,739 | B1 | 6/2002 | Nobles et al. |
| 6,419,669 | B1 | 7/2002 | Frazier et al. |
| 6,421,899 | B1 | 7/2002 | Zitnay |
| 6,423,054 | B1 | 7/2002 | Ouchi |
| 6,425,911 | B1 | 7/2002 | Akerfeldt et al. |
| 6,428,472 | B1 | 8/2002 | Haas |
| 6,428,548 | B1 | 8/2002 | Durgin et al. |
| 6,443,158 | B1 | 9/2002 | LaFontaine et al. |
| 6,443,963 | B1 | 9/2002 | Baldwin et al. |
| 6,447,540 | B1 | 9/2002 | Fontaine et al. |
| 6,450,391 | B1 | 9/2002 | Kayan et al. |
| 6,455,053 | B1 | 9/2002 | Okada et al. |
| 6,458,130 | B1 | 10/2002 | Frazier et al. |
| 6,461,327 | B1 | 10/2002 | Addis et al. |
| 6,461,364 | B1 | 10/2002 | Ginn et al. |
| 6,461,366 | B1 | 10/2002 | Seguin |
| 6,482,224 | B1 | 11/2002 | Michler et al. |
| 6,485,504 | B1 | 11/2002 | Johnson et al. |
| 6,488,692 | B1 | 12/2002 | Spence et al. |
| 6,500,115 | B2 | 12/2002 | Krattiger et al. |
| 6,505,210 | B1 | 1/2003 | Frey et al. |
| 6,506,210 | B1 | 1/2003 | Kanner |
| 6,508,828 | B1 | 1/2003 | Akerfeldt et al. |
| 6,514,280 | B1 | 2/2003 | Gilson |
| 6,517,498 | B1 | 2/2003 | Burbank et al. |
| 6,517,555 | B1 | 2/2003 | Caro |
| 6,517,569 | B2 | 2/2003 | Mikus et al. |
| 6,527,737 | B2 | 3/2003 | Kaneshige |
| 6,533,812 | B2 | 3/2003 | Swanson et al. |
| 6,544,230 | B1 | 4/2003 | Flaherty et al. |
| 6,547,806 | B1 | 4/2003 | Ding |
| 6,551,319 | B2 | 4/2003 | Lieberman |
| 6,558,349 | B1 | 5/2003 | Kirkman |
| 6,569,159 | B1 | 5/2003 | Edwards et al. |
| 6,569,173 | B1 | 5/2003 | Blatter et al. |

(56) References Cited

U.S. PATENT DOCUMENTS

| | | |
|---|---|---|
| 6,569,185 B2 | 5/2003 | Ungs |
| 6,572,629 B2 | 6/2003 | Kalloo et al. |
| 6,578,585 B1 | 6/2003 | Stachowski et al. |
| 6,582,452 B2 | 6/2003 | Coleman et al. |
| 6,582,482 B2 | 6/2003 | Gillman et al. |
| 6,596,012 B2 | 7/2003 | Akerfeldt et al. |
| 6,599,303 B1 | 7/2003 | Peterson et al. |
| 6,599,311 B1 | 7/2003 | Biggs et al. |
| 6,602,263 B1 | 8/2003 | Swanson et al. |
| 6,610,072 B1 | 8/2003 | Christy et al. |
| 6,613,059 B2 | 9/2003 | Schaller et al. |
| 6,613,060 B2 | 9/2003 | Adams et al. |
| 6,616,686 B2 | 9/2003 | Coleman et al. |
| 6,620,165 B2 | 9/2003 | Wellisz |
| 6,623,509 B2 | 9/2003 | Ginn |
| 6,623,510 B2 | 9/2003 | Carley et al. |
| 6,626,918 B1 | 9/2003 | Ginn et al. |
| 6,626,919 B1 | 9/2003 | Swanstrom |
| 6,626,920 B2 | 9/2003 | Whayne |
| 6,626,930 B1 | 9/2003 | Allen et al. |
| 6,632,197 B2 | 10/2003 | Lyon |
| 6,632,238 B2 | 10/2003 | Ginn et al. |
| 6,634,537 B2 | 10/2003 | Chen |
| 6,645,205 B2 | 11/2003 | Ginn |
| 6,645,225 B1 | 11/2003 | Atkinson |
| 6,645,255 B2 | 11/2003 | Sanduja et al. |
| 6,652,538 B2 | 11/2003 | Kayan et al. |
| 6,652,556 B1 | 11/2003 | Vantassel et al. |
| 6,663,633 B1 | 12/2003 | Pierson, III |
| 6,665,906 B2 | 12/2003 | Li |
| 6,669,714 B2 | 12/2003 | Coleman et al. |
| 6,673,083 B1 | 1/2004 | Kayan et al. |
| 6,676,665 B2 | 1/2004 | Foley et al. |
| 6,676,685 B2 | 1/2004 | Pedros et al. |
| 6,679,894 B2 | 1/2004 | Damarati |
| 6,685,707 B2 | 2/2004 | Roman et al. |
| 6,689,147 B1 | 2/2004 | Koster, Jr. |
| 6,695,867 B2 | 2/2004 | Ginn et al. |
| 6,699,256 B1 | 3/2004 | Logan et al. |
| 6,702,826 B2 | 3/2004 | Liddicoat et al. |
| 6,712,836 B1 | 3/2004 | Berg et al. |
| 6,712,837 B2 | 3/2004 | Aakerfeldt et al. |
| 6,719,777 B2 | 4/2004 | Ginn et al. |
| 6,726,704 B1 | 4/2004 | Loshakove et al. |
| 6,736,822 B2 | 5/2004 | McClellan et al. |
| 6,743,195 B2 | 6/2004 | Zucker |
| 6,743,243 B1 | 6/2004 | Roy et al. |
| 6,743,259 B2 | 6/2004 | Ginn |
| 6,745,079 B2 | 6/2004 | King |
| 6,746,457 B2 | 6/2004 | Dana et al. |
| 6,746,472 B2 | 6/2004 | Frazier et al. |
| 6,749,621 B2 | 6/2004 | Pantages et al. |
| 6,752,813 B2 | 6/2004 | Goldfarb et al. |
| 6,755,842 B2 | 6/2004 | Kanner et al. |
| 6,758,855 B2 | 7/2004 | Fulton et al. |
| 6,776,785 B1 | 8/2004 | Yencho et al. |
| 6,780,185 B2 | 8/2004 | Frei et al. |
| 6,780,197 B2 | 8/2004 | Roe et al. |
| 6,790,218 B2 | 9/2004 | Jayaraman |
| 6,790,220 B2 | 9/2004 | Morris et al. |
| 6,837,893 B2 | 1/2005 | Miller |
| 6,837,906 B2 | 1/2005 | Ginn |
| 6,846,319 B2 | 1/2005 | Ginn et al. |
| 6,849,078 B2 | 2/2005 | Durgin et al. |
| 6,860,895 B1 | 3/2005 | Akerfeldt et al. |
| 6,890,343 B2 | 5/2005 | Ginn et al. |
| 6,896,687 B2 | 5/2005 | Dakov |
| 6,896,692 B2 | 5/2005 | Ginn et al. |
| 6,904,647 B2 | 6/2005 | Byers, Jr. |
| 6,913,607 B2 | 7/2005 | Ainsworth et al. |
| 6,926,723 B1 | 8/2005 | Mulhauser et al. |
| 6,926,731 B2 | 8/2005 | Coleman et al. |
| 6,929,634 B2 | 8/2005 | Dorros et al. |
| 6,942,641 B2 | 9/2005 | Seddon |
| 6,942,674 B2 | 9/2005 | Belef et al. |
| 6,942,691 B1 | 9/2005 | Chuter |
| 6,969,391 B1 | 11/2005 | Gazzani |
| 6,969,397 B2 | 11/2005 | Ginn |
| 6,984,238 B2 | 1/2006 | Gifford et al. |
| 6,989,003 B2 | 1/2006 | Wing et al. |
| 7,001,398 B2 | 2/2006 | Carley et al. |
| 7,001,400 B2 | 2/2006 | Modesitt et al. |
| 7,008,435 B2 | 3/2006 | Cummins |
| 7,008,439 B1 | 3/2006 | Janzen et al. |
| 7,025,776 B1 | 4/2006 | Houser et al. |
| 7,048,747 B2 | 5/2006 | Arcia et al. |
| 7,060,084 B1 | 6/2006 | Loshakove et al. |
| 7,063,711 B1 | 6/2006 | Loshakove et al. |
| 7,076,305 B2 | 7/2006 | Imran et al. |
| 7,083,635 B2 | 8/2006 | Ginn |
| 7,087,064 B1 | 8/2006 | Hyde |
| 7,094,245 B2 | 8/2006 | Adams et al. |
| 7,108,709 B2 | 9/2006 | Cummins |
| 7,108,710 B2 | 9/2006 | Anderson |
| 7,111,768 B2 | 9/2006 | Cummins et al. |
| 7,112,225 B2 | 9/2006 | Ginn |
| 7,122,002 B2 | 10/2006 | Okada |
| 7,144,411 B2 | 12/2006 | Ginn et al. |
| 7,147,646 B2 | 12/2006 | Dana et al. |
| 7,163,551 B2 | 1/2007 | Anthony et al. |
| 7,169,158 B2 | 1/2007 | Sniffin et al. |
| 7,169,164 B2 | 1/2007 | Borillo et al. |
| 7,175,646 B2 | 2/2007 | Brenneman et al. |
| 7,211,101 B2 | 5/2007 | Carley et al. |
| 7,220,268 B2 | 5/2007 | Blatter |
| 7,261,716 B2 | 8/2007 | Strobel et al. |
| 7,270,672 B1 | 9/2007 | Singer |
| 7,306,614 B2 | 12/2007 | Weller et al. |
| 7,311,720 B2 | 12/2007 | Mueller et al. |
| 7,316,704 B2 | 1/2008 | Bagaoisan et al. |
| 7,316,706 B2 | 1/2008 | Bloom et al. |
| 7,322,995 B2 | 1/2008 | Buckman et al. |
| 7,331,979 B2 | 2/2008 | Khosravi et al. |
| 7,335,220 B2 | 2/2008 | Khosravi et al. |
| D566,272 S | 4/2008 | Walburg et al. |
| 7,361,178 B2 | 4/2008 | Hearn et al. |
| 7,361,183 B2 | 4/2008 | Ginn |
| 7,361,185 B2 | 4/2008 | O'Malley et al. |
| 7,393,363 B2 | 7/2008 | Ginn |
| 7,396,359 B1 | 7/2008 | Derowe et al. |
| 7,431,727 B2 | 10/2008 | Cole et al. |
| 7,445,596 B2 | 11/2008 | Kucklick et al. |
| 7,452,327 B2 | 11/2008 | Durgin et al. |
| 7,462,188 B2 | 12/2008 | McIntosh |
| 7,465,286 B2 | 12/2008 | Patterson et al. |
| 7,507,200 B2 | 3/2009 | Okada |
| 7,533,790 B1 | 5/2009 | Knodel et al. |
| 7,582,103 B2 | 9/2009 | Young et al. |
| 7,582,104 B2 | 9/2009 | Corcoran et al. |
| 7,618,427 B2 | 11/2009 | Ortiz et al. |
| 7,622,628 B2 | 11/2009 | Bergin et al. |
| 7,632,287 B2 * | 12/2009 | Baker .................. A61B 17/068 606/151 |
| 7,645,285 B2 | 1/2010 | Cosgrove et al. |
| D611,144 S | 3/2010 | Reynolds et al. |
| 7,678,135 B2 | 3/2010 | Maahs et al. |
| 7,727,249 B2 | 6/2010 | Rahmani |
| 7,731,655 B2 | 6/2010 | Smith et al. |
| 7,749,249 B2 | 7/2010 | Gelbart et al. |
| 7,780,696 B2 | 8/2010 | Daniel et al. |
| 7,799,042 B2 | 9/2010 | Williamson et al. |
| 7,806,904 B2 | 10/2010 | Carley et al. |
| 7,819,895 B2 | 10/2010 | Ginn et al. |
| 7,824,419 B2 | 11/2010 | Boraiah |
| 7,842,068 B2 | 11/2010 | Ginn |
| 7,854,810 B2 | 12/2010 | Carley et al. |
| 7,857,828 B2 | 12/2010 | Jabba et al. |
| 7,867,249 B2 | 1/2011 | Palermo et al. |
| 7,875,054 B2 | 1/2011 | LaFontaine |
| 7,879,071 B2 | 2/2011 | Carley et al. |
| 7,887,555 B2 | 2/2011 | Carley et al. |
| 7,887,563 B2 | 2/2011 | Cummins |
| 7,901,428 B2 | 3/2011 | Ginn et al. |
| 7,905,900 B2 | 3/2011 | Palermo et al. |

(56) References Cited

U.S. PATENT DOCUMENTS

| | | |
|---|---|---|
| 7,918,873 B2 | 4/2011 | Cummins |
| 7,931,669 B2 | 4/2011 | Ginn et al. |
| 7,967,842 B2 | 6/2011 | Bakos |
| 8,038,688 B2 | 10/2011 | Modesitt et al. |
| 8,103,327 B2 | 1/2012 | Harlev et al. |
| 8,105,352 B2 | 1/2012 | Egneloev |
| 8,128,644 B2 | 3/2012 | Carley et al. |
| 8,172,749 B2 | 5/2012 | Melsheimer |
| 8,216,260 B2 | 7/2012 | Lam et al. |
| 8,226,666 B2 | 7/2012 | Zarbatany et al. |
| 8,236,026 B2 | 8/2012 | Carley et al. |
| 8,403,929 B2 | 3/2013 | Weisshaupt et al. |
| 8,409,228 B2 | 4/2013 | Blatter et al. |
| 8,475,468 B2 | 7/2013 | Leckrone et al. |
| 8,486,108 B2 | 7/2013 | Carley et al. |
| 8,491,609 B2 | 7/2013 | Stone |
| 8,562,630 B2 | 10/2013 | Campbell |
| 8,579,932 B2 | 11/2013 | Pantages et al. |
| 8,579,933 B2 | 11/2013 | Chen et al. |
| 8,590,760 B2 | 11/2013 | Cummins et al. |
| 8,758,396 B2 | 6/2014 | Ginn et al. |
| 8,784,447 B2 | 7/2014 | Coleman et al. |
| 8,834,494 B2 | 9/2014 | Schorr et al. |
| 8,992,549 B2 | 3/2015 | Bennett, III |
| 9,345,460 B2 | 5/2016 | Houser et al. |
| 9,579,091 B2 | 2/2017 | Ginn et al. |
| 2001/0007077 A1 | 7/2001 | Ginn et al. |
| 2001/0021855 A1 | 9/2001 | Levinson |
| 2001/0031972 A1 | 10/2001 | Robertson et al. |
| 2001/0031973 A1 | 10/2001 | Nobles et al. |
| 2001/0044639 A1 | 11/2001 | Levinson |
| 2001/0046518 A1 | 11/2001 | Sawhney |
| 2001/0047180 A1 | 11/2001 | Grudem et al. |
| 2001/0053909 A1 | 12/2001 | Nakada et al. |
| 2002/0022822 A1 | 2/2002 | Cragg et al. |
| 2002/0026208 A1 | 2/2002 | Roe et al. |
| 2002/0026215 A1 | 2/2002 | Redmond et al. |
| 2002/0026216 A1 | 2/2002 | Grimes |
| 2002/0029050 A1 | 3/2002 | Gifford et al. |
| 2002/0038127 A1 | 3/2002 | Blatter et al. |
| 2002/0042622 A1 | 4/2002 | Vargas et al. |
| 2002/0045908 A1 | 4/2002 | Nobles et al. |
| 2002/0049427 A1 | 4/2002 | Wiener et al. |
| 2002/0049453 A1 | 4/2002 | Nobles et al. |
| 2002/0049472 A1 | 4/2002 | Coleman et al. |
| 2002/0056460 A1 | 5/2002 | Boyd et al. |
| 2002/0058960 A1 | 5/2002 | Hudson et al. |
| 2002/0062104 A1 | 5/2002 | Ashby et al. |
| 2002/0077657 A1 | 6/2002 | Ginn et al. |
| 2002/0082641 A1 | 6/2002 | Ginn et al. |
| 2002/0095164 A1 | 7/2002 | Andreas et al. |
| 2002/0095181 A1 | 7/2002 | Beyar |
| 2002/0099389 A1 | 7/2002 | Michler et al. |
| 2002/0106409 A1 | 8/2002 | Sawhney et al. |
| 2002/0107542 A1 | 8/2002 | Kanner et al. |
| 2002/0151921 A1 | 10/2002 | Kanner et al. |
| 2002/0151963 A1 | 10/2002 | Brown et al. |
| 2002/0169475 A1 | 11/2002 | Gainor et al. |
| 2002/0183786 A1 | 12/2002 | Girton |
| 2002/0183787 A1 | 12/2002 | Wahr et al. |
| 2002/0188275 A1 | 12/2002 | McGuckin |
| 2002/0188318 A1 | 12/2002 | Carley et al. |
| 2002/0193808 A1 | 12/2002 | Belef et al. |
| 2002/0198562 A1 | 12/2002 | Akerfeldt et al. |
| 2002/0198589 A1 | 12/2002 | Leong |
| 2003/0004543 A1 | 1/2003 | Gleeson et al. |
| 2003/0009180 A1 | 1/2003 | Hinchliffe et al. |
| 2003/0009196 A1 | 1/2003 | Peterson |
| 2003/0018358 A1 | 1/2003 | Saadat |
| 2003/0018377 A1 | 1/2003 | Berg et al. |
| 2003/0023248 A1 | 1/2003 | Parodi |
| 2003/0032981 A1 | 2/2003 | Kanner et al. |
| 2003/0033006 A1 | 2/2003 | Phillips et al. |
| 2003/0045893 A1 | 3/2003 | Ginn |
| 2003/0055455 A1 | 3/2003 | Yang et al. |
| 2003/0060846 A1 | 3/2003 | Egnelov et al. |
| 2003/0065358 A1 | 4/2003 | Frecker et al. |
| 2003/0083679 A1 | 5/2003 | Grudem et al. |
| 2003/0088269 A1 | 5/2003 | Ashby |
| 2003/0093093 A1 | 5/2003 | Modesitt et al. |
| 2003/0093096 A1 | 5/2003 | McGuckin et al. |
| 2003/0093108 A1 | 5/2003 | Avellanet et al. |
| 2003/0097140 A1 | 5/2003 | Kanner |
| 2003/0109890 A1 | 6/2003 | Kanner et al. |
| 2003/0125766 A1 | 7/2003 | Ding |
| 2003/0139819 A1 | 7/2003 | Beer et al. |
| 2003/0144695 A1 | 7/2003 | McGuckin et al. |
| 2003/0158577 A1 | 8/2003 | Ginn et al. |
| 2003/0158578 A1 | 8/2003 | Pantages et al. |
| 2003/0167063 A1 | 9/2003 | Kerr |
| 2003/0195504 A1 | 10/2003 | Tallarida et al. |
| 2003/0208211 A1 | 11/2003 | Kortenbach |
| 2003/0233095 A1 | 12/2003 | Urbanski et al. |
| 2004/0002763 A1 | 1/2004 | Phillips et al. |
| 2004/0009205 A1 | 1/2004 | Sawhney |
| 2004/0010285 A1 | 1/2004 | Carley et al. |
| 2004/0039414 A1 | 2/2004 | Carley et al. |
| 2004/0044350 A1 | 3/2004 | Martin et al. |
| 2004/0049224 A1 | 3/2004 | Buehlmann et al. |
| 2004/0059376 A1 | 3/2004 | Breuniger |
| 2004/0068273 A1 | 4/2004 | Fariss et al. |
| 2004/0073242 A1 | 4/2004 | Chanduszko |
| 2004/0073255 A1 | 4/2004 | Ginn et al. |
| 2004/0078053 A1 | 4/2004 | Berg et al. |
| 2004/0082906 A1 | 4/2004 | Tallarida et al. |
| 2004/0087985 A1 | 5/2004 | Loshakove et al. |
| 2004/0092962 A1 | 5/2004 | Thornton et al. |
| 2004/0092964 A1 | 5/2004 | Modesitt et al. |
| 2004/0092968 A1 | 5/2004 | Caro et al. |
| 2004/0092973 A1 | 5/2004 | Chanduszko et al. |
| 2004/0093024 A1 | 5/2004 | Lousararian et al. |
| 2004/0093027 A1 | 5/2004 | Fabisiak et al. |
| 2004/0097978 A1 | 5/2004 | Modesitt et al. |
| 2004/0106980 A1 | 6/2004 | Solovay et al. |
| 2004/0127940 A1 | 7/2004 | Ginn et al. |
| 2004/0143261 A1 | 7/2004 | Hartley et al. |
| 2004/0143290 A1 | 7/2004 | Brightbill |
| 2004/0143291 A1 | 7/2004 | Corcoran et al. |
| 2004/0147957 A1 | 7/2004 | Pierson |
| 2004/0153123 A1 | 8/2004 | Palermo et al. |
| 2004/0158127 A1 | 8/2004 | Okada |
| 2004/0158287 A1 | 8/2004 | Cragg et al. |
| 2004/0158309 A1 | 8/2004 | Wachter et al. |
| 2004/0167511 A1 | 8/2004 | Buehlmann et al. |
| 2004/0191277 A1 | 9/2004 | Sawhney et al. |
| 2004/0215232 A1 | 10/2004 | Belhe et al. |
| 2004/0225301 A1 | 11/2004 | Roop et al. |
| 2004/0243216 A1 | 12/2004 | Gregorich |
| 2004/0249412 A1 | 12/2004 | Snow et al. |
| 2004/0254591 A1 | 12/2004 | Kanner et al. |
| 2004/0267193 A1 | 12/2004 | Bagaoisan et al. |
| 2004/0267308 A1 | 12/2004 | Bagaoisan et al. |
| 2004/0267312 A1 | 12/2004 | Kanner et al. |
| 2005/0033326 A1 | 2/2005 | Briganti et al. |
| 2005/0038460 A1 | 2/2005 | Jayaraman |
| 2005/0038500 A1 | 2/2005 | Boylan et al. |
| 2005/0059982 A1 | 3/2005 | Zung et al. |
| 2005/0075654 A1 | 4/2005 | Kelleher |
| 2005/0075665 A1 | 4/2005 | Brenzel et al. |
| 2005/0085851 A1 | 4/2005 | Fiehler et al. |
| 2005/0085854 A1 | 4/2005 | Ginn |
| 2005/0085855 A1 | 4/2005 | Forsberg |
| 2005/0090859 A1 | 4/2005 | Ravlkumar |
| 2005/0119695 A1 | 6/2005 | Carley et al. |
| 2005/0121042 A1 | 6/2005 | Belhe et al. |
| 2005/0148818 A1 | 7/2005 | Mesallum |
| 2005/0149066 A1 | 7/2005 | Stafford |
| 2005/0149117 A1 | 7/2005 | Khosravi et al. |
| 2005/0152949 A1 | 7/2005 | Hotchkiss et al. |
| 2005/0154401 A1 | 7/2005 | Weldon et al. |
| 2005/0165357 A1 | 7/2005 | McGuckin et al. |
| 2005/0169974 A1 | 8/2005 | Tenerz et al. |
| 2005/0177189 A1 | 8/2005 | Ginn et al. |
| 2005/0187564 A1 | 8/2005 | Jayaraman |

(56) References Cited

U.S. PATENT DOCUMENTS

| | | |
|---|---|---|
| 2005/0203552 A1 | 9/2005 | Laufer et al. |
| 2005/0222614 A1 | 10/2005 | Ginn et al. |
| 2005/0228405 A1 | 10/2005 | Maruyama et al. |
| 2005/0228443 A1 | 10/2005 | Yassinzadeh |
| 2005/0234508 A1 | 10/2005 | Cummins et al. |
| 2005/0245876 A1 | 11/2005 | Khosravi et al. |
| 2005/0251202 A1 | 11/2005 | Ewers et al. |
| 2005/0256532 A1 | 11/2005 | Nayak et al. |
| 2005/0267495 A1 | 12/2005 | Ginn et al. |
| 2005/0267524 A1 | 12/2005 | Chanduszko |
| 2005/0267528 A1 | 12/2005 | Ginn et al. |
| 2005/0273136 A1 | 12/2005 | Belef et al. |
| 2005/0273137 A1 | 12/2005 | Ginn |
| 2005/0283188 A1 | 12/2005 | Loshakove et al. |
| 2006/0030867 A1 | 2/2006 | Zadno |
| 2006/0030868 A1 | 2/2006 | Bennett, III |
| 2006/0034930 A1 | 2/2006 | Khosravi et al. |
| 2006/0047313 A1 | 3/2006 | Khanna et al. |
| 2006/0058844 A1 | 3/2006 | White et al. |
| 2006/0064115 A1 | 3/2006 | Allen et al. |
| 2006/0069397 A1 | 3/2006 | Nobles et al. |
| 2006/0089635 A1 | 4/2006 | Young et al. |
| 2006/0095029 A1 | 5/2006 | Young et al. |
| 2006/0100664 A1 | 5/2006 | Pai et al. |
| 2006/0106418 A1 | 5/2006 | Seibold et al. |
| 2006/0142784 A1 | 6/2006 | Kontos |
| 2006/0162509 A1 | 7/2006 | Wang |
| 2006/0190014 A1 | 8/2006 | Ginn et al. |
| 2006/0190036 A1 | 8/2006 | Wendel et al. |
| 2006/0190037 A1 | 8/2006 | Ginn et al. |
| 2006/0195123 A1 | 8/2006 | Ginn et al. |
| 2006/0195125 A1 | 8/2006 | Sakakine et al. |
| 2006/0206146 A1 | 9/2006 | Tenerz |
| 2006/0217744 A1 | 9/2006 | Bender et al. |
| 2006/0229553 A1 | 10/2006 | Hammack et al. |
| 2006/0253037 A1 | 11/2006 | Ginn et al. |
| 2006/0253072 A1 | 11/2006 | Pai et al. |
| 2006/0259049 A1 | 11/2006 | Harada et al. |
| 2006/0265012 A1 | 11/2006 | Anderson |
| 2006/0287673 A1 | 12/2006 | Brett et al. |
| 2006/0293698 A1 | 12/2006 | Douk |
| 2007/0005093 A1 | 1/2007 | Cox |
| 2007/0010851 A1 | 1/2007 | Chanduszko et al. |
| 2007/0010853 A1 | 1/2007 | Ginn et al. |
| 2007/0021778 A1 | 1/2007 | Carly |
| 2007/0027476 A1 | 2/2007 | Harris et al. |
| 2007/0027525 A1 | 2/2007 | Ben-Muvhar |
| 2007/0049668 A1 | 3/2007 | Garner |
| 2007/0049967 A1 | 3/2007 | Sibbitt et al. |
| 2007/0049968 A1 | 3/2007 | Sibbitt et al. |
| 2007/0049970 A1 | 3/2007 | Belef et al. |
| 2007/0060858 A1 | 3/2007 | Sogard et al. |
| 2007/0060895 A1 | 3/2007 | Sibbitt et al. |
| 2007/0060950 A1 | 3/2007 | Khosravi et al. |
| 2007/0060951 A1 | 3/2007 | Shannon |
| 2007/0073337 A1 | 3/2007 | Abbott et al. |
| 2007/0078302 A1 | 4/2007 | Ortiz et al. |
| 2007/0083230 A1 | 4/2007 | Javois |
| 2007/0083231 A1 | 4/2007 | Lee |
| 2007/0093869 A1 | 4/2007 | Bloom et al. |
| 2007/0112304 A1 | 5/2007 | Voss |
| 2007/0112365 A1 | 5/2007 | Hilal et al. |
| 2007/0112385 A1 | 5/2007 | Conlon |
| 2007/0123816 A1 | 5/2007 | Zhu et al. |
| 2007/0123817 A1 | 5/2007 | Khosravi et al. |
| 2007/0123936 A1 | 5/2007 | Goldin et al. |
| 2007/0149996 A1 | 6/2007 | Coughlin |
| 2007/0167981 A1 | 7/2007 | Opolski et al. |
| 2007/0172430 A1 | 7/2007 | Brito et al. |
| 2007/0179527 A1 | 8/2007 | Eskuri et al. |
| 2007/0185529 A1 | 8/2007 | Coleman et al. |
| 2007/0185530 A1 | 8/2007 | Chin-Chen et al. |
| 2007/0203506 A1 | 8/2007 | Sibbitt et al. |
| 2007/0203507 A1 | 8/2007 | McLaughlin et al. |
| 2007/0208376 A1 | 9/2007 | Meng |
| 2007/0213747 A1 | 9/2007 | Monassevitch et al. |
| 2007/0225755 A1 | 9/2007 | Preinitz et al. |
| 2007/0225756 A1 | 9/2007 | Preinitz et al. |
| 2007/0225757 A1 | 9/2007 | Preinitz et al. |
| 2007/0225758 A1 | 9/2007 | Preinitz et al. |
| 2007/0239209 A1 | 10/2007 | Fallman |
| 2007/0250080 A1 | 10/2007 | Jones et al. |
| 2007/0265658 A1 | 11/2007 | Nelson et al. |
| 2007/0270904 A1 | 11/2007 | Ginn |
| 2007/0275036 A1 | 11/2007 | Green et al. |
| 2007/0276416 A1 | 11/2007 | Ginn et al. |
| 2007/0276488 A1 | 11/2007 | Wachter et al. |
| 2007/0282352 A1 | 12/2007 | Carley et al. |
| 2007/0282354 A1 | 12/2007 | McIntosh |
| 2007/0282373 A1 | 12/2007 | Ashby et al. |
| 2008/0004636 A1 | 1/2008 | Walberg et al. |
| 2008/0004640 A1 | 1/2008 | Ellingwood |
| 2008/0009794 A1 | 1/2008 | Bagaoisan et al. |
| 2008/0033459 A1 | 2/2008 | Shafi et al. |
| 2008/0045979 A1 | 2/2008 | Ma |
| 2008/0058839 A1 | 3/2008 | Nobles et al. |
| 2008/0065151 A1 | 3/2008 | Ginn |
| 2008/0065152 A1 | 3/2008 | Carley |
| 2008/0082123 A1 | 4/2008 | Forsberg et al. |
| 2008/0086075 A1 | 4/2008 | Isik et al. |
| 2008/0091235 A1 | 4/2008 | Sirota |
| 2008/0093414 A1 | 4/2008 | Bender et al. |
| 2008/0097509 A1 | 4/2008 | Beyar et al. |
| 2008/0114378 A1 | 5/2008 | Matsushita |
| 2008/0114395 A1 | 5/2008 | Mathisen et al. |
| 2008/0177288 A1 | 7/2008 | Carlson |
| 2008/0208225 A1 | 8/2008 | Seibold et al. |
| 2008/0210737 A1 | 9/2008 | Ginn et al. |
| 2008/0215089 A1 | 9/2008 | Williams et al. |
| 2008/0215090 A1 | 9/2008 | Gonzales et al. |
| 2008/0221616 A1 | 9/2008 | Ginn et al. |
| 2008/0243148 A1 | 10/2008 | Mikkaichi et al. |
| 2008/0243182 A1 | 10/2008 | Bates et al. |
| 2008/0249504 A1 | 10/2008 | Lattouf et al. |
| 2008/0262541 A1 | 10/2008 | Sater et al. |
| 2008/0269801 A1 | 10/2008 | Coleman et al. |
| 2008/0269802 A1 | 10/2008 | Coleman et al. |
| 2008/0272173 A1 | 11/2008 | Coleman et al. |
| 2008/0287967 A1 | 11/2008 | Andreas et al. |
| 2008/0287988 A1 | 11/2008 | Smith et al. |
| 2008/0294001 A1 | 11/2008 | Surti |
| 2008/0300628 A1 | 12/2008 | Ellingwood |
| 2008/0312666 A1 | 12/2008 | Ellingwood et al. |
| 2008/0312667 A1 | 12/2008 | Drasler et al. |
| 2008/0312686 A1 | 12/2008 | Ellingwood |
| 2008/0312740 A1 | 12/2008 | Wachter et al. |
| 2008/0319458 A1 | 12/2008 | Reynolds |
| 2008/0319475 A1 | 12/2008 | Clark et al. |
| 2009/0054912 A1 | 2/2009 | Heanue et al. |
| 2009/0062846 A1 | 3/2009 | Ken |
| 2009/0105728 A1 | 4/2009 | Noda et al. |
| 2009/0112306 A1 | 4/2009 | Bonsignore et al. |
| 2009/0132031 A1 | 5/2009 | Cook et al. |
| 2009/0137900 A1 | 5/2009 | Bonner et al. |
| 2009/0157101 A1 | 6/2009 | Reyes et al. |
| 2009/0157102 A1 | 6/2009 | Reynolds et al. |
| 2009/0157103 A1 | 6/2009 | Walberg et al. |
| 2009/0171388 A1 | 7/2009 | Dave et al. |
| 2009/0177212 A1 | 7/2009 | Carley et al. |
| 2009/0177213 A1 | 7/2009 | Carley et al. |
| 2009/0187215 A1 | 7/2009 | Mackiewicz et al. |
| 2009/0216267 A1 | 8/2009 | Willard et al. |
| 2009/0221960 A1 | 9/2009 | Albrecht et al. |
| 2009/0227938 A1 | 9/2009 | Fasching et al. |
| 2009/0230168 A1 | 9/2009 | Coleman et al. |
| 2009/0254119 A1 | 10/2009 | Sibbitt et al. |
| 2009/0259233 A1 | 10/2009 | Bogart et al. |
| 2009/0281555 A1 | 11/2009 | Stone |
| 2009/0287244 A1 | 11/2009 | Kokish |
| 2009/0312789 A1 | 12/2009 | Kassab et al. |
| 2010/0042118 A1 | 2/2010 | Garrison et al. |
| 2010/0042144 A1 | 2/2010 | Bennett |
| 2010/0114119 A1 | 5/2010 | McLawhorn et al. |
| 2010/0114156 A1 | 5/2010 | Mehl |

(56) References Cited

U.S. PATENT DOCUMENTS

| | | |
|---|---|---|
| 2010/0114159 A1 | 5/2010 | Roorda et al. |
| 2010/0130965 A1 | 5/2010 | Sibbitt et al. |
| 2010/0160958 A1 | 6/2010 | Clark |
| 2010/0168790 A1 | 7/2010 | Clark |
| 2010/0179567 A1 | 7/2010 | Voss et al. |
| 2010/0179571 A1 | 7/2010 | Voss |
| 2010/0179572 A1 | 7/2010 | Voss et al. |
| 2010/0179589 A1 | 7/2010 | Roorda et al. |
| 2010/0179590 A1 | 7/2010 | Fortson et al. |
| 2010/0185216 A1 | 7/2010 | Garrison et al. |
| 2010/0185234 A1 | 7/2010 | Fortson et al. |
| 2010/0217132 A1 | 8/2010 | Ellingwood et al. |
| 2010/0249828 A1 | 9/2010 | Mavani et al. |
| 2011/0054492 A1 | 3/2011 | Clark |
| 2011/0060355 A1 | 3/2011 | Carley et al. |
| 2011/0066163 A1 | 3/2011 | Cho et al. |
| 2011/0066164 A1 | 3/2011 | Walberg et al. |
| 2011/0071565 A1 | 3/2011 | Ginn |
| 2011/0082495 A1 | 4/2011 | Ruiz |
| 2011/0106148 A1 | 5/2011 | Ginn et al. |
| 2011/0137340 A1 | 6/2011 | Cummins |
| 2011/0144663 A1 | 6/2011 | Cummins et al. |
| 2011/0144664 A1 | 6/2011 | Jabba et al. |
| 2011/0144668 A1 | 6/2011 | Carley et al. |
| 2011/0144691 A1 | 6/2011 | Cummins |
| 2011/0166584 A1 | 7/2011 | Palermo et al. |
| 2011/0178548 A1 | 7/2011 | Tenerz |
| 2011/0190793 A1 | 8/2011 | Nobles et al. |
| 2011/0218568 A1 | 9/2011 | Voss |
| 2011/0224719 A1 | 9/2011 | Fortson |
| 2011/0230897 A1 | 9/2011 | Palermo et al. |
| 2011/0238089 A1 | 9/2011 | Reyes et al. |
| 2011/0270282 A1 | 11/2011 | Lemke |
| 2011/0288563 A1 | 11/2011 | Gianotti et al. |
| 2011/0313452 A1 | 12/2011 | Carley et al. |
| 2012/0029555 A1 | 2/2012 | Fortson et al. |
| 2012/0035630 A1 | 2/2012 | Roorda |
| 2012/0101520 A1 | 4/2012 | Ginn et al. |
| 2012/0143216 A1 | 6/2012 | Voss |
| 2012/0209317 A1 | 8/2012 | Oepen |
| 2012/0245603 A1 | 9/2012 | Voss |
| 2012/0245623 A1 | 9/2012 | Kariniemi et al. |
| 2012/0245626 A1 | 9/2012 | Ellingwood et al. |
| 2012/0255655 A1 | 10/2012 | Carley et al. |
| 2012/0296372 A1 | 11/2012 | Ziobro |
| 2012/0310261 A1 | 12/2012 | Cummins et al. |
| 2013/0006274 A1 | 1/2013 | Walberg et al. |
| 2013/0053792 A1 | 2/2013 | Fischell et al. |
| 2013/0138144 A1 | 5/2013 | Yribarren |
| 2013/0165956 A1 | 6/2013 | Sherts et al. |
| 2013/0178872 A1 | 7/2013 | Shriver |
| 2013/0190778 A1 | 7/2013 | Palermo et al. |
| 2013/0190810 A1 | 7/2013 | Roorda et al. |
| 2013/0253539 A1 | 9/2013 | Walberg et al. |
| 2013/0310853 A1 | 11/2013 | Zaugg et al. |
| 2013/0338708 A1 | 12/2013 | Cummins et al. |
| 2014/0005692 A1 | 1/2014 | Ellingwood et al. |
| 2014/0018850 A1 | 1/2014 | Ellingwood |
| 2014/0039549 A1 | 2/2014 | Belsky et al. |
| 2014/0081318 A1 | 3/2014 | Houser et al. |
| 2014/0142624 A1 | 5/2014 | Pantages et al. |
| 2014/0180311 A1 | 6/2014 | Voss |
| 2014/0222068 A1 | 8/2014 | Carley et al. |
| 2014/0222069 A1 | 8/2014 | Carley et al. |
| 2014/0309686 A1 | 10/2014 | Ginn et al. |
| 2014/0364900 A1 | 12/2014 | Fortson et al. |
| 2014/0364903 A1 | 12/2014 | Roorda et al. |
| 2015/0073471 A1 | 3/2015 | Clark |
| 2015/0080914 A1 | 3/2015 | Roundy et al. |
| 2015/0190071 A1 | 7/2015 | Ellingwood et al. |
| 2015/0265279 A1 | 9/2015 | Walberg et al. |
| 2016/0000417 A1 | 1/2016 | Voss |
| 2016/0051258 A1 | 2/2016 | Cummins et al. |
| 2016/0120546 A1 | 5/2016 | Roundy et al. |
| 2016/0151057 A1 | 6/2016 | Voss |
| 2016/0174954 A1 | 6/2016 | Palermo et al. |
| 2016/0192913 A1 | 7/2016 | Kokish |
| 2016/0213357 A1 | 7/2016 | Mehl |
| 2016/0242749 A1 | 8/2016 | Voss |
| 2017/0020496 A1 | 1/2017 | Yribarren |
| 2017/0020517 A1 | 1/2017 | Coleman et al. |
| 2017/0049426 A1 | 2/2017 | Gianotti et al. |
| 2017/0135680 A1 | 5/2017 | Pantages et al. |
| 2017/0135684 A1 | 5/2017 | Carley et al. |
| 2018/0256166 A1 | 9/2018 | Cummins et al. |
| 2018/0325506 A1 | 11/2018 | Ellingwood |
| 2019/0021735 A1 | 1/2019 | Walberg et al. |
| 2019/0117205 A1 | 4/2019 | Kokish |
| 2019/0117207 A1 | 4/2019 | Carley et al. |
| 2019/0350569 A1 | 11/2019 | Palermo et al. |
| 2020/0138423 A1 | 5/2020 | Voss |

FOREIGN PATENT DOCUMENTS

| | | |
|---|---|---|
| CA | 2339060 A1 | 2/2000 |
| DE | 19711288 A1 | 10/1998 |
| DE | 29723736 U1 | 2/1999 |
| DE | 19859952 A1 | 2/2000 |
| DE | 102006056283 A1 | 6/2008 |
| EP | 0386361 A1 | 9/1990 |
| EP | 0534696 A1 | 3/1993 |
| EP | 0621032 A1 | 10/1994 |
| EP | 0744237 A1 | 11/1996 |
| EP | 0756851 A2 | 2/1997 |
| EP | 0774237 A2 | 5/1997 |
| EP | 0858776 A2 | 8/1998 |
| EP | 0941697 A1 | 9/1999 |
| EP | 1867287 A2 | 12/2007 |
| FR | 2443238 A1 | 7/1980 |
| FR | 2715290 A1 | 7/1995 |
| FR | 2722975 A1 | 2/1996 |
| FR | 2768324 A1 | 3/1999 |
| GB | 1358466 A | 7/1974 |
| GB | 2075144 A | 11/1981 |
| GB | 2397240 A | 7/2004 |
| IE | 2000/0722 | 10/2001 |
| IE | 2000/0724 | 10/2001 |
| IE | 2001/0547 | 7/2002 |
| IE | 2001/0815 | 7/2002 |
| IE | 2001/0748 | 8/2002 |
| IE | 2001/0749 | 8/2002 |
| IE | 2002/0452 | 12/2002 |
| IE | 2002/0664 | 2/2003 |
| IE | 2002/0665 | 2/2003 |
| IE | 2002/0451 | 7/2003 |
| IE | 2002/0552 | 7/2003 |
| IE | 2003/0424 | 12/2003 |
| IE | 2003/0490 | 1/2004 |
| IE | 2004/0368 | 11/2005 |
| IE | 2005/0342 | 11/2005 |
| JP | 58-181006 U | 12/1983 |
| JP | 01-274750 A | 11/1989 |
| JP | 01-275750 A | 11/1989 |
| JP | 09-218875 A | 8/1997 |
| JP | 11-500642 A | 1/1999 |
| JP | 2000-102546 A | 4/2000 |
| NL | 9302140 A | 7/1995 |
| PL | 171425 B1 | 4/1997 |
| RU | 2086192 C1 | 8/1997 |
| SU | 0197801 | 6/1967 |
| SU | 0495067 A1 | 12/1975 |
| SU | 0912155 A1 | 3/1982 |
| SU | 1243708 A1 | 7/1986 |
| SU | 1324650 A1 | 7/1987 |
| SU | 1405828 A1 | 6/1988 |
| SU | 1456109 A1 | 2/1989 |
| SU | 1560133 A1 | 4/1990 |
| WO | 95/21573 A1 | 8/1995 |
| WO | 96/24291 A1 | 8/1996 |
| WO | 97/00046 A1 | 1/1997 |
| WO | 97/07741 A1 | 3/1997 |
| WO | 97/27897 A1 | 8/1997 |
| WO | 97/28745 A1 | 8/1997 |
| WO | 98/06346 A1 | 2/1998 |

(56) References Cited

FOREIGN PATENT DOCUMENTS

| | | |
|---|---|---|
| WO | 98/06448 A1 | 2/1998 |
| WO | 98/16161 A1 | 4/1998 |
| WO | 98/17179 A1 | 4/1998 |
| WO | 98/18389 A1 | 5/1998 |
| WO | 98/25508 A2 | 6/1998 |
| WO | 98/58591 A1 | 12/1998 |
| WO | 99/21491 A1 | 5/1999 |
| WO | 99/40849 A1 | 8/1999 |
| WO | 99/60941 A1 | 12/1999 |
| WO | 99/62415 A1 | 12/1999 |
| WO | 00/06029 A1 | 2/2000 |
| WO | 00/07505 A1 | 2/2000 |
| WO | 00/27311 A1 | 5/2000 |
| WO | 00/27313 A2 | 5/2000 |
| WO | 00/56228 A1 | 9/2000 |
| WO | 2000/056227 A1 | 9/2000 |
| WO | 00/71032 A2 | 11/2000 |
| WO | 01/21058 A2 | 3/2001 |
| WO | 01/35832 A2 | 5/2001 |
| WO | 01/47594 A1 | 7/2001 |
| WO | 01/49186 A2 | 7/2001 |
| WO | 01/91628 A2 | 12/2001 |
| WO | 02/19915 A1 | 3/2002 |
| WO | 02/19920 A1 | 3/2002 |
| WO | 02/19922 A1 | 3/2002 |
| WO | 02/19924 A1 | 3/2002 |
| WO | 02/28286 A1 | 4/2002 |
| WO | 02/38055 A2 | 5/2002 |
| WO | 02/45593 A2 | 6/2002 |
| WO | 02/45594 A2 | 6/2002 |
| WO | 02/62234 A2 | 8/2002 |
| WO | 02/98302 A1 | 12/2002 |
| WO | 03/13363 A1 | 2/2003 |
| WO | 03/13364 A1 | 2/2003 |
| WO | 03/47434 A1 | 6/2003 |
| WO | 03/71955 A2 | 9/2003 |
| WO | 03/71956 A2 | 9/2003 |
| WO | 03/71957 A2 | 9/2003 |
| WO | 03/94748 A1 | 11/2003 |
| WO | 2003/101310 A1 | 12/2003 |
| WO | 2004/004578 A1 | 1/2004 |
| WO | 2004/012602 A2 | 2/2004 |
| WO | 2004/060169 A2 | 7/2004 |
| WO | 2004/069054 A2 | 8/2004 |
| WO | 2005/000126 A2 | 1/2005 |
| WO | 2005/006990 A2 | 1/2005 |
| WO | 2005/041782 A2 | 5/2005 |
| WO | 2005/063129 A2 | 7/2005 |
| WO | 2005/082256 A1 | 9/2005 |
| WO | 2005/092204 A2 | 10/2005 |
| WO | 2005/110240 A1 | 11/2005 |
| WO | 2005/112782 A1 | 12/2005 |
| WO | 2005/115251 A1 | 12/2005 |
| WO | 2005/115521 A1 | 12/2005 |
| WO | 2006/000514 A1 | 1/2006 |
| WO | 2006/026116 A1 | 3/2006 |
| WO | 2006/052611 A1 | 5/2006 |
| WO | 2006/052612 A1 | 5/2006 |
| WO | 2006/078578 A2 | 7/2006 |
| WO | 2006/083889 A1 | 8/2006 |
| WO | 2006/115901 A1 | 11/2006 |
| WO | 2006/115904 A2 | 11/2006 |
| WO | 2006/118877 A2 | 11/2006 |
| WO | 2007/005585 A2 | 1/2007 |
| WO | 2007/025014 A2 | 3/2007 |
| WO | 2007/025017 A2 | 3/2007 |
| WO | 2007/025018 A2 | 3/2007 |
| WO | 2007/025019 A2 | 3/2007 |
| WO | 2007/081836 A1 | 7/2007 |
| WO | 2007/088069 A1 | 8/2007 |
| WO | 2008/031102 A1 | 3/2008 |
| WO | 2008/036384 A2 | 3/2008 |
| WO | 2008/074027 A1 | 6/2008 |
| WO | 2008/150915 A1 | 12/2008 |
| WO | 2009/079091 A1 | 6/2009 |
| WO | 2010/031050 A1 | 3/2010 |
| WO | 2010/062693 A2 | 6/2010 |
| WO | 2010/081101 A2 | 7/2010 |
| WO | 2010/081102 A2 | 7/2010 |
| WO | 2010/081103 A1 | 7/2010 |
| WO | 2010/081106 A1 | 7/2010 |
| ZA | 200100527 | 1/2001 |
| ZA | 200100528 | 1/2001 |

OTHER PUBLICATIONS

Office Action received for U.S. Appl. No. 12/684,470, dated Aug. 30, 2012.
Office Action received for U.S. Appl. No. 12/684,470, dated Dec. 20, 2011.
Office Action received for U.S. Appl. No. 12/684,470, dated Jan. 21, 2016.
Office Action received for U.S. Appl. No. 12/684,470, dated Jun. 4, 2014.
Office Action received for U.S. Appl. No. 12/684,470, dated Mar. 23, 2012.
Office Action received for U.S. Appl. No. 12/684,470, dated Nov. 14, 2014.
Office Action received for U.S. Appl. No. 12/684,542, dated Apr. 16, 2012.
Office Action received for U.S. Appl. No. 12/684,542, dated Dec. 1, 2014.
Office Action received for U.S. Appl. No. 12/684,542, dated Jan. 30, 2012.
Office Action received for U.S. Appl. No. 12/684,542, dated Jun. 18, 2014.
Office Action received for U.S. Appl. No. 12/684,542, dated Sep. 13, 2012.
Office Action received for U.S. Appl. No. 12/684,562, dated Aug. 21, 2012.
Office Action received for U.S. Appl. No. 12/684,562, dated Dec. 28, 2011.
Office Action received for U.S. Appl. No. 12/684,562, dated Feb. 16, 2012.
Office Action received for U.S. Appl. No. 12/684,562, dated Sep. 10, 2014.
Office Action received for U.S. Appl. No. 12/684,569, dated Apr. 23, 2014.
Office Action received for U.S. Appl. No. 12/684,569, dated Dec. 20, 2011.
Office Action received for U.S. Appl. No. 12/684,569, dated Jan. 27, 2012.
Office Action received for U.S. Appl. No. 12/684,569, dated Jul. 30, 2012.
Office Action received for U.S. Appl. No. 12/688,065, dated Apr. 8, 2014.
Office Action received for U.S. Appl. No. 12/688,065, dated Apr. 26, 2012.
Office Action received for U.S. Appl. No. 12/688,065, dated Mar. 13, 2012.
Office Action received for U.S. Appl. No. 12/688,065, dated Oct. 12, 2012.
Office Action received for U.S. Appl. No. 12/688,065, dated Oct. 18, 2013.
Office Action received for U.S. Appl. No. 12/724,304, dated Feb. 10, 2012.
Office Action received for U.S. Appl. No. 12/848,642, dated Apr. 26, 2013.
Office Action received for U.S. Appl. No. 12/848,642, dated Nov. 9, 2012.
Office Action received for U.S. Appl. No. 12/848,642, dated Sep. 20, 2012.
Office Action received for U.S. Appl. No. 12/850,242, dated Apr. 18, 2013.
Office Action received for U.S. Appl. No. 12/850,242, dated Aug. 6, 2012.
Office Action received for U.S. Appl. No. 12/850,242, dated Oct. 17, 2012.

(56) References Cited

OTHER PUBLICATIONS

Office Action received for U.S. Appl. No. 12/897,358, dated Aug. 22, 2011.
Office Action received for U.S. Appl. No. 12/941,809, dated Dec. 13, 2011.
Office Action received for U.S. Appl. No. 12/941,809, dated Jan. 30, 2012.
Office Action received for U.S. Appl. No. 12/941,809, dated Jul. 3, 2013.
Office Action received for U.S. Appl. No. 12/941,809, dated Jun. 1, 2012.
Office Action received for U.S. Appl. No. 12/941,809, dated Nov. 8, 2013.
Office Action received for U.S. Appl. No. 12/945,646, dated Jan. 20, 2011.
Office Action received for U.S. Appl. No. 12/945,646, dated Jul. 6, 2011.
Office Action received for U.S. Appl. No. 12/945,646, dated Oct. 26, 2011.
Office Action received for U.S. Appl. No. 12/955,859, dated Aug. 6, 2012.
Office Action received for U.S. Appl. No. 12/955,859, dated Dec. 15, 2011.
Office Action received for U.S. Appl. No. 12/955,859, dated Jul. 21, 2011.
Office Action received for U.S. Appl. No. 12/955,859, dated May 16, 2013.
Office Action received for U.S. Appl. No. 12/955,859, dated May 26, 2011.
Office Action received for U.S. Appl. No. 12/961,331, dated Dec. 4, 2012.
Office Action received for U.S. Appl. No. 12/961,331, dated Feb. 1, 2013.
Office Action received for U.S. Appl. No. 12/961,331, dated Jul. 3, 2013.
Office Action received for U.S. Appl. No. 12/987,792, dated Jan. 21, 2014.
Office Action received for U.S. Appl. No. 11/344,891, dated May 7, 2010.
Office Action received for U.S. Appl. No. 11/344,891, dated Oct. 7, 2009.
Office Action received for U.S. Appl. No. 11/390,586, dated Jul. 6, 2010.
Office Action received for U.S. Appl. No. 11/390,586, dated Jun. 24, 2009.
Office Action received for U.S. Appl. No. 11/396,141, dated Apr. 30, 2013.
Office Action received for U.S. Appl. No. 11/396,141, dated Aug. 26, 2009.
Office Action received for U.S. Appl. No. 11/396,141, dated May 4, 2010.
Office Action received for U.S. Appl. No. 11/396,141, dated May 22, 2009.
Office Action received for U.S. Appl. No. 11/396,731, dated Feb. 12, 2015.
Office Action received for U.S. Appl. No. 11/396,731, dated Feb. 13, 2009.
Office Action received for U.S. Appl. No. 11/396,731, dated Jun. 29, 2010.
Office Action received for U.S. Appl. No. 11/396,731, dated Mar. 22, 2011.
Office Action received for U.S. Appl. No. 11/396,731, dated May 22, 2009.
Office Action received for U.S. Appl. No. 11/396,731, dated Sep. 1, 2011.
Office Action received for U.S. Appl. No. 11/406,203, dated Mar. 3, 2009.
Office Action received for U.S. Appl. No. 11/406,203, dated May 14, 2007.
Office Action received for U.S. Appl. No. 11/406,203, dated Sep. 16, 2009.
Office Action received for U.S. Appl. No. 11/411,925, dated Feb. 5, 2008.
Office Action received for U.S. Appl. No. 11/411,925, dated Jan. 12, 2009.
Office Action received for U.S. Appl. No. 11/411,925, dated Jun. 6, 2007.
Office Action received for U.S. Appl. No. 11/411,925, dated Oct. 1, 2013.
Office Action received for U.S. Appl. No. 11/411,925, dated Sep. 10, 2009.
Office Action received for U.S. Appl. No. 11/427,297, dated Jan. 30, 2009.
Office Action received for U.S. Appl. No. 11/427,297, dated Mar. 21, 2011.
Office Action received for U.S. Appl. No. 11/427,297, dated Sep. 15, 2009.
Office Action received for U.S. Appl. No. 11/427,309, dated Apr. 20, 2009.
Office Action received for U.S. Appl. No. 11/427,309, dated Apr. 26, 2010.
Office Action received for U.S. Appl. No. 11/427,309, dated Jan. 2, 2009.
Office Action received for U.S. Appl. No. 11/427,309, dated May 28, 2008.
Office Action received for U.S. Appl. No. 11/427,309, dated Nov. 6, 2009.
Office Action received for U.S. Appl. No. 11/427,309, dated Nov. 15, 2010.
Office Action received for U.S. Appl. No. 11/455,993, dated Dec. 16, 2009.
Office Action received for U.S. Appl. No. 11/455,993, dated Feb. 17, 2009.
Office Action received for U.S. Appl. No. 11/455,993, dated Jan. 29, 2014.
Office Action received for U.S. Appl. No. 11/508,715, dated Apr. 26, 2010.
Office Action received for U.S. Appl. No. 11/532,325, dated Dec. 2, 2013.
Office Action received for U.S. Appl. No. 11/532,325, dated Feb. 23, 2009.
Office Action received for U.S. Appl. No. 11/532,325, dated Jan. 5, 2010.
Office Action received for U.S. Appl. No. 11/532,325, dated Jul. 17, 2013.
Office Action received for U.S. Appl. No. 11/532,325, dated Jun. 17, 2009.
Office Action received for U.S. Appl. No. 11/532,576, dated Apr. 23, 2010.
Office Action received for U.S. Appl. No. 11/532,576, dated Mar. 1, 2010.
Office Action received for U.S. Appl. No. 11/674,930, dated Jan. 8, 2009.
Office Action received for U.S. Appl. No. 11/674,930, dated Jan. 8, 2010.
Office Action received for U.S. Appl. No. 11/674,930, dated Jun. 4, 2009.
Office Action received for U.S. Appl. No. 11/675,462, dated Aug. 3, 2011.
Office Action received for U.S. Appl. No. 11/675,462, dated Aug. 31, 2010.
Office Action received for U.S. Appl. No. 11/675,462, dated Dec. 10, 2009.
Office Action received for U.S. Appl. No. 11/744,089, dated Apr. 15, 2013.
Office Action received for U.S. Appl. No. 11/744,089, dated Aug. 8, 2012.
U.S. Appl. No. 10/166,161, Notice of Allowance, dated Mar. 3, 2005.
U.S. Appl. No. 10/166,161, Office Action, dated Nov. 1, 2004.
Advisory Action received for U.S. Appl. No. 09/732,178, dated Jun. 10, 2003.

(56) References Cited

OTHER PUBLICATIONS

Advisory Action received for U.S. Appl. No. 12/106,928, dated Mar. 25, 2014.
Advisory Action received for U.S. Appl. No. 12/961,331, dated Sep. 20, 2013.
Advisory Action received for U.S. Appl. No. 15/056,281, dated Aug. 27, 2018.
Advisory Action received for U.S. Appl. No. 15/069,230, dated Oct. 22, 2018.
Amir Loshakove, et al., "Vascular Closure Device", PCT Publication No. WO 00/56223, Sep. 28, 2000.
Carpenter et al, Midterm results of the multicenter trial of the Powerlink bifurcated system for endovascular aortic aneurysm repair, Journal of Vascular Surgery, vol. 40, No. 5, Nov. 2004, p. 849-859.e5.
Database WPI; Section PQ, Week 200120; Derwent Publications Ltd., London GB; AN 2001-203165; XP002199926 & ZA 200 100 528 A (Anthony T), Feb. 28, 2001 (Feb. 28, 2001) abstract.
Deepak Mital et al, Renal Transplantation Without Sutures Using The Vascular Clipping System for Renal Artery and Vein Anastomosis—A New Technique, Transplantation Issue, Oct. 1996, pp. 1171-1173, vol. 62—No. 8, Section of Transplantation Surgery, Department of General Surqerv, Rush-Presbyterian/St. Luke's Medical Center, Chiqaqo, IL.
DL Wessel et al, Outpatient closure of the patent ductus arteriosus, Circulation, May 1988, pp. 1068-1071, vol. 77—No. 5, Department of Anesthesia, Children's, Boston, MA.
E Pikoulis et al, Arterial reconstruction with vascular clips is safe and quicker than sutured repair, Cardiosvascular Surgery, Dec. 1998, pp. 573-578(6), vol. 6—No. 6, Department of Surgery, Uniformed Services University of the Health Sciences, Bethesda, MD.
Eisenack et al, Percutaneous Endovascular Aortic Aneurysm Repair: A Prospective Evaluation of Safety, Efficiency, and Risk Factors, Journal of Endovascular Ther., 2009, vol. 16, p. 708-713.
Examiners Amendment received for U.S. Appl. No. 10/435,104, dated Jan. 3, 2006.
G Gershony et al, Novel vascular sealing device for closure of percutaneous vascular access sites, Cathet. Cardiovasc. Diagn., Jan. 1998, pp. 82-88, vol. 45.
Greenhalgh et al, Endovascular versus open repair of abdominal aortic aneurysm, The New England journal of medicine, vol. 362, No. 20, 2010, p. 1863-1871.
Grossman, W., Cardiac Catheterization and Angiography, 3rd Ed., Lea & Febiger, Philadelphia, pp. 1-49, 52-247. 1986.
H De Swart et al, A new hemostatic puncture closure device for the immediate sealing of arterial puncture sites, American journal of cardiology, Aug. 1993, pp. 445-449, vol. 72—No. 5, Department of Cardiology, Academic Hospital Maastricht, The Netherlands.
Hand tool for forming telephone connections—comprise pliers with reciprocably driven ram crimping clip around conductors against anvil, Derwent-ACC-No. 1978-B8090A.
Harrith M. Hasson M.D. , Laparoscopic Cannula Cone with Means for Cannula Stabilization and Wound Closure, The Journal of the American Association of Gynecologic Laparoscopists, May 1998, pp. 183-185, vol. 5—No. 2, Division of Obstetrics and Gynecology, University of Chicago, Chigago, IL.
Howell et al, Percutaneous Repair of Abdominal Aortic Aneurysms Using the aneuRx Stent Graft and the Percutaneous Vascular Surgery Device, Catheterization and cardiovascular interventions, vol. 55, No. 3, 2002, p. 281-287.
https://www.thefreedictionary.com/flex, retrieved Sep. 2, 2018, definition of the term flex.
https://www.thefreedictionary.com/integral, retrieved Aug. 20, 2018, definition of the term integral.
Inlet Medical Inc. Brochure, pp. 1-2, referencing OM Elashry et al, Comparative clinical study of port-closure techniques following laparoscopic surgery, Depaliment of Surgery, Mallickrodt Institute of Radiography, J Am Coll Surg., Oct. 1996, pp. 335-344, vol. 183—No. 4.
Interview Summary received for U.S. Appl. No. 14/928,950, dated Jun. 4, 2018.
Interview Summary received for U.S. Appl. No. 15/069,230, dated May 1, 2019.
Interview Summary received for U.S. Appl. No. 15/419,335, dated Oct. 1, 2018.
J. Findlay et al, Carotid Arteriotomy Closure Using a Vascular Clip System, Neurosurgery, Mar. 1998, pp. 550-554, vol. 42—No. 3, Division of Neurosurgery, University of Alberta, Edmonton, Canada.
Jean-Baptiste et al., Percutaneous closure devices for endovascular repair of intrarenal abdominal aortic aneurysms: a prospective, non-randomized comparative study, European Journal of Vascular and Endovascular Surgery, vol. 35, No. 4, 2008, p. 422-428.
Jeremy L Gilbert Phd, Wound Closure Biomaterials and Devices, Shock., Mar. 1999, p. 226, vol. 11—No. 3, Institution Northwestern University (editorial review).
Jochen T. Cremer, MD, et al, Different approaches for minimally invasive closure of atrial septal defects, Ann. Thorac. Surg., Nov. 1998 pp. 1648-1652, vol. 67, a Divison of Thoracic and Cardiovascular Surgery, Surgical Center, Hannover Medical School. Hannover, Germany.
K Narayanan et al, Simultaneous primary closure of four fasciotomy wounds in a single setting using the Sure-Closure device. Injury, Jul. 1996, pp. 449-451, vol. 27—No. 6, Department of Surgery, Mercy Hospital of Pittsburgh, PA.
Krajcer and Gregoric, Totally percutaneous aortic aneurysm repair: methods and outcomes using the fully integrated IntuiTrak endovascular system, The Journal of cardiovascular surgery, vol. 51, No. 4, 2010, p. 493-501.
Lederle et al, Outcomes foilowing endovascular vs open repair of abdominal aortic aneurysm: a randomized trial, Jama, vol. 302, No. 14, 2009, p. 1535-i 542.
Lee et al, Total percutaneous access for endovascular aortic aneurysm repair ("Preclose" technique), Journal oi vascular sur lery, vol. 45, No. 6, 2007, P I 1095-1101.
Malkawi et al, Percutaneous access for endovascular aneurysm repair: a systematic review, European ,Journal oi Vascular and Endovascular Surgery, vol. 39, No. 6, 2010, p. 676-682.
Marshall A.C., Lock J.E., Structural and Compliant Anatomy of the Patent Foramen Ovale in Patients Undergoing Transcatheter Closure, Am Heart J Aug. 2000.; 140(2); pp. 303-307.
McCarthy, et al., "Tension (Stay) Suture Bridge", J. of International College of Surgeons, 34(5), pp. 613-614 (Nov. 1960).
MD Gonze et al, Complications associated with percutaneous closure devices, Conference: Annual Meeting of the Society for Clinical Vascular Surgery, The American journal of surgery, Mar. 1999, pp. 209-211, vol. 178, No. 3, Department of Surgery, Section of Vascular Surgery, Ochsner Medical Institutions, New Orleans, LA.
MD Hellinger et al, Effective peritoneal and fascial closure of abdominal trocar sites utilizing the Endo-Judge, J Laparoendosc Surg., Oct. 1996, pp. 329-332, vol. 6—No. 5, Orlando Regional Medical Center, FL.
Michael Gianturco, A Play on Catheterization, Forbes, Dec. 1996, p. 146, vol. 158—No. 15.
Morasch et al, Percutaneous repair of abdominal aortic aneurysm, Journal of vascular surgery, vol. 40, No. 1, 2004, p. 12-16.
Notice of Allowance received for U.S. Appl. No. 09/478,179, dated Nov. 6, 2000.
Notice of Allowance received for U.S. Appl. No. 09/546,998, dated May 6, 2002.
Notice of Allowance received for U.S. Appl. No. 09/610,238, dated Feb. 11, 2002.
Notice of Allowance received for U.S. Appl. No. 09/610,238, dated Mar. 26, 2001.
Notice of Allowance received for U.S. Appl. No. 09/680,837, dated Jun. 16, 2003.
Notice of Allowance received for U.S. Appl. No. 09/732,178, dated Nov. 17, 2003.
Notice of Allowance received for U.S. Appl. No. 09/732,835, dated Mar. 17, 2004.
Notice of Allowance received for U.S. Appl. No. 11/959,334, dated Apr. 14, 2010.

(56) References Cited

OTHER PUBLICATIONS

Notice of Allowance received for U.S. Appl. No. 11/959,334, dated Jan. 12, 2010.
Notice of Allowance received for U.S. Appl. No. 11/959,334, dated Jul. 23, 2010.
Notice of Allowance received for U.S. Appl. No. 12/106,928, dated Oct. 3, 2014.
Notice of Allowance received for U.S. Appl. No. 12/106,937, dated Mar. 5, 2015.
Notice of Allowance received for U.S. Appl. No. 12/113,851, dated Feb. 20, 2015.
Notice of Allowance received for U.S. Appl. No. 12/114,091, dated Apr. 6, 2016.
Notice of Allowance received for U.S. Appl. No. 12/122,603, dated Sep. 23, 2015.
Notice of Allowance received for U.S. Appl. No. 12/143,020, dated Feb. 23, 2012.
Notice of Allowance received for U.S. Appl. No. 12/393,877, dated Aug. 4, 2014.
Notice of Allowance received for U.S. Appl. No. 12/402,398, dated Mar. 13, 2013.
Notice of Allowance received for U.S. Appl. No. 12/403,256, dated Aug. 19, 2010.
Notice of Allowance received for U.S. Appl. No. 12/481,377, dated Aug. 10, 2012.
Notice of Allowance received for U.S. Appl. No. 12/608,769, dated Nov. 5, 2012.
Notice of Allowance received for U.S. Appl. No. 12/608,773, dated Sep. 17, 2015.
Notice of Allowance received for U.S. Appl. No. 12/642,319, dated May 27, 2014.
Notice of Allowance received for U.S. Appl. No. 12/684,400, dated Jul. 28, 2015.
Notice of Allowance received for U.S. Appl. No. 12/684,470, dated Apr. 22, 2016.
Notice of Allowance received for U.S. Appl. No. 12/684,562, dated Feb. 17, 2015.
Notice of Allowance received for U.S. Appl. No. 12/848,642, dated Feb. 3, 2014.
Notice of Allowance received for U.S. Appl. No. 12/850,242, dated Aug. 6, 2013.
Notice of Allowance received for U.S. Appl. No. 12/897,358, dated Jan. 12, 2012.
Notice of Allowance received for U.S. Appl. No. 12/897,358, dated Mar. 5, 2012.
Notice of Allowance received for U.S. Appl. No. 12/941,809, dated Feb. 3, 2014.
Notice of Allowance received for U.S. Appl. No. 12/945,646, dated Feb. 21, 2012.
Notice of Allowance received for U.S. Appl. No. 12/950,628, dated Apr. 25, 2014.
Notice of Allowance received for U.S. Appl. No. 12/955,859, dated Aug. 1, 2013.
Notice of Allowance received for U.S. Appl. No. 12/961,331, dated Apr. 25, 2014.
Notice of Allowance received for U.S. Appl. No. 12/966,923, dated Feb. 3, 2012.
Notice of Allowance received for U.S. Appl. No. 12/973,204, dated Mar. 7, 2012.
Notice of Allowance received for U.S. Appl. No. 12/987,792, dated Aug. 25, 2014.
Notice of Allowance received for U.S. Appl. No. 13/028,041, dated Aug. 21, 2013.
Notice of Allowance received for U.S. Appl. No. 13/030,922, dated Jan. 8, 2014.
Notice of Allowance received for U.S. Appl. No. 13/039,087, dated Nov. 6, 2012.
Notice of Allowance received for U.S. Appl. No. 13/112,618, dated Jul. 6, 2016.
Notice of Allowance received for U.S. Appl. No. 13/153,594, dated Oct. 16, 2013.
Notice of Allowance received for U.S. Appl. No. 13/222,899, dated Jan. 7, 2016.
Notice of Allowance received for U.S. Appl. No. 13/308,227, dated Feb. 1, 2016.
Notice of Allowance received for U.S. Appl. No. 13/488,233, dated Feb. 5, 2013.
Notice of Allowance received for U.S. Appl. No. 13/490,143, dated Apr. 29, 2013.
Notice of Allowance received for U.S. Appl. No. 13/525,839, dated Jul. 15, 2013.
Notice of Allowance received for U.S. Appl. No. 13/725,589, dated Mar. 18, 2016.
Notice of Allowance received for U.S. Appl. No. 13/791,829, dated Oct. 8, 2013.
Notice of Allowance received for U.S. Appl. No. 13/791,846, dated Oct. 27, 2015.
Notice of Allowance received for U.S. Appl. No. 13/898,202, dated Feb. 10, 2015.
Notice of Allowance received for U.S. Appl. No. 13/908,796, dated Nov. 6, 2015.
Notice of Allowance received for U.S. Appl. No. 14/017,039, dated Apr. 4, 2016.
Notice of Allowance received for U.S. Appl. No. 14/023,428, dated Jan. 4, 2018.
Notice of Allowance received for U.S. Appl. No. 14/077,007, dated Aug. 12, 2016.
Notice of Allowance received for U.S. Appl. No. 14/246,926, dated Oct. 3, 2016.
Office Action received for U.S. Appl. No. 11/427,297, dated Sep. 15, 2010.
Office Action received for U.S. Appl. No. 13/111,371, dated Oct. 12, 2012.
OM Elashry et al, Comparative clinical study of port-closure techniques following laparoscopic surgery, Department of Surgery, Mallickrodt Institute of Radiography, J Am Coll Surg., Oct. 1996, pp. 335-344, vol. 183—No. 4.
P M N Werker, et al, Review of facilitated approaches to vascular anastomosis surgery towards minimally invasive coronary artery bypass grafting, Conference: Utrecht MICABG Workshop 2, The Annals of thoracic surgery, Apr. 1996, pp. 122-127, vol. 63—No. 6, Department of Plastic, Reconstructive and Hand surgery, University Hospital Utrecht Netherlands Departments of Cardiology and Cardiopulmonary Surgery, Heart Lung Institute, Utrecht Netherlands.; Utrect University Hospital Utrecht Netherlands.
PCT Publication No. WO 00/07640 entitled, "Vascular Suction Cannula, Dilator and Surgical Stapler", Feb. 17, 2000.
PCT Publication No. WO 00/56223 entitled "Vascular Closure Device", Sep. 28, 2000.
PCT Publication No. WO 97/20505, "Vascular Wound Closure Device", Yong Zhu, et al., Jun. 12, 1997.
PCT Publication No. WO 98/24374, "Vascular Wound Closure System", Yong Zhu, et al., Jun. 11, 1998.
PCT Publication No. WO 99/62408 entitled, "Vascular Port device", Dec. 9, 1999.
Peter Rhee MD et al, Use of Titanium Vascular Staples in Trauma, Journal of Trauma-Injury Infection & Critical Care, Dec. 1998, pp. 1097-1099, vol. 45—No. 6, Institution from the Department of Surgery, Washington Hospital Center, Washington DC, and Uniformed Services University of the Health Sciences, Bethesda, Maryland.
PM N Werker, et al, Review of facilitated approaches to vascular anastomosis surgery, Conference: Utrecht MICABG Workshop 2, The Annals of thoracic surgery, Apr. 1996, pp. S122-S127, vol. 63—No. 6, Department of Plastic, Reconstructive and Hand surgery, University Hospital Utrecht Netherlands Departments of Cardiology and Cardiopulmonary Surgery, Heart Lung Institute, Utrecht Netherlands.; Utrect University Hospital Utrecht Netherlands.
ProstarXL—Percutaneous Vascular Surgical Device, www.Archive.org, Jun. 1998, Original Publisher: http://prostar.com, may also be found at http://web.archive.org/web/19980630040429/www.perclose.com/html/prstrxl.html.

(56) References Cited

OTHER PUBLICATIONS

Rachel et al, Percutaneous endovascular abdominal aortic aneurysm repair, Annals of vascular surgery, vol. 16, No. 1, 2002, p. 43-49.
Restriction Requirement received for U.S. Appl. No. 10/638,115, dated Sep. 22, 2006.
Sa Beyer-Enke et al, Immediate sealing of arterial puncture site following femoropopliteal angioplasty: A prospective randomized trial, Cardiovascular and Interventional Radiology 1996, Nov.-Dec. 1996, pp. 406-410, vol. 19—No. 6, Gen Hosp North, Dept Dianost & Intervent Radiol, Nurnberg, Germany (Reprint).
Scott Hensley, Closing Wounds. New Devices seal arterial punctures in double time, Modern Healthcare (United States), Mar. 23, 2008, p. 48.
Sigmund Silber et al, A novel vascular device for closure of percutaneous arterial access sites, The American Jornal of Cardiology, Apr. 1999, pp. 1248-1252, vol. 83—No. 8.
Simonetta Blengino et al, A Randomized Study of the 8 French Hemostatic Puncture Closure Device vs Manual Compression After Coronary Interventions, Journal of the American College of Cardiology, Feb. 1995, p. 262A, vol. 25.—No. 2, Supplement 1.
Starnes et al, Totally percutaneous aortic aneurysm repair: experience anc! prudence, Journal of vascular surgery, vol. 43, No. 2, 2006, p. 270-276.
Stretch Comb by Scunci, retrieved via internet at www.scunci.com/ productdetail by examiner on Oct. 9, 2007, publication date unavailable.
Swee Lian Tan, MD, PhD, FACS, Explanation of Infected Hemostatic Puncture Closure Devices—A Case Report, Vascular and Endovascular Surgery, 1999, pp. 507-510, vol. 33—No. 5, Parkland Medical Center, Derry, New Hampshire.
SY Nakada et al, Comparison of newer laparoscopic port closure techniques in the porcine model, J Endourol, Oct. 1995, pp. 397-401, vol. 9—No. 5, Department of Surgery/Urology, University of Wisconsin Medical School, Madison.
Taber's Cyclopedic Medical Dictionary, 18$^{th}$ Ed. 1997, pp. 747 and 1420.
Teh et al, Use of the percutaneous vascular surgery device for closure of femoral access sites during endovascular aneurysm repair: lessons from our experience, European Journal of Vascular and Endovascular Surgery, vol. 22, No. 5, 2001, p. 418-423.
Tomoaki Hinohara, Percutaneous vascular surgery (Prostar.RTM. Plus and Techstar.RTM. for femoral artery site closure). Interventional Cardiology Newsletter, May-Jul. 1997, pp. 19-28, vol. 5—No. 3-4.
Torsello et al, Endovascular suture versus cutciown for endovascular aneurysm repair: a prospective randomized pilot study, Journal of vascular surgery, vol. 38, No. 1, 2003, p. 78-82.
Traul et al, Percutaneous enciovascular repair of intrarenal abdominal aortic aneurysms: a feasibility study, Journal of vascular surgery, vol. 32, No. 4, 2000, p. 770-776.
Turn—macmillandictionary.com/dictionary.american/turn.
U.S. Appl. filed Dec. 30, 2008, Clark., U.S. Appl. No. 61/481,377.
U.S. Appl. filed Jan. 21, 2011, Von Oepen et al., U.S. Appl. No. 13/011,850.
U.S. Appl. filed Jul. 1, 2005, Pantages et al., U.S. Appl. No. 60/696,096.
U.S. Appl. filed Jun. 18, 2012, Carley et al., U.S. Appl. No. 13/525,718.
U.S. Appl. filed May 3, 2007., U.S. Appl. No. 11/744,049.
U.S. Appl. filed Oct. 4, 2010, Carley., U.S. Appl. No. 12/987,358.
U.S. Appl. No. 10/081,725, Mail Date Feb. 9, 2004, Notice of Allowance.
U.S. Appl. No. 10/240,183, Aug. 11, 2006, Response to 312 Amendment.
U.S. Appl. No. 10/264,306, mailed May 26, 2005, Office Action.
U.S. Appl. No. 10/305,923, Mail Date Mar. 3, 2005, Notice of Allowance.
U.S. Appl. No. 10/305,923, Mail Date Nov. 1, 2004, Office Action.
U.S. Appl. No. 10/356,214, filed Apr. 29, 2009, Office Action.
U.S. Appl. No. 10/787,073, filed Nov. 30, 2006, Office Action.
U.S. Appl. No. 11/316,775, filed Aug. 6, 2008, Office Action.
U.S. Appl. No. 11/461,323, filed Jul. 27, 2009, Office Action.
U.S. Appl. No. 11/461,323, Mail Date Apr. 25, 2008, Office Action.
U.S. Appl. No. 11/461,323, mail date Apr. 5, 2010, Notice Of Allowance.
U.S. Appl. No. 11/461,323, Mail Date May 2, 2007, Office Action.
U.S. Appl. No. 11/461,323, mailed Nov. 6, 2008, Office Action.
U.S. Appl. No. 11/461,323, mailed Oct. 29, 2007, Office Action.
Notice of Allowance received for U.S. Appl. No. 10/519,778, dated May 31, 2006.
Notice of Allowance received for U.S. Appl. No. 10/541,083, dated Apr. 16, 2009.
Notice of Allowance received for U.S. Appl. No. 10/541,083, dated Aug. 17, 2010.
Notice of Allowance received for U.S. Appl. No. 10/541,083, dated Dec. 29, 2008.
Notice of Allowance received for U.S. Appl. No. 10/541,083, dated Feb. 5, 2010.
Notice of Allowance received for U.S. Appl. No. 10/541,083, dated May 10, 2010.
Notice of Allowance received for U.S. Appl. No. 10/541,083, dated Sep. 19, 2008.
Notice of Allowance received for U.S. Appl. No. 10/541,083, dated Sep. 30, 2009.
Notice of Allowance received for U.S. Appl. No. 10/616,832, dated Jan. 11, 2010.
Notice of Allowance received for U.S. Appl. No. 10/616,832, dated May 12, 2010.
Notice of Allowance received for U.S. Appl. No. 10/616,832, dated Sep. 20, 2010.
Notice of Allowance received for U.S. Appl. No. 10/617,090, dated Jul. 6, 2005.
Notice of Allowance received for U.S. Appl. No. 10/617,090, dated Oct. 5, 2005.
Notice of Allowance received for U.S. Appl. No. 10/638,115, dated Apr. 2, 2010.
Notice of Allowance received for U.S. Appl. No. 10/638,115, dated Aug. 13, 2010.
Notice of Allowance received for U.S. Appl. No. 10/638,115, dated Dec. 1, 2009.
Notice of Allowance received for U.S. Appl. No. 10/638,115, dated May 7, 2009.
Notice of Allowance received for U.S. Appl. No. 10/667,144, dated Oct. 28, 2011.
Notice of Allowance received for U.S. Appl. No. 10/669,313, dated Jan. 11, 2006.
Notice of Allowance received for U.S. Appl. No. 10/669,313, dated Jun. 28, 2006.
Notice of Allowance received for U.S. Appl. No. 10/682,459, dated Apr. 1, 2011.
Notice of Allowance received for U.S. Appl. No. 10/786,444, dated Jul. 11, 2013.
Notice of Allowance received for U.S. Appl. No. 10/787,073, dated Aug. 25, 2010.
Notice of Allowance received for U.S. Appl. No. 10/787,073, dated Feb. 17, 2010.
Notice of Allowance received for U.S. Appl. No. 10/908,721, dated Jul. 18, 2013.
Notice of Allowance received for U.S. Appl. No. 11/048,503, dated Apr. 26, 2010.
Notice of Allowance received for U.S. Appl. No. 11/048,503, dated Jan. 11, 2010.
Notice of Allowance received for U.S. Appl. No. 11/048,503, dated Jul. 30, 2010.
Notice of Allowance received for U.S. Appl. No. 11/113,549, dated Mar. 14, 2014.
Notice of Allowance received for U.S. Appl. No. 11/152,562, dated Sep. 16, 2010.
Notice of Allowance received for U.S. Appl. No. 11/198,811, dated Jun. 29, 2010.
Notice of Allowance received for U.S. Appl. No. 11/344,891, dated Jan. 22, 2013.
Notice of Allowance received for U.S. Appl. No. 11/390,586, dated May 3, 2012.

(56) References Cited

OTHER PUBLICATIONS

Notice of Allowance received for U.S. Appl. No. 11/396,141, dated Nov. 4, 2013.
Notice of Allowance received for U.S. Appl. No. 11/396,731, dated Jul. 9, 2015.
Notice of Allowance received for U.S. Appl. No. 11/406,203, dated Jan. 29, 2008.
Notice of Allowance received for U.S. Appl. No. 11/406,203, dated Jun. 18, 2010.
Notice of Allowance received for U.S. Appl. No. 11/406,203, dated May 23, 2008.
Notice of Allowance received for U.S. Appl. No. 11/406,203, dated Sep. 22, 2008.
Notice of Allowance received for U.S. Appl. No. 11/411,925, dated Feb. 5, 2014.
Notice of Allowance received for U.S. Appl. No. 11/427,297, dated Jun. 26, 2012.
Notice of Allowance received for U.S. Appl. No. 11/427,309, dated Jun. 7, 2013.
Notice of Allowance received for U.S. Appl. No. 11/455,993, dated Aug. 11, 2014.
Notice of Allowance received for U.S. Appl. No. 11/532,325, dated Jan. 16, 2015.
Notice of Allowance received for U.S. Appl. No. 11/674,930, dated Apr. 3, 2014.
Notice of Allowance received for U.S. Appl. No. 11/675,462, dated Dec. 22, 2011.
Notice of Allowance received for U.S. Appl. No. 11/744,089, dated Aug. 8, 2013.
Notice of Allowance received for U.S. Appl. No. 11/767,818, dated Feb. 3, 2012.
Notice of Allowance received for U.S. Appl. No. 11/852,190, dated Feb. 12, 2014.
Notice of Allowance received for U.S. Appl. No. 11/958,295, dated Jun. 13, 2014.
Notice of Allowance received for U.S. Appl. No. 14/246,973, dated Nov. 9, 2016.
Notice of Allowance received for U.S. Appl. No. 14/312,339, dated Jul. 19, 2018.
Notice of Allowance received for U.S. Appl. No. 14/323,753, dated Apr. 15, 2016.
Notice of Allowance received for U.S. Appl. No. 14/466,576, dated Dec. 15, 2015.
Notice of Allowance received for U.S. Appl. No. 14/539,830, dated Nov. 18, 2016.
Notice of Allowance received for U.S. Appl. No. 14/732,977, dated May 29, 2018.
Notice of Allowance received for U.S. Appl. No. 14/839,658, dated Feb. 28, 2018.
Notice of Allowance received for U.S. Appl. No. 15/056,281, dated Apr. 17, 2019.
Notice of Allowance received for U.S. Appl. No. 15/069,230, dated Jun. 19, 2019.
Notice of Allowance received for U.S. Appl. No. 15/142,106, dated Sep. 25, 2019.
Notice of Allowance received for U.S. Appl. No. 15/344,978, dated Sep. 25, 2019.
Notice of Allowance received for U.S. Appl. No. 15/356,028, dated Nov. 20, 2018.
Notice of Allowance received for U.S. Appl. No. 15/419,335, dated Nov. 30, 2018.
Notice of Allowance received for U.S. Appl. No. 10/147,774, dated Feb. 4, 2008.
Notice of Allowance received for U.S. Appl. No. 11/532,576, dated Oct. 13, 2010.
Notice of Allowance received for U.S. Appl. No. 13/615,547, dated Apr. 12, 2013.
Office Action received for U.S. Appl. No. 14/839,658, dated May 30, 2017.
Office Action received for U.S. Appl. No. 09/610,238, dated Sep. 5, 2001.
Office Action received for U.S. Appl. No. 09/680,837, dated Jul. 9, 2002.
Office Action received for U.S. Appl. No. 09/680,837, dated Mar. 25, 2003.
Office Action Received for U.S. Appl. No. 09/680,837, dated Nov. 6, 2002.
Office Action Received for U.S. Appl. No. 09/732,178, dated Aug. 1, 2002.
Office Action Received for U.S. Appl. No. 09/732,178, dated Dec. 24, 2002.
Office Action Received for U.S. Appl. No. 09/732,178, dated Jul. 3, 2003.
Office Action Received for U.S. Appl. No. 09/732,835, dated Feb. 9, 2004.
Office Action received for U.S. Appl. No. 09/732,835, dated Sep. 11, 2003.
Office Action Received for U.S. Appl. No. 09/764,813, dated Mar. 26, 2001.
Office Action Received for U.S. Appl. No. 09/933,299, dated Feb. 26, 2003.
Office Action Received for U.S. Appl. No. 09/949,398, dated Mar. 4, 2003.
Office Action received for U.S. Appl. No. 09/949,438, dated Dec. 17, 2002.
Office Action received for U.S. Appl. No. 10/006,400, dated Apr. 2, 2008.
Office Action received for U.S. Appl. No. 10/006,400, dated Apr. 11, 2005.
Office Action received for U.S. Appl. No. 10/006,400, dated Apr. 19, 2007.
Office Action received for U.S. Appl. No. 10/006,400, dated Aug. 27, 2004.
Office Action received for U.S. Appl. No. 10/006,400, dated Feb. 23, 2005.
Office Action received for U.S. Appl. No. 10/006,400, dated Jan. 2, 2009.
Office Action received for U.S. Appl. No. 10/006,400, dated Jul. 27, 2005.
Office Action received for U.S. Appl. No. 10/006,400, dated Mar. 6, 2006.
Office Action received for U.S. Appl. No. 10/006,400, dated May 24, 2006.
Office Action received for U.S. Appl. No. 10/006,400, dated Oct. 26, 2006.
Office Action received for U.S. Appl. No. 10/081,723, dated Sep. 29, 2004.
Office Action received for U.S. Appl. No. 10/081,725, dated Apr. 13, 2004.
Office Action received for U.S. Appl. No. 10/147,774, dated Jun. 8, 2010.
Office Action received for U.S. Appl. No. 10/147,774, dated Jun. 30, 2008.
Office Action received for U.S. Appl. No. 10/147,774, dated Mar. 18, 2009.
Office Action received for U.S. Appl. No. 10/147,774, dated May 4, 2005.
Office Action received for U.S. Appl. No. 10/147,774, dated Nov. 4, 2004.
Office Action received for U.S. Appl. No. 10/147,774, dated Oct. 18, 2005.
Office Action received for U.S. Appl. No. 10/147,774, dated Oct. 26, 2009.
Office Action received for U.S. Appl. No. 10/240,183, dated Aug. 11, 2006.
Office Action received for U.S. Appl. No. 12/987,792, dated Jun. 11, 2014.
Office Action received for U.S. Appl. No. 12/987,792, dated Mar. 13, 2012.
Office Action received for U.S. Appl. No. 12/987,792, dated Sep. 17, 2012.

(56) References Cited

OTHER PUBLICATIONS

Office Action received for U.S. Appl. No. 13/026,989, dated Aug. 23, 2013.
Office Action received for U.S. Appl. No. 13/026,989, dated Jun. 8, 2012.
Office Action received for U.S. Appl. No. 13/026,989, dated Sep. 16, 2011.
Office Action received for U.S. Appl. No. 13/028,041, dated Feb. 26, 2013.
Office Action Received for U.S. Appl. No. 13/028,041, dated Jan. 4, 2013.
Office Action received for U.S. Appl. No. 13/030,922, dated Dec. 18, 2012.
Office Action received for U.S. Appl. No. 13/030,922, dated Jan. 31, 2013.
Office Action received for U.S. Appl. No. 13/030,922, dated Jul. 18, 2013.
Office Action received for U.S. Appl. No. 13/039,087, dated Jul. 17, 2012.
Office Action received for U.S. Appl. No. 13/112,618, dated Dec. 15, 2014.
Office Action received for U.S. Appl. No. 13/112,618, dated Jan. 29, 2016.
Office Action received for U.S. Appl. No. 13/112,618, dated Jun. 7, 2013.
Office Action received for U.S. Appl. No. 13/112,618, dated Mar. 29, 2013.
Office Action received for U.S. Appl. No. 13/112,618, dated May 18, 2015.
Office Action received for U.S. Appl. No. 13/112,618, dated Nov. 20, 2013.
Office Action received for U.S. Appl. No. 13/112,631, dated Apr. 15, 2015.
Office Action received for U.S. Appl. No. 13/112,631, dated Dec. 2, 2013.
Office Action received for U.S. Appl. No. 13/112,631, dated Jun. 26, 2013.
Office Action received for U.S. Appl. No. 13/112,631, dated Mar. 29, 2013.
Office Action received for U.S. Appl. No. 13/112,631, dated Nov. 20, 2014.
Office Action received for U.S. Appl. No. 13/153,594, dated Jan. 29, 2013.
Office Action received for U.S. Appl. No. 13/153,594, dated May 29, 2013.
Office Action received for U.S. Appl. No. 13/222,899, dated Apr. 1, 2015.
Office Action received for U.S. Appl. No. 13/222,899, dated Aug. 5, 2015.
Office Action received for U.S. Appl. No. 13/222,899, dated Jan. 10, 2014.
Office Action received for U.S. Appl. No. 13/222,899, dated Jul. 31, 2014.
Office Action received for U.S. Appl. No. 13/308,227, dated Apr. 10, 2013.
Office Action received for U.S. Appl. No. 13/308,227, dated Jul. 14, 2015.
Office Action received for U.S. Appl. No. 13/308,227, dated Sep. 11, 2013.
Office Action received for U.S. Appl. No. 13/490,143, dated Jan. 4, 2013.
Office Action received for U.S. Appl. No. 13/525,839, dated Apr. 1, 2013.
Office Action received for U.S. Appl. No. 13/615,547, dated Jan. 18, 2013.
Office Action received for U.S. Appl. No. 13/725,589, dated Sep. 17, 2015.
Office Action received for U.S. Appl. No. 13/791,829, dated May 29, 2013.
Office Action received for U.S. Appl. No. 13/791,846, dated Jun. 4, 2015.
Office Action received for U.S. Appl. No. 13/837,801, dated Dec. 16, 2015.
Office Action received for U.S. Appl. No. 13/837,801, dated Feb. 9, 2017.
Office Action received for U.S. Appl. No. 13/837,801, dated Jul. 6, 2017.
Office Action received for U.S. Appl. No. 13/837,801, dated Jun. 9, 2016.
Office Action received for U.S. Appl. No. 13/898,202, dated Aug. 21, 2014.
Office Action received for U.S. Appl. No. 13/898,202, dated Jan. 3, 2014.
Office Action received for U.S. Appl. No. 13/908,796, dated Jul. 21, 2015.
Office Action received for U.S. Appl. No. 14/017,039, dated Jan. 23, 2015.
Office Action received for U.S. Appl. No. 14/017,039, dated Jun. 10, 2015.
Office Action received for U.S. Appl. No. 14/017,039, dated Oct. 27, 2015.
Office Action received for U.S. Appl. No. 14/023,428, dated Dec. 20, 2016.
Office Action received for U.S. Appl. No. 14/023,428, dated Feb. 9, 2016.
Office Action received for U.S. Appl. No. 12/122,603, dated Apr. 30, 2014.
Office Action received for U.S. Appl. No. 12/122,603, dated Mar. 3, 2011.
Office Action received for U.S. Appl. No. 12/122,603, dated Nov. 20, 2013.
Office Action received for U.S. Appl. No. 12/122,603, dated Sep. 23, 2011.
Office Action received for U.S. Appl. No. 12/135,858, dated Feb. 16, 2012.
Office Action received for U.S. Appl. No. 12/135,858, dated Jul. 13, 2011.
Office Action received for U.S. Appl. No. 12/143,020, dated Aug. 31, 2011.
Office Action received for U.S. Appl. No. 12/143,020, dated May 11, 2011.
Office Action received for U.S. Appl. No. 12/338,977, dated Jan. 19, 2012.
Office Action received for U.S. Appl. No. 12/338,977, dated Jul. 11, 2012.
Office Action received for U.S. Appl. No. 12/338,977, dated Jun. 19, 2013.
Office Action received for U.S. Appl. No. 12/338,977, dated Nov. 28, 2012.
Office Action received for U.S. Appl. No. 12/393,877, dated Dec. 13, 2011.
Office Action received for U.S. Appl. No. 12/393,877, dated May 21, 2012.
Office Action received for U.S. Appl. No. 12/393,877, dated Sep. 29, 2011.
Office Action received for U.S. Appl. No. 12/402,398, dated Jan. 24, 2011.
Office Action received for U.S. Appl. No. 12/402,398, dated Mar. 9, 2010.
Office Action received for U.S. Appl. No. 12/402,398, dated May 20, 2010.
Office Action received for U.S. Appl. No. 12/402,398, dated Sep. 20, 2012.
Office Action received for U.S. Appl. No. 12/403,256, dated Dec. 16, 2009.
Office Action received for U.S. Appl. No. 12/403,256, dated Mar. 30, 2010.
Office Action received for U.S. Appl. No. 12/403,277, dated Apr. 3, 2012.
Office Action received for U.S. Appl. No. 12/403,277, dated Aug. 15, 2014.

(56) References Cited

OTHER PUBLICATIONS

Office Action received for U.S. Appl. No. 12/403,277, dated Jan. 27, 2014.
Office Action received for U.S. Appl. No. 12/403,277, dated Jul. 8, 2010.
Office Action received for U.S. Appl. No. 12/403,277, dated Mar. 31, 2011.
Office Action received for U.S. Appl. No. 12/403,277, dated Nov. 5, 2012.
Office Action received for U.S. Appl. No. 12/403,277, dated Oct. 12, 2010.
Office Action received for U.S. Appl. No. 12/481,377, dated Apr. 28, 2011.
Office Action received for U.S. Appl. No. 12/481,377, dated Jan. 3, 2012.
Office Action received for U.S. Appl. No. 12/481,377, dated Jun. 21, 2011.
Office Action received for U.S. Appl. No. 12/548,274, dated Aug. 14, 2014.
Office Action received for U.S. Appl. No. 12/548,274, dated Dec. 28, 2011.
Office Action received for U.S. Appl. No. 12/548,274, dated Mar. 2, 2012.
Office Action received for U.S. Appl. No. 12/548,274, dated Sep. 10, 2012.
Office Action received for U.S. Appl. No. 12/608,769, dated Aug. 22, 2012.
Office Action received for U.S. Appl. No. 12/608,769, dated Feb. 10, 2012.
Office Action received for U.S. Appl. No. 12/608,773, filed Jan. 7, 2013.
Office Action received for U.S. Appl. No. 12/608,773, dated Jan. 7, 2013.
Office Action received for U.S. Appl. No. 12/608,773, dated Jul. 17, 2014.
Office Action received for U.S. Appl. No. 12/608,773, dated Jul. 20, 2012.
Office Action received for U.S. Appl. No. 12/608,773, dated Jun. 7, 2012.
Office Action received for U.S. Appl. No. 12/608,773, dated Mar. 12, 2015.
Office Action received for U.S. Appl. No. 12/642,319, dated Aug. 28, 2012.
Office Action received for U.S. Appl. No. 12/642,319, dated Dec. 16, 2013.
Office Action received for U.S. Appl. No. 12/642,319, dated Feb. 27, 2012.
Office Action received for U.S. Appl. No. 12/684,400, dated Feb. 13, 2012.
Office Action received for U.S. Appl. No. 12/684,400, dated Feb. 23, 2015.
Office Action received for U.S. Appl. No. 12/684,400, dated May 9, 2012.
Office Action received for U.S. Appl. No. 12/684,400, dated Oct. 16, 2012.
Office Action received for U.S. Appl. No. 11/744,089, dated Aug. 14, 2009.
Office Action received for U.S. Appl. No. 11/744,089, dated Nov. 26, 2008.
Office Action received for U.S. Appl. No. 11/757,108, dated Nov. 25, 2009.
Office Action received for U.S. Appl. No. 11/767,818, dated Dec. 24, 2009.
Office Action received for U.S. Appl. No. 11/767,818, dated Feb. 16, 2011.
Office Action received for U.S. Appl. No. 11/767,818, dated Mar. 22, 2010.
Office Action received for U.S. Appl. No. 11/767,818, dated Sep. 30, 2010.
Office Action received for U.S. Appl. No. 11/852,190, dated Apr. 24, 2013.
Office Action received for U.S. Appl. No. 11/852,190, dated Jun. 24, 2010.
Office Action received for U.S. Appl. No. 11/852,190, dated Mar. 2, 2011.
Office Action received for U.S. Appl. No. 11/852,190, dated Nov. 1, 2010.
Office Action received for U.S. Appl. No. 11/852,190, dated Nov. 26, 2013.
Office Action received for U.S. Appl. No. 11/958,281, dated Mar. 10, 2011.
Office Action received for U.S. Appl. No. 11/958,281, dated Oct. 8, 2010.
Office Action received for U.S. Appl. No. 11/958,281, dated Sep. 2, 2010.
Office Action received for U.S. Appl. No. 11/958,295, dated Aug. 27, 2009.
Office Action received for U.S. Appl. No. 11/958,295, dated May 25, 2010.
Office Action received for U.S. Appl. No. 11/959,334, dated Aug. 19, 2009.
Office Action received for U.S. Appl. No. 12/106,928, dated Dec. 2, 2013.
Office Action received for U.S. Appl. No. 12/106,928, dated Jan. 23, 2009.
Office Action received for U.S. Appl. No. 12/106,928, dated Jun. 28, 2013.
Office Action received for U.S. Appl. No. 12/106,928, dated May 10, 2010.
Office Action received for U.S. Appl. No. 12/106,928, dated Oct. 5, 2009.
Office Action received for U.S. Appl. No. 12/106,928, dated Oct. 25, 2010.
Office Action received for U.S. Appl. No. 12/106,937, dated Jan. 22, 2014.
Office Action received for U.S. Appl. No. 12/106,937, dated Jun. 28, 2013.
Office Action received for U.S. Appl. No. 12/106,937, dated Mar. 30, 2009.
Office Action received for U.S. Appl. No. 12/106,937, dated Nov. 18, 2009.
Office Action received for U.S. Appl. No. 12/113,851, dated Apr. 27, 2010.
Office Action received for U.S. Appl. No. 12/113,851, dated Apr. 27, 2011.
Office Action received for U.S. Appl. No. 12/113,851, dated Aug. 21, 2014.
Office Action received for U.S. Appl. No. 12/113,851, dated Dec. 16, 2010.
Office Action received for U.S. Appl. No. 12/113,851, dated Jun. 24, 2010.
Office Action received for U.S. Appl. No. 12/113,851, dated Mar. 17, 2014.
Office Action received for U.S. Appl. No. 12/113,851, dated Mar. 29, 2012.
Office Action received for U.S. Appl. No. 12/114,031, dated Aug. 2, 2011.
Office Action received for U.S. Appl. No. 12/114,031, dated Mar. 6, 2012.
Office Action received for U.S. Appl. No. 12/114,031, dated Mar. 10, 2014.
Office Action received for U.S. Appl. No. 12/114,031, dated May 11, 2011.
Office Action received for U.S. Appl. No. 12/114,031, dated Nov. 22, 2010.
Office Action received for U.S. Appl. No. 12/114,031, dated Oct. 5, 2010.
Office Action received for U.S. Appl. No. 12/114,091, dated Apr. 5, 2012.
Office Action received for U.S. Appl. No. 12/114,091, dated Dec. 17, 2010.

(56) References Cited

OTHER PUBLICATIONS

Office Action received for U.S. Appl. No. 12/114,091, dated Feb. 12, 2015.
Office Action received for U.S. Appl. No. 12/114,091, dated Jul. 7, 2011.
Office Action received for U.S. Appl. No. 12/114,091, dated Jul. 23, 2015.
Office Action received for U.S. Appl. No. 12/114,091, dated Nov. 8, 2012.
Office Action received for U.S. Appl. No. 12/114,091, dated Oct. 27, 2010.
Office Action received for U.S. Appl. No. 12/122,603, dated Apr. 9, 2015.
Office Action received for U.S. Appl. No. 12/122,603, dated Apr. 22, 2011.
Office Action received for U.S. Appl. No. 10/240,183, dated Dec. 17, 2004.
Office Action received for U.S. Appl. No. 10/240,183, dated Jul. 27, 2004.
Office Action received for U.S. Appl. No. 10/264,306, dated Aug. 13, 2009.
Office Action received for U.S. Appl. No. 10/264,306, dated Feb. 9, 2005.
Office Action received for U.S. Appl. No. 10/264,306, dated Feb. 26, 2009.
Office Action received for U.S. Appl. No. 10/264,306, dated Jan. 27, 2010.
Office Action received for U.S. Appl. No. 10/264,306, dated Jun. 15, 2010.
Office Action received for U.S. Appl. No. 10/264,306, dated Jun. 27, 2008.
Office Action received for U.S. Appl. No. 10/264,306, dated Oct. 4, 2005.
Office Action received for U.S. Appl. No. 10/335,075, dated Apr. 21, 2006.
Office Action received for U.S. Appl. No. 10/335,075, dated Aug. 10, 2005.
Office Action received for U.S. Appl. No. 10/335,075, dated Dec. 19, 2005.
Office Action received for U.S. Appl. No. 10/356,214, dated Apr. 29, 2009.
Office Action received for U.S. Appl. No. 10/356,214, dated Aug. 23, 2006.
Office Action received for U.S. Appl. No. 10/356,214, dated Feb. 13, 2007.
Office Action received for U.S. Appl. No. 10/356,214, dated Mar. 6, 2008.
Office Action received for U.S. Appl. No. 10/356,214, dated Nov. 4, 2008.
Office Action received for U.S. Appl. No. 10/356,214, dated Nov. 30, 2005.
Office Action received for U.S. Appl. No. 10/356,214, dated Sep. 12, 2007.
Office Action received for U.S. Appl. No. 10/435,104, dated Jun. 2, 2010.
Office Action received for U.S. Appl. No. 10/435,104, dated Jun. 10, 2004.
Office Action received for U.S. Appl. No. 10/435,104, dated May 16, 2006.
Office Action received for U.S. Appl. No. 10/455,768, dated Nov. 16, 2004.
Office Action received for U.S. Appl. No. 10/486,067, dated Jan. 10, 2006.
Office Action received for U.S. Appl. No. 10/486,070, dated Apr. 20, 2005.
Office Action received for U.S. Appl. No. 10/486,070, dated Aug. 10, 2005.
Office Action received for U.S. Appl. No. 10/517,004, dated Aug. 13, 2007.
Office Action received for U.S. Appl. No. 10/517,004, dated Jan. 30, 2008.
Office Action received for U.S. Appl. No. 10/519,778, dated Feb. 23, 2006.
Office Action received for U.S. Appl. No. 10/541,083, dated May 5, 2008.
Office Action received for U.S. Appl. No. 10/541,083, dated Oct. 16, 2007.
Office Action received for U.S. Appl. No. 10/541,083, dated Oct. 31, 2007.
Office Action received for U.S. Appl. No. 10/616,832, dated Jan. 22, 2008.
Office Action received for U.S. Appl. No. 10/616,832, dated Jul. 21, 2009.
Office Action received for U.S. Appl. No. 10/616,832, dated Jun. 30, 2006.
Office Action received for U.S. Appl. No. 10/616,832, dated May 29, 2007.
Office Action received for U.S. Appl. No. 10/616,832, dated Oct. 20, 2006.
Office Action received for U.S. Appl. No. 10/616,832, dated Sep. 17, 2008.
Office Action received for U.S. Appl. No. 10/617,090, dated Mar. 22, 2005.
Office Action received for U.S. Appl. No. 10/638,115, dated Feb. 7, 2008.
Office Action received for U.S. Appl. No. 10/638,115, dated Jan. 31, 2007.
Office Action received for U.S. Appl. No. 10/638,115, dated Oct. 29, 2008.
Office Action received for U.S. Appl. No. 10/638,115, dated Sep. 18, 2007.
Office Action received for U.S. Appl. No. 10/667,144, dated Dec. 5, 2007.
Office Action received for U.S. Appl. No. 10/667,144, dated Jun. 6, 2011.
Office Action received for U.S. Appl. No. 10/667,144, dated Jun. 22, 2010.
Office Action received for U.S. Appl. No. 10/667,144, dated Mar. 24, 2009.
Office Action received for U.S. Appl. No. 10/667,144, dated May 2, 2007.
Office Action received for U.S. Appl. No. 10/667,144, dated May 12, 2008.
Office Action received for U.S. Appl. No. 10/667,144, dated Nov. 19, 2007.
Office Action received for U.S. Appl. No. 14/023,428, dated Jul. 18, 2017.
Office Action received for U.S. Appl. No. 14/023,428, dated Jul. 27, 2015.
Office Action received for U.S. Appl. No. 14/023,428, dated Jun. 13, 2016.
Office Action received for U.S. Appl. No. 14/077,007, dated Jan. 29, 2016.
Office Action received for U.S. Appl. No. 14/077,007, dated Jul. 27, 2015.
Office Action received for U.S. Appl. No. 14/246,926, dated Aug. 5, 2015.
Office Action received for U.S. Appl. No. 14/246,926, dated Jun. 15, 2016.
Office Action received for U.S. Appl. No. 14/246,926, dated Nov. 23, 2015.
Office Action received for U.S. Appl. No. 14/246,973, dated Aug. 3, 2015.
Office Action received for U.S. Appl. No. 14/246,973, dated Jul. 7, 2016.
Office Action received for U.S. Appl. No. 14/246,973, dated Nov. 24, 2015.
Office Action received for U.S. Appl. No. 14/312,339, dated Aug. 28, 2017.
Office Action received for U.S. Appl. No. 14/312,339, dated Dec. 28, 2017.

(56) References Cited

OTHER PUBLICATIONS

Office Action received for U.S. Appl. No. 14/312,339, dated Jan. 22, 2016.
Office Action received for U.S. Appl. No. 14/312,339, dated Jan. 31, 2017.
Office Action received for U.S. Appl. No. 14/312,339, dated May 3, 2016.
Office Action received for U.S. Appl. No. 14/312,339, dated May 23, 2017.
Office Action received for U.S. Appl. No. 14/323,753, dated Nov. 3, 2015.
Office Action received for U.S. Appl. No. 14/466,576, dated Jul. 8, 2015.
Office Action received for U.S. Appl. No. 14/539,830, dated Jan. 29, 2016.
Office Action received for U.S. Appl. No. 14/539,830, dated Jul. 26, 2016.
Office Action received for U.S. Appl. No. 14/732,977, dated Sep. 26, 2017.
Office Action received for U.S. Appl. No. 14/839,658, dated Sep. 19, 2017.
Office Action received for U.S. Appl. No. 14/855,080, dated Apr. 2, 2018.
Office Action received for U.S. Appl. No. 14/855,080, dated Apr. 15, 2019.
Office Action received for U.S. Appl. No. 14/855,080, dated Sep. 21, 2018.
Office Action received for U.S. Appl. No. 14/928,950, dated Mar. 30, 2018.
Office Action received for U.S. Appl. No. 14/928,950, dated Sep. 26, 2017.
Office Action received for U.S. Appl. No. 15/056,281, dated Feb. 5, 2018.
Office Action received for U.S. Appl. No. 15/056,281, dated Jan. 14, 2019.
Office Action received for U.S. Appl. No. 15/056,281, dated Jun. 13, 2018.
Office Action received for U.S. Appl. No. 15/056,281, dated Sep. 19, 2018.
Office Action received for U.S. Appl. No. 15/069,230, dated Aug. 7, 2018.
Office Action received for U.S. Appl. No. 15/069,230, dated Feb. 15, 2018.
Office Action received for U.S. Appl. No. 15/069,230, dated Mar. 19, 2019.
Office Action received for U.S. Appl. No. 15/142,106, dated Feb. 13, 2019.
Office Action received for U.S. Appl. No. 15/142,106, dated Jun. 13, 2019.
Office Action received for U.S. Appl. No. 15/142,106, dated Sep. 7, 2018.
Office Action received for U.S. Appl. No. 15/149,784, dated May 11, 2017.
Office Action received for U.S. Appl. No. 15/222,397, dated Jan. 23, 2017.
Office Action received for U.S. Appl. No. 15/344,978, dated Dec. 10, 2018.
Office Action received for U.S. Appl. No. 15/356,028, dated Aug. 29, 2018.
Office Action received for U.S. Appl. No. 15/356,028, dated Feb. 22, 2018.
Office Action received for U.S. Appl. No. 15/419,335, dated Aug. 13, 2018.
Office Action received for U.S. Appl. No. 15/946,071, dated Mar. 25, 2020.
Office Action received for U.S. Appl. No. 15/976,425, dated Jun. 22, 2020.
Office Action received for U.S. Appl. No. 15/976,425, dated Mar. 6, 2020.
Office Action received for U.S. Pat. No. 6,632,238, dated Feb. 26, 2003.
Office Action received for U.S. Appl. No. 11/396,141, dated Aug. 21, 2013.
Office Action received for U.S. Appl. No. 10/667,144, dated Nov. 23, 2009.
Office Action received for U.S. Appl. No. 10/667,144, dated Sep. 19, 2006.
Office Action received for U.S. Appl. No. 10/669,313, dated Oct. 31, 2005.
Office Action received for U.S. Appl. No. 10/682,459, dated Apr. 2, 2008.
Office Action received for U.S. Appl. No. 10/682,459, dated Apr. 18, 2007.
Office Action received for U.S. Appl. No. 10/682,459, dated Apr. 28, 2010.
Office Action received for U.S. Appl. No. 10/682,459, dated Dec. 4, 2008.
Office Action received for U.S. Appl. No. 10/682,459, dated Dec. 23, 2009.
Office Action received for U.S. Appl. No. 10/682,459, dated Jun. 10, 2009.
Office Action received for U.S. Appl. No. 10/682,459, dated Oct. 12, 2010.
Office Action received for U.S. Appl. No. 10/682,459, dated Sep. 15, 2006.
Office Action received for U.S. Appl. No. 10/786,444, dated Apr. 17, 2007.
Office Action received for U.S. Appl. No. 10/786,444, dated Apr. 24, 2008.
Office Action received for U.S. Appl. No. 10/786,444, dated Aug. 31, 2007.
Office Action received for U.S. Appl. No. 10/786,444, dated Jan. 14, 2010.
Office Action received for U.S. Appl. No. 10/786,444, dated Jun. 18, 2009.
Office Action received for U.S. Appl. No. 10/786,444, dated Oct. 17, 2008.
Office Action received for U.S. Appl. No. 10/786,444, dated Oct. 30, 2006.
Office Action received for U.S. Appl. No. 10/787,073, dated Aug. 13, 2009.
Office Action received for U.S. Appl. No. 10/787,073, dated Feb. 22, 2008.
Office Action received for U.S. Appl. No. 10/787,073, dated Nov. 12, 2008.
Office Action received for U.S. Appl. No. 10/787,073, dated Nov. 30, 2006.
Office Action received for U.S. Appl. No. 10/787,073, dated Sep. 5, 2007.
Office Action received for U.S. Appl. No. 10/908,721, dated Aug. 10, 2007.
Office Action received for U.S. Appl. No. 10/908,721, dated Feb. 2, 2010.
Office Action received for U.S. Appl. No. 10/908,721, dated Jan. 25, 2008.
Office Action received for U.S. Appl. No. 10/908,721, dated Jun. 23, 2009.
Office Action received for U.S. Appl. No. 10/908,721, dated Nov. 25, 2008.
Office Action received for U.S. Appl. No. 10/908,721, dated Oct. 19, 2006.
Office Action received for U.S. Appl. No. 11/048,503, dated Jun. 26, 2009.
Office Action received for U.S. Appl. No. 11/048,503, dated Mar. 13, 2009.
Office Action received for U.S. Appl. No. 11/113,549, dated Apr. 16, 2008.
Office Action received for U.S. Appl. No. 11/113,549, dated Feb. 6, 2007.
Office Action received for U.S. Appl. No. 11/113,549, dated Jan. 4, 2011.

(56) References Cited

OTHER PUBLICATIONS

Office Action received for U.S. Appl. No. 11/113,549, dated Jul. 6, 2010.
Office Action received for U.S. Appl. No. 11/113,549, dated Jul. 21, 2009.
Office Action received for U.S. Appl. No. 11/113,549, dated May 30, 2007.
Office Action received for U.S. Appl. No. 11/113,549, dated Nov. 9, 2007.
Office Action received for U.S. Appl. No. 11/152,562, dated Feb. 13, 2009.
Office Action received for U.S. Appl. No. 11/152,562, dated Jul. 6, 2009.
Office Action received for U.S. Appl. No. 11/152,562, dated Mar. 31, 2010.
Office Action received for U.S. Appl. No. 11/152,562, dated May 13, 2008.
Office Action received for U.S. Appl. No. 11/198,811, dated Apr. 6, 2009.
Office Action received for U.S. Appl. No. 11/198,811, dated Aug. 26, 2008.
Office Action received for U.S. Appl. No. 11/198,811, dated Sep. 22, 2009.
Office Action received for U.S. Appl. No. 11/344,793, dated Jan. 22, 2009.
Office Action received for U.S. Appl. No. 11/344,868, dated Mar. 25, 2009.
Office Action received for U.S. Appl. No. 11/344,891, dated Apr. 29, 2008.
Office Action received for U.S. Appl. No. 11/344,891, dated Dec. 8, 2008.
Office Action received for U.S. Appl. No. 11/344,891, dated Feb. 26, 2009.
U.S. Appl. No. 11/508,656, filed Aug. 30, 2010, Office Action.
U.S. Appl. No. 11/508,656, mail date Mar. 25, 2010, Office Action.
U.S. Appl. No. 12/684,470, Jan. 21, 2016, Office Action.
U.S. Appl. No. 12/684,470, Jun. 4, 2014, Office Action.
U.S. Appl. No. 12/684,470, Mail Date Aug. 26, 2015, Office Action.
U.S. Appl. No. 13/308,227, Dec. 2, 2013, Interview Summary.
U.S. Appl. No. 13/615,547, Apr. 12, 2013, Notice of Allowance.
U.S. Appl. No. 14/928,950, Jun. 4, 2018, Interview Summary.
U.S. Appl. No. 29/230,479, Notices of Allowance, dated Aug. 24, 2006.
U.S. Application filed Apr. 30, 2008, by Ginn et al., U.S. Appl. No. 12/113,092.
U.S. Application filed Jan. 31, 2011, by Cariey et al., U.S. Appl. No. 13/017,636.
U.S. Application filed Jul. 5, 2000, by Kerievsky, U.S. Appl. No. 09/610,128.
U.S. Application filed May 25, 2001, by Ginn, U.S. Appl. No. 09/866,551.
U.S. Application filed Apr. 18, 2016, by Roorda et al., U.S. Appl. No. 15/131,786.
U.S. Application filed Apr. 20, 2006, by Jones et al., U.S. Appl. No. 60/793,444.
U.S. Application filed Aug. 24, 2005, by Sibbitt Jr. et al., U.S. Appl. No. 60/711,279.
U.S. Application filed Dec. 19, 2007, by Mackiewicz et al., U.S. Appl. No. 61/015,144.
U.S. Application filed Dec. 22, 2008, by Clark, U.S. Appl. No. 61/139,995.
U.S. Application filed Dec. 30, 2008, by Clark, U.S. Appl. No. 61/141,597.
U.S. Application filed Jan. 9, 2009, by Mehl et al., U.S. Appl. No. 61/143,748.
U.S. Application filed Jan. 9, 2009, by Voss et al., U.S. Appl. No. 61/143,751.
U.S. Application filed Jan. 16, 2009, by Fortson, et al., U.S. Appl. No. 61/145,468.
U.S. Application filed Jul. 1, 2005, by Pantages et al., U.S. Appl. No. 60/696,069.
U.S. Application filed Jun. 24, 2005, by Cady, U.S. Appl. No. 60/693,531.
U.S. Application filed Jun. 25, 2007, by Ellingwood et al., U.S. Appl. No. 60/946,042.
U.S. Application filed Jun. 25, 2007, by Ellingwood, U.S. Appl. No. 60/946,026.
U.S. Application filed Jun. 25, 2007, by Voss et al., U.S. Appl. No. 60/946,030.
U.S. Application filed Oct. 14, 2005, by Sibbitt Jr. et al., U.S. Appl. No. 60/726,985.
U.S. Application filed Oct. 30, 2008, by Mehl et al., U.S. Appl. No. 61/109,822.
U.S. Application filed Sep. 15, 2008, by Sibbitt Jr. et al., U.S. Appl. No. 61/097,072.
UT Aker et al, Immediate arterial hemostasis after cardiac cateterization: initial experience with a new puncture closure device, Cathet Cardiovasc Diagn, Mar. 1994, pp. 228-232, vol. 33—No. 3, Missouri Baptist Medical Center, St. Louis.
Watelet et al, Percutaneous repair of aortic aneurysms: a prospective study of suture-mediated closure devices, European journal of vascular and endovascular surgery, vol. 32, No. 3, 2006, p. 261-265.
Wei Qu et al, An absorbable pinned-ring device for microvascular anastomosis of vein grafts: Experimental studies, Microsurgery 1999, Mar. 1999, pp. 128-134, vol. 19—No. 3, Department of Orthopaedic Surgery, Hiroshima University School of Medicine, Hiroshima, Japan.
William G. Kussmaul III MD, et al., Rapid arterial hemostasis and decreased access site complications after cardiac catherization and angioplasty: Results of randomized trial of a novel hemostatic device, Journal of American College of Cardiology, Jun. 1995, pp. 1685-1692, vol. 25—No. 7.
Notice of Allowance received for U.S. Appl. No. 09/764,813, dated Jun. 4, 2001.
Notice of Allowance received for U.S. Appl. No. 09/933,299, dated Jun. 16, 2003.
Notice of Allowance received for U.S. Appl. No. 09/948,813, dated Jan. 31, 2003.
Notice of Allowance received for U.S. Appl. No. 09/949,398, dated Jul. 28, 2003.
Notice of Allowance received for U.S. Appl. No. 09/949,438, dated Apr. 21, 2003.
Notice of Allowance received for U.S. Appl. No. 10/006,400, dated Apr. 27, 2010.
Notice of Allowance received for U.S. Appl. No. 10/006,400, dated Aug. 2, 2010.
Notice of Allowance received for U.S. Appl. No. 10/006,400, dated Jan. 13, 2010.
Notice of Allowance received for U.S. Appl. No. 10/006,400, dated Jul. 9, 2009.
Notice of Allowance received for U.S. Appl. No. 10/081,717, dated Sep. 29, 2003.
Notice of Allowance received for U.S. Appl. No. 10/081,723, dated May 13, 2005.
Notice of Allowance received for U.S. Appl. No. 10/081,725, dated Feb. 9, 2004.
Notice of Allowance received for U.S. Appl. No. 10/081,726, dated Apr. 11, 2003.
Notice of Allowance received for U.S. Appl. No. 10/081,726, dated Jun. 9, 2003.
Notice of Allowance received for U.S. Appl. No. 10/147,774, dated Apr. 18, 2007.
Notice of Allowance received for U.S. Appl. No. 10/147,774, dated Dec. 2, 2010.
Notice of Allowance received for U.S. Appl. No. 10/147,774, dated Sep. 27, 2007.
Notice of Allowance received for U.S. Appl. No. 10/240,183, dated Mar. 9, 2005.
Notice of Allowance received for U.S. Appl. No. 10/264,306, dated Feb. 4, 2008.
Notice of Allowance received for U.S. Appl. No. 10/264,306, dated Jul. 2, 2007.

(56) References Cited

OTHER PUBLICATIONS

Notice of Allowance received for U.S. Appl. No. 10/264,306, dated May 10, 2006.
Notice of Allowance received for U.S. Appl. No. 10/264,306, dated Oct. 29, 2010.
Notice of Allowance received for U.S. Appl. No. 10/335,075, dated Dec. 27, 2006.
Notice of Allowance received for U.S. Appl. No. 10/356,214, dated Jan. 13, 2010.
Notice of Allowance received for U.S. Appl. No. 10/356,214, dated May 13, 2010.
Notice of Allowance received for U.S. Appl. No. 10/356,214, dated Sep. 3, 2010.
Notice of Allowance received for U.S. Appl. No. 10/435,104, dated Apr. 4, 2008.
Notice of Allowance received for U.S. Appl. No. 10/435,104, dated Aug. 2, 2007.
Notice of Allowance received for U.S. Appl. No. 10/435,104, dated Dec. 22, 2008.
Notice of Allowance received for U.S. Appl. No. 10/435,104, dated Dec. 28, 2006.
Notice of Allowance received for U.S. Appl. No. 10/435,104, dated Jan. 20, 2010.
Notice of Allowance received for U.S. Appl. No. 10/435,104, dated Jul. 10, 2007.
Notice of Allowance received for U.S. Appl. No. 10/435,104, dated Jul. 23, 2009.
Notice of Allowance received for U.S. Appl. No. 10/435,104, dated Nov. 14, 2007.
Notice of Allowance received for U.S. Appl. No. 10/435,104, dated Oct. 5, 2010.
Notice of Allowance received for U.S. Appl. No. 10/435,104, dated Oct. 26, 2007.
Notice of Allowance received for U.S. Appl. No. 10/435,104, dated Sep. 21, 2004.
Notice of Allowance received for U.S. Appl. No. 10/435,104, dated Sep. 26, 2008.
Notice of Allowance received for U.S. Appl. No. 10/455,768, dated Apr. 6, 2005.
Notice of Allowance received for U.S. Appl. No. 10/486,067, dated Sep. 20, 2006.
Notice of Allowance received for U.S. Appl. No. 10/486,070, dated Oct. 18, 2005.
Notice of Allowance received for U.S. Appl. No. 10/517,004, dated Apr. 23, 2010.
Notice of Allowance received for U.S. Appl. No. 10/517,004, dated Aug. 3, 2010.
Notice of Allowance received for U.S. Appl. No. 10/517,004, dated Aug. 13, 2008.
Notice of Allowance received for U.S. Appl. No. 10/517,004, dated Feb. 10, 2009.
Notice of Allowance received for U.S. Appl. No. 10/517,004, dated Jan. 11, 2010.
Notice of Allowance received for U.S. Appl. No. 10/517,004, dated Jun. 26, 2009.
Notice of Allowance received for U.S. Appl. No. 10/517,004, dated Mar. 24, 2009.
Thomas P. Baum RPA-C et al, Delayed Primary Closure Using Silastic Vessel and Skin Staples: Description of Technique and Case Reports, Annals of Plastic and Reconstructive Surgery, Albert Einstein College of Medicine and Montefiore Medical Center, Bronx, NY, Mar. 1999

* cited by examiner

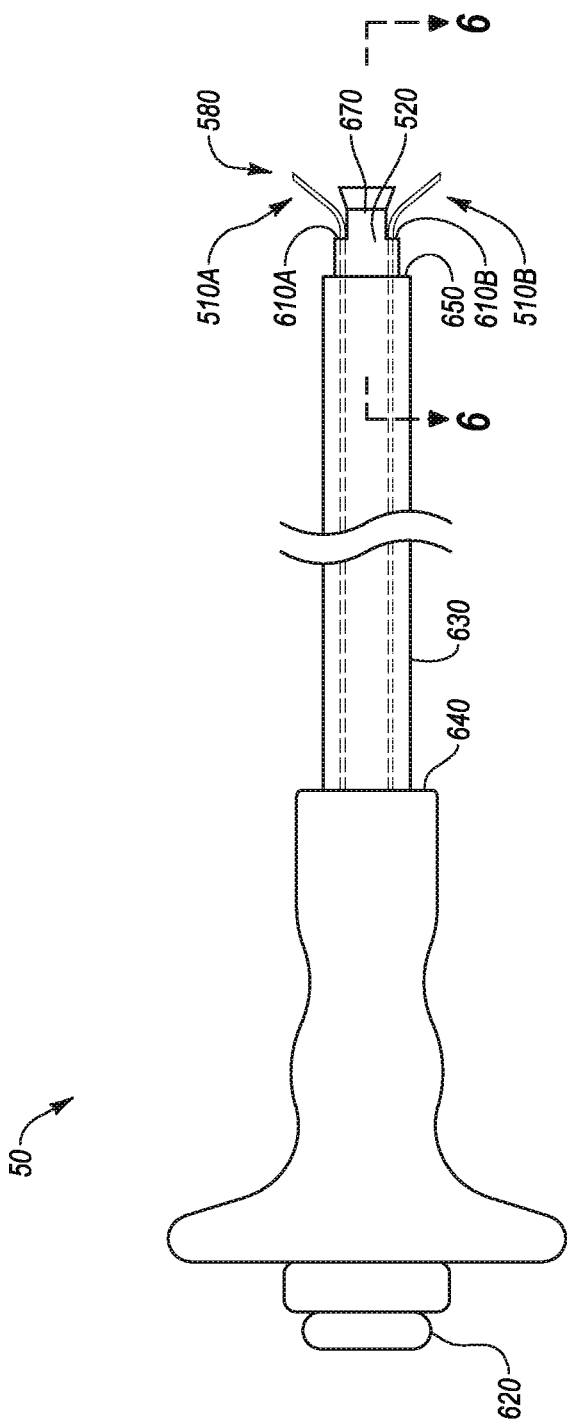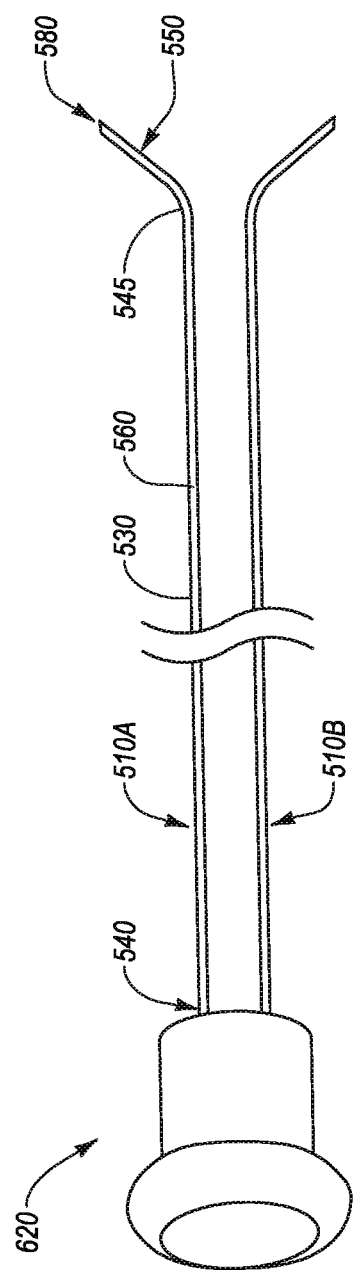
Fig. 7A
Fig. 7B

CLOSURE DEVICES AND METHODS

CROSS-REFERENCE TO RELATED APPLICATIONS

This application is a continuation of U.S. patent application Ser. No. 15/344,978, titled CLOSURE DEVICES AND METHODS, filed Nov. 7, 2016, which is a divisional of U.S. patent application Ser. No. 13/112,618, titled CLOSURE DEVICES AND METHODS, filed May 20, 2011, now U.S. Pat. No. 9,486,191, which is a continuation-in-part of U.S. patent application Ser. No. 12/684,470, titled CLOSURE DEVICES, SYSTEMS, AND METHODS, filed Jan. 8, 2010, now U.S. Pat. No. 9,414,820, which claims the benefit of U.S. Provisional Application No. 61/143,751, titled VESSEL CLOSURE DEVICES AND METHODS, filed Jan. 9, 2009, which are incorporated herein by reference in their entireties.

BACKGROUND

1. Technical Field

The present disclosure relates generally to medical devices and their methods of use. In particular, the present disclosure relates to vessel closure devices and corresponding methods of use.

2. The Technology

Catheterization and interventional procedures, such as angioplasty or stenting, generally are performed by inserting a hollow needle through a patient's skin and tissue into the vascular system. A guidewire may be advanced through the needle and into the patient's blood vessel accessed by the needle. The needle is then removed, enabling an introducer sheath to be advanced over the guidewire into the vessel, e.g., in conjunction with or subsequent to a dilator.

A catheter or other device may then be advanced through a lumen of the introducer sheath and over the guidewire into a position for performing a medical procedure. Thus, the introducer sheath may facilitate introducing various devices into the vessel, while minimizing trauma to the vessel wall and/or minimizing blood loss during a procedure.

Upon completing the procedure, the devices and introducer sheath are removed, leaving a puncture site in the vessel wall. Traditionally, external pressure would be applied to the puncture site until clotting and wound sealing occur; however, the patient must remain bedridden for a substantial period after clotting to ensure closure of the wound. This procedure may also be time consuming and expensive, requiring as much as an hour of a physician's or nurse's time. It is also uncomfortable for the patient and requires that the patient remain immobilized in the operating room, catheter lab, or holding area. In addition, a risk of hematoma exists from bleeding before hemostasis occurs. Although some closure systems may be available, they provide limited control and flexibility to the operator, which may lead to improper or undesirable closure of the puncture site.

BRIEF SUMMARY

The present invention provides a vessel closure device that is both manageable and versatile. A vessel closure device is provided that may include a guide member and one or more needle guides disposed at least partially within the guide member. The needle guides may be configured to move between a first position wherein the needle guides are substantially straightened at least partially within the guide member and a second position wherein the needle guides at least partially extend radially and distally away from the guide member. The vessel closure device may further include an angle adjustment member movably attached to the guide member. The angle adjustment member may be configured to move between a first position and a second position wherein the angle adjustment member can selectively deflect the needle guides radially toward the guide member when the needle guides are in the second position.

A vessel closure device is provided that may include a guide member and one or more needle guides moveably connected to the guide member. The needle guides may be configured to move between a first position wherein the needle guides are adjacent to the guide member and a second position wherein the needle guides at least partially extend distally away and radially outward from the guide member at a first angle. The vessel closure device may further include an angle adjustment member slidably attached to the guide member. The angle adjustment member may be configured to selectively reduce the first angle of the needle guides in the second position by selectively urging the needle guides toward the guide member.

A suture securing device is provided that may include an elongated body having a proximal end, a distal end, and an inner cavity. The elongated body may further include a first opening in the proximal end that is in communication with the inner cavity. The elongated body may further include a cutout extending distally from the first opening. The cutout may include tissue-engaging elements. The elongated body may be attached to a suture. The elongated body may be moveable between a first position wherein the elongated body is substantially parallel with a longitudinal axis of the suture and a second position wherein the elongated body is substantially non-parallel with the longitudinal axis of the suture and at least a portion of the suture is received within the cutout such that the elongated body can resist proximal movement against a distal surface of a vessel wall.

A suture securing device is provided that may include a body having a proximal end, a distal end, and an inner cavity. The body may further include a first opening in the proximal end and a second opening in the distal end, both in communication with the inner cavity. The body may further include elongated slots extending distally from the proximal end. The slots may define projections therebetween that have a fixed end connected to the body and a free end. The body may be attached to a suture extending through the inner cavity. The projections may be moveable between a first configuration wherein the projections are substantially parallel with a longitudinal axis of the body and a second configuration wherein the projections extend radially outwardly from the body such that the body can resist proximal movement against a distal surface of a vessel wall.

A vessel closure system is provided that may include a plurality of needle carriers having a distal end and a proximal end. The system may also include a plurality of detachable needles configured to resist proximal movement when deployed through a vessel wall. At least one of the detachable needles may be detachably coupled to the distal end of one of the needle carriers. The system may also include at least one suture secured to each of the detachable needles. A guide member can have a plurality of first lumens extending distally from a proximal end toward a distal end of the guide member. Each of the first lumens can be sized to receive one of the needle carriers and one of the detachable needles coupled to the needle carrier. The first lumens can also be configured to direct the needle carrier and the detachable needle radially outward and distally away from the guide member. The system may also include an outer housing that has a second lumen defined between a distal end and a proximal end of the outer housing. The second lumen can be configured to receive at least a portion of the guide member. The distal end of the outer housing may also include a tapered tip portion. The tapered tip portion can be configured to move between a first configuration and a second configuration. An anchor member can also be configured to be at least partially disposed within the second lumen. The anchor member can comprise an anchor portion and an elongate portion. The anchor member can be disposed in the inner lumen in an initial configuration and move to an expanded configuration once positioned distally from the distal end of the outer housing. Finally, the system may include an expandable plug positioned between the guide member and the anchor member.

A method of closing a puncture in a vessel wall is provided that may include advancing a guide member into proximity with a puncture in a vessel wall, the guide member having openings near a distal end a plurality of needle guides disposed within. A distal end of an angle adjustment member, slidably coupled to the guide member, may then be positioned distal to the openings of the guide member. The needle guides and sutures and suture securing devices disposed within the needle guides may then be deployed distally and radially away from the guide member. The angle adjustment member may then deflect the needle guides toward a longitudinal axis of the guide member. The deflected needle guides and suture securing devices may then be advanced through the vessel wall. Thereafter, the needle guides may be retracted into the guide member to release the suture securing devices. Tension may then be established in the sutures to move the suture securing devices toward each other to thereby close the puncture.

These and other advantages and features of the present disclosure will become more fully apparent from the following description and appended claims, or may be learned by the practice of the disclosure as set forth hereinafter.

BRIEF DESCRIPTION OF THE DRAWINGS

To further clarify at least some of the advantages and features of the present disclosure, a more particular description of the disclosure will be rendered by reference to specific embodiments thereof which are illustrated in the appended drawings. It is appreciated that these drawings depict only illustrated embodiments of the disclosure and are therefore not to be considered limiting of its scope. The disclosure will be described and explained with additional specificity and detail through the use of the accompanying drawings in which:

FIG. 7A illustrates a side view of a closure device according to one example;

FIG. 7B illustrates a perspective view of needle guides removed from the closure device shown in FIG. 7A;

Figure 1A:
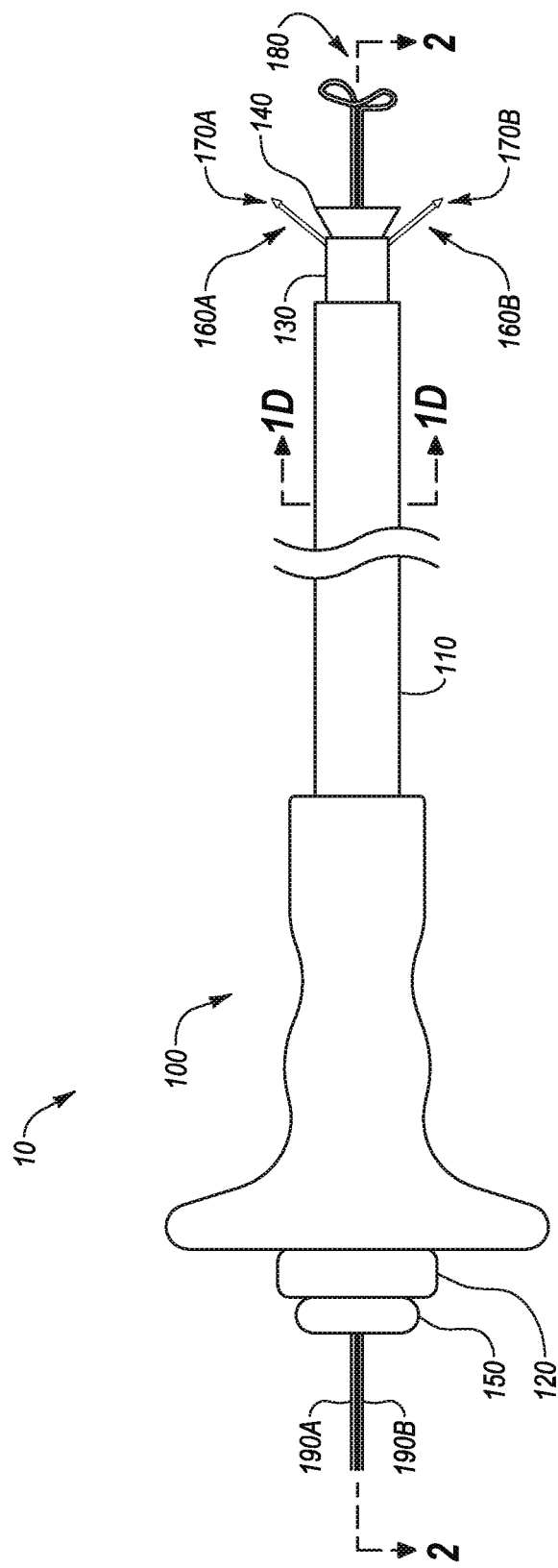
FIG. 1A illustrates a side view of a closure device according to one example.

It should be noted that the figures are not drawn to scale and that elements of similar structures or functions are generally represented by like reference numerals for illustrative purposes throughout the figures. It also should be noted that the figures are only intended to facilitate the description of example configurations of the present disclosure.

DETAILED DESCRIPTION

The present disclosure relates to devices and methods for closing an opening in a body lumen. In one example embodiment, a closure device of the present disclosure may allow an operator to quickly and efficiently close a body lumen opening or puncture in a vessel wall while simultaneously providing the operator with a greater measure of control and flexibility in positioning and anchoring the closure device than previously available. For example, the closure device may allow an operator to achieve a more intimate securement of a suture securing device in the tissue surrounding a body lumen opening. In a further embodiment, the closure device may be compatible with a wider range of body lumen wall thicknesses, thereby taking into account the possibility of calcifications or scar tissue in the lumen wall. In yet a further embodiment, the closure device may be compatible with varying sizes of body lumen openings.

FIG. 1A illustrates a side view of a closure device 10 according to one example. The closure device 10 may include a handle 100, an outer housing 110, a first plunger 120 coupled to a guide member 130, an optional plug 140, a second plunger 150 coupled to a plurality of needle carriers 160A, 160B, a plurality of detachable needles 170A, 170B removably coupled to the needle carriers 160A, 160B respectively, an anchor member 180 and control members 190A, 190B coupled to the anchor member 180.

The anchor member 180 and control members 190A, 190B may cooperate to allow the closure device 10 to be located relative to a puncture in a vessel wall, such as an arteriotomy. Any type of locator having any configuration may be used as desired to position the closure device 10 in proximity to a vessel wall.

In the illustrated example, the control members 190A, 190B can be manipulated to move the anchor member 180 between a pre-deployed state (not shown in FIG. 1A) to the expanded or deployed state shown in FIG. 1A. In particular, the control members 190A, 190B may be coupled to the anchor member 180 and extend proximally from the anchor member 180 through the plug 140, the guide member 130, the first plunger 120, and the second plunger 150. In the illustrated example, manipulation of the control members 190A, 190B may be performed manually, though it will be appreciated that any suitable device and/or method may be used to manipulate the control members 190A, 190B.

Figure 1B:
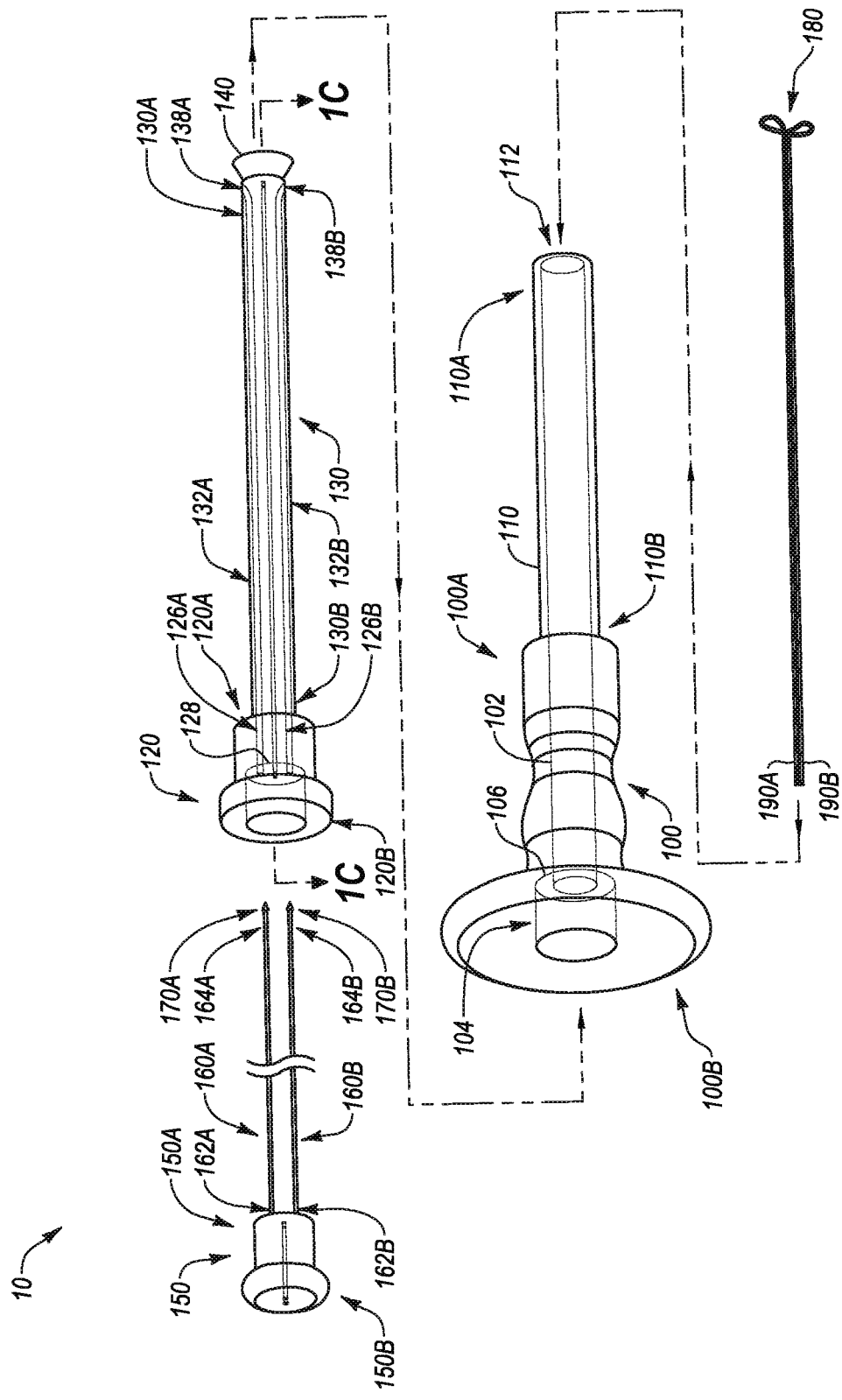
FIG. 1B illustrates an exploded view of the closure device of FIG. 1A.

As shown in FIG. 1B, the control members 190A, 190B and the anchor member 180 may form a continuous member. In such an example, retracting the control members 190A, 190B may anchor the anchor member 180 against an inner surface of a vessel wall or any other surface against which the anchor member 180 is positioned. In one embodiment, retracting both control members 190A, 190B simultaneously may produce tension or some other force in the anchor member 180 which may increase the resistance of the anchor member 180 to contracting.

For example, the tension of both control members 190A, 190B may be simultaneously transferred to the anchor member 180 thereby creating sufficient tension in the anchor member 180 to resist movement away from its expanded configuration. In addition, providing an opposing force against a proximal surface of the anchor member 180, such as with a vessel wall, may also assist in creating sufficient tension in the anchor member 180 to resist contraction of the anchor member 180. In a further implementation, the wires of the anchor member 180 may overlap or cross over each other in order to increase resistance.

In at least one example, retracting only one of the control members 190A, 190B, may lessen the tension in the anchor member 180, thereby allowing the anchor member 180 to move from its deployed, expanded configuration to a contracted configuration. As a result, by retracting only one of the control members 190A or 190B, without applying tension to the other control member 190B or 190A or by applying a distal force to the other control member 190B or 190A, the anchor member 180 may contract and be retracted into the outer housing 110.

Referring again to FIG. 1A, the guide member 130 may be configured to house at least a portion of the control members 190A, 190B and to allow axial movement of the control members 190A, 190B relative to the guide member 130. Such a configuration may allow the control members 190A, 190B to be manipulated at a proximal location to control the anchor member 180 at a distal location.

The guide member 130, and thus the control members 190A, 190B that extend therethrough, may be at least partially housed within the outer housing 110 and/or within the handle 100. As previously discussed, the guide member 130 may be coupled to the first plunger 120. Such a configuration may cause actuation of the first plunger 120 to result in axial movement of the guide member 130. In at least one example, axial movement of the first plunger 120 results in similar axial movement of the guide member 130. Such a configuration may allow the first plunger 120 to extend and retract the guide member 130 from the outer housing 110 as desired. While actuation of the first plunger 120 may have been described with reference to axial movement of the first plunger 120 relative to the handle 100, it will be appreciated that actuation of the first plunger 120 may include any type of action that results in desired movement of the guide member 130.

The optional plug 140 may be secured to the distal end of the guide member 130 in such a manner that axial movement of the first plunger 120 also results in a corresponding movement of the plug 140. Such a configuration may thereby allow axial movement of the first plunger 120 to also extend and retract the plug 140 from the outer housing 110 as desired by extending and retracting the guide member 130. Although the guide member 130 and the plug 140 are shown as moving together, it will be appreciated that the plug 140 may also be independently controlled and moved, such as by the use of additional plungers and/or shafts.

In addition to serving as a mandrel to thereby move the plug, the guide member 130 may also be configured to house the needle carriers 160A, 160B and the detachable needles 170A, 170B. More specifically, the guide member 130 may be configured to allow the needle carriers 160A, 160B and the detachable needles 170A, 170B to move between a pre-deployed state (not shown in FIG. 1A) and the deployed state shown in FIG. 1A. In a pre-deployed state (not shown in FIG. 1A), the needle carriers 160A, 160B and/or the detachable needles 170A, 170B are retracted within the guide member 130. In the deployed state shown in FIG. 1A, the detachable needles 170A, 170B and/or the needle carriers 160A, 160B extend radially and/or distally from the guide member 130.

The needle carriers 160A, 160B are coupled to the second plunger 150 in such a way that actuation of the second plunger 150 causes the needle carriers 160A, 160B to move between the pre-deployed and deployed states described above. In at least one example, axial movement of the second plunger 150 relative to the first plunger 120 moves the needle carriers 160A, 160B between the pre-deployed and deployed states. While actuation of the second plunger 150 may be provided by axial movement of the second plunger 150 relative to the first plunger 120, it will be appreciated that actuation of the second plunger 150 may include any type of action that results in desired movement of the needle carriers 160A, 160B.

As will be described in more detail, the actions described above allow the closure device 10 to deploy the detachable needles 170A, 170B into a vessel wall as part of a method for closing a puncture in the vessel wall. Exemplary structure of each of the components introduced above will first be introduced briefly followed by a discussion of the assembly and interaction of adjacent components. Thereafter, function of an exemplary closure device will be discussed, followed by a discussion of an exemplary method of closing a puncture in a vessel wall.

FIG. 1B illustrates an exploded view of the closure device 10. As illustrated in FIG. 1B, the handle 100 includes a distal end 100A and a proximal end 100B. A guide member receiving lumen 102 extends proximally from the distal end 100A. A first plunger receiving lumen 104 extends distally from the proximal end 100B and is in communication with the guide member receiving lumen 102. In the illustrated example, a shoulder 106 is formed at a transition between the guide member receiving lumen 102 and the first plunger receiving lumen 104.

The outer housing 110 may be coupled to the distal end 100A of the handle 100. In particular, the outer housing 110 may include a distal end 110A and a proximal end 110B. A guide member receiving lumen 112 may be formed therein that extends through the distal end 110A and the proximal end 110B. The guide member receiving lumen 112 may be configured to allow the guide member 130 to move axially within the outer housing 110 as will be described in more detail hereinafter. In at least one example, the guide member receiving lumen 112 may have approximately the same size as the guide member receiving lumen 102 defined in the handle 102.

As shown in FIG. 1B, the proximal end 110B of the outer housing 110A may be coupled to the distal end 100A of the handle 100 in such a manner that the guide member receiving lumens 102, 112 are aligned to thereby form a single lumen that is in communication with the distal end 110A of the outer housing 110 and the first plunger receiving lumen 104 in the handle 100. Such a configuration may allow the first plunger 120 to move axially relative to the handle 100 while moving the guide member 130 axially relative to outer housing 110 and the handle 100.

More specifically, the first plunger 120 may include a distal end 120A and a proximal end 120B. The distal end 120A may be sized to fit within the first plunger receiving lumen 104. In the example shown, proximal translation of the first plunger 120 relative to the handle 100 may be limited by engagement between the distal end 120A of the first plunger 120 and the shoulder 106 in the handle 100.

As previously introduced, the first plunger 120 may be coupled to the guide member 130. In particular, the distal end 120A of the first plunger 120 may be coupled to a proximal end 130B of the guide member 130. Accordingly, as the first plunger 120 moves proximally relative to the handle 100, the proximal end 130B of the guide member 130 also moves proximally relative to the handle 100 as well as to the outer housing 110. In at least one example, axial movement of the proximal end 130B of the guide member 130 results in a proportional or similar movement of a distal end 130A. This may allow an operator to move the first plunger 120 axially to cause the distal end 130A of the guide member 130 to move between a first position, in which the distal end 130A is retracted within the distal end 110A of the outer housing 110, and various other positions, in which the distal end 130A extends beyond the distal end 110A of the outer housing 110 to varying extents. The distal end 130A of the guide member 130 can be extended distally beyond the distal end 110A of the outer housing 110 to deploy the plug 140 and/or position the needle carriers 160A, 160B for deployment. Deployment of the plug 140 will first be discussed, followed by a discussion of the deployment of the needle carriers 160A, 160B.

As previously introduced, the plug 140 may be coupled to the distal end of the guide member 130. As a result, the plug 140 may be retracted within and extended from the distal end 110A of the outer housing 110 by axial movement of the first plunger 120.

In at least one example, the plug 140 may be formed of an expandable material. Suitable materials can include, without limitation, collagen and/or one or more polymers such as PEG. When the plug 140 is moved out of the outer housing 110, the plug 140 may move toward an expanded state. Similarly, when the plug 140 is retracted back into the outer housing 110, the plug 140 may be compressed to fit within the outer housing 110. Accordingly, the distal end 130A of the guide member 130 can be extended beyond the distal end 110A of the outer housing 110 to deploy the plug 140 and/or retracted within the outer housing 110 to retrieve the plug 140.

The distal end 130A of the guide member 130 can also be extended beyond the distal end 110A to allow for deployment of the needle carrier 160A, 160B. In particular, relative movement between the second plunger 150 and the first plunger 120 may move the needle carriers 160A, 160B between retracted and extended positions relative to the guide member 130. The configuration of the guide member 130 will first be discussed in more detail, followed by a discussion of the interaction of the guide member 130 and the needle carriers 160A, 160B.

Figure 1C:
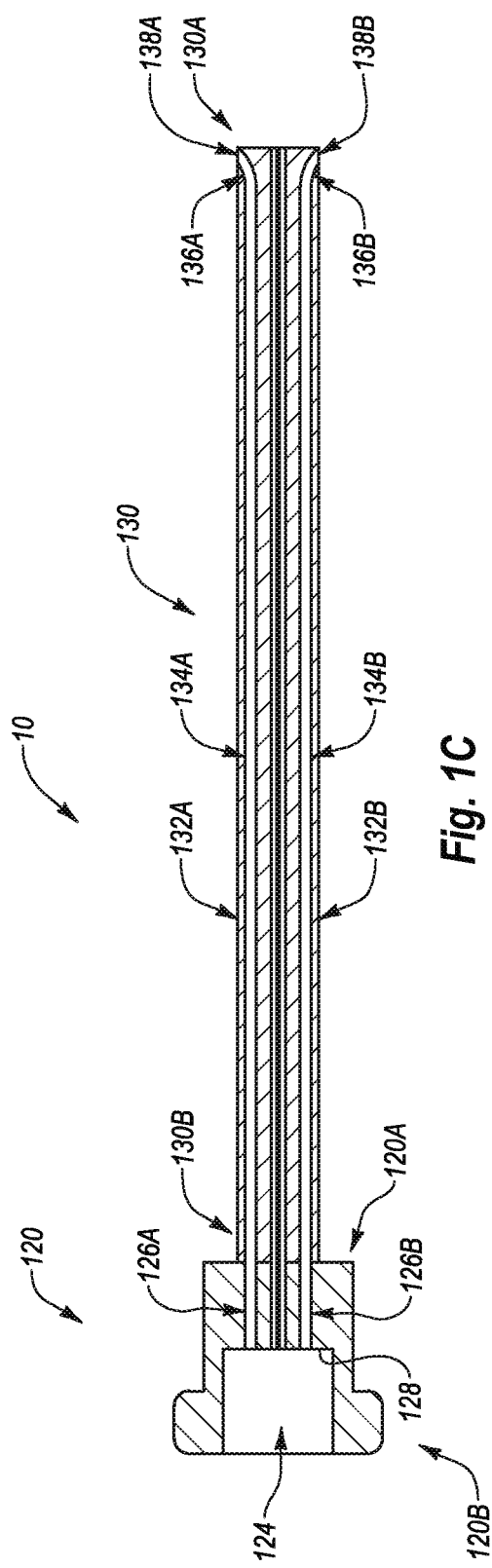
FIG. 1C illustrates a cross-sectional view of the guide member and associated first plunger of FIG. 1B taken along section 1C-1C of FIG. 1B.

FIG. 1C illustrates a cross-sectional view of the first plunger 120 and the guide member 130. As shown in FIG. 1C, the first plunger 120 has a second plunger receiving recess 124 defined therein that extends distally from a proximal end 120B. The first plunger 120 also has needle carrier lumens 126A, 126B defined therein that extend proximally from the distal end 120A and into communication with the second plunger receiving recess 124. A shoulder 128 is formed at a junction of the needle carrier lumens 126A, 126B and the second plunger receiving recess 124.

The guide member 130 may also have needle carrier lumens 132A, 132B defined therein that extend distally from the proximal end 130B. In the illustrated example, the needle carrier lumens 132A, 132B include parallel or axially aligned portions 134A, 134B and curved, angled portions 136A, 136B that are in communication with openings 138A, 138B in the guide member 130. The axially aligned portions 134A, 134B are aligned with the needle carrier lumens 126A, 126B defined in the first plunger 120 to thereby form continuous lumens that extend from near the distal end 130A of the guide member 130 to the second plunger receiving recess 124 in the first plunger member 120. The configuration of the guide member 130 can allow the guide member 130 to house the needle carriers 160A, 160B (FIG. 1B) therein prior to deployment and to guide the needle carriers 160A, 160B radially outward and distally away from the guide member 130. An exemplary configuration of the needle carriers 160A, 160B will first be discussed, followed by the interaction between the needle carriers 160A, 160B and the guide member 130 with reference to FIG. 1B.

As shown in FIG. 1B, proximal ends 162A, 162B of the needle carriers 160A, 160B may be coupled to a distal end 150A of the second plunger 150 in such a way that axial movement of the second plunger 150 results in similar movement of the needle carriers 160A, 160B, including distal ends 164A, 164B. As a result, when the second plunger 150 is positioned at least partially within the second plunger receiving lumen 124, the needle carriers 160A, 160B extend through the first plunger 120 by way of the needle carrier lumens 126A, 126B and into the guide member 130 by way of needle carrier lumens 132A, 132B.

The distal ends 164A, 164B of the needle carriers 160A, 160B may be positioned such that axial movement of the second plunger 150 relative to the first plunger 120 moves the needle carriers 160A, 160B between retracted and extended positions relative to the guide member 130. When the needle carriers 160A, 160B are retracted, the distal ends 164A, 164B of the needle carriers 160A, 160B may be positioned proximally and/or radially inward relative to the openings 138A, 138B. When the needle carriers 160A, 160B are extended, the distal ends 164A, 164B extend both radially outward and distally away from the openings 138A, 138B in the guide member 130. Accordingly, the guide member 130 is configured to house the needle carriers 160A, 160B and to guide the needle carriers 160A, 160B between the retracted and extended positions described above.

Figure 1D:
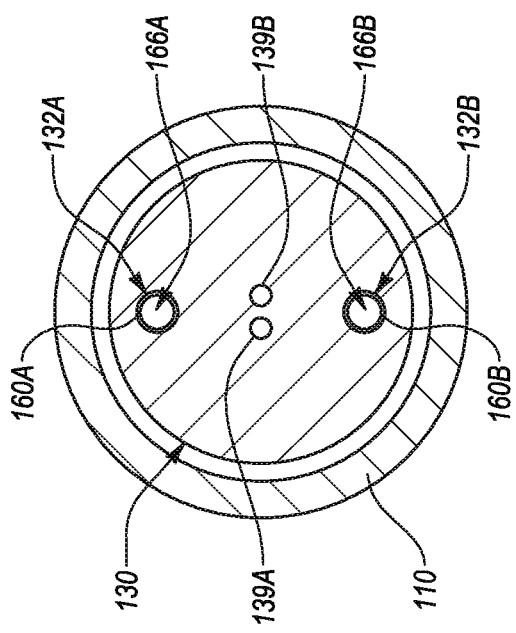
FIG. 1D illustrates a cross-sectional view of the closure device shown in FIG. 1A taken along section 1D-1D of FIG. 1A.

In at least one example, guide member 130 can be used to initially position the anchor member 180. Further, the guide member 130 may be configured to house the control members 190A, 190B in addition to the needle carriers 160A, 160B. FIG. 1D illustrates a cross-sectional view of the closure device 10 taken along section 1D-1D of FIG. 1A. As shown in FIG. 1D, the control member lumens 139A, 139B may be defined in the guide member 139A, 139B to pass through the guide member 130. The control member lumens 139A, 139B may be positioned at any location and orientation desired. FIG. 1D also illustrates that the needle carriers 160A, 160B may have suture lumens 166A, 166B defined therein. The suture lumens 166A, 166B may house sutures (not shown), which may be coupled to the detachable needles 170A, 170B (FIG. 1B). As will be discussed in more detail below, the closure device 10 may be configured to deploy the detachable needles 170A, 170B (FIG. 1B) through a vessel wall as part of a method for closing a puncture in a vessel wall. The function of the closure device 10 will first be described in isolation, followed by a discussion of the method for closing a puncture in a vessel wall using the closure device.

Figure 2A:
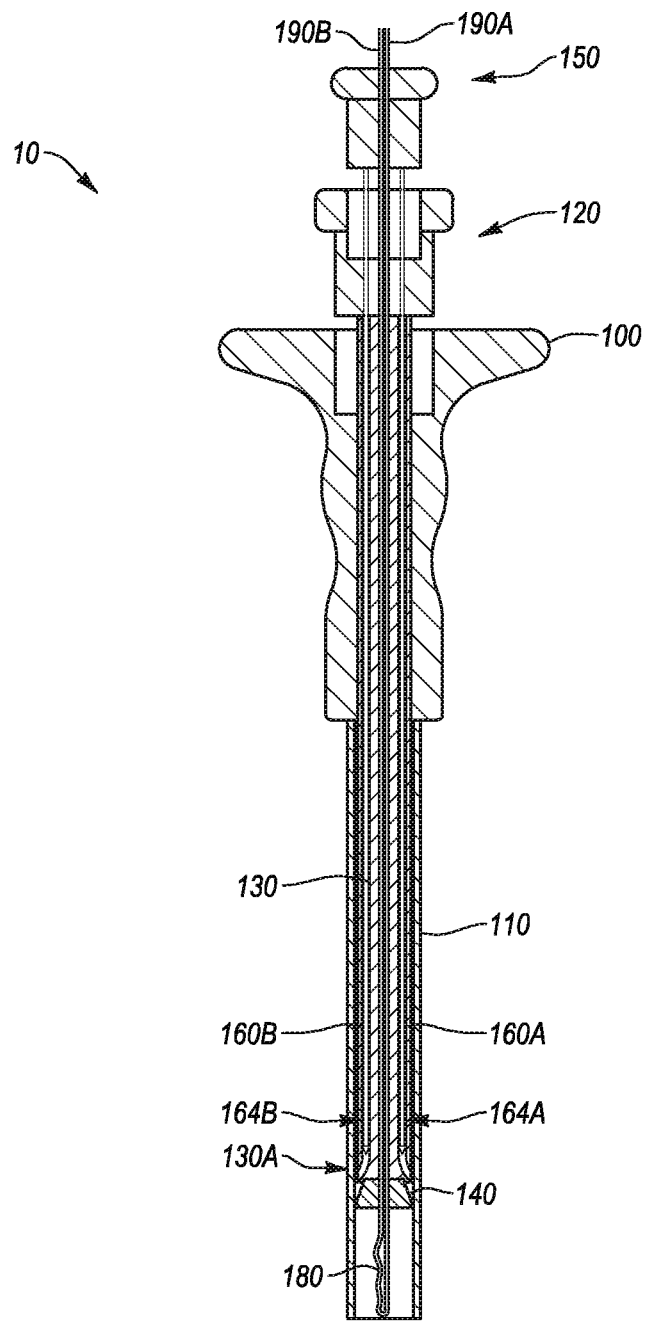
FIG. 2A illustrates a closure device in a pre-deployed state according to one example.
Figure 2B:
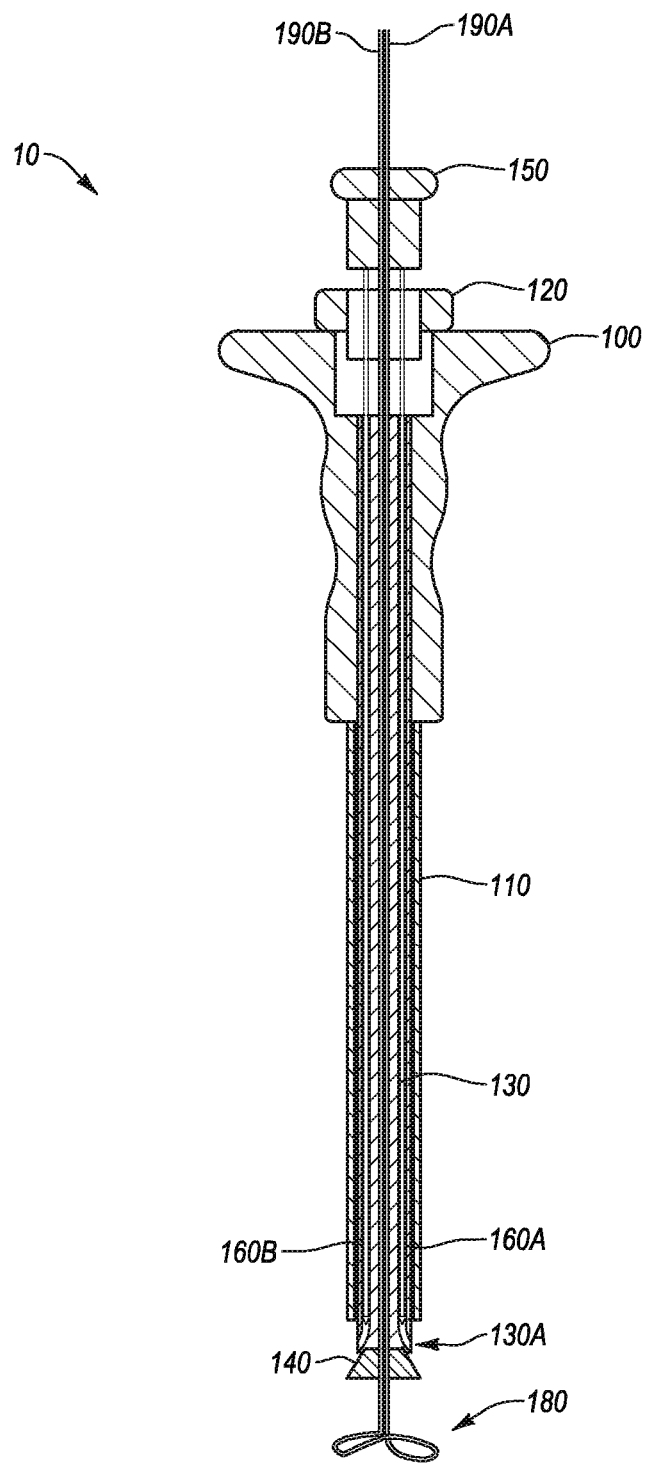
FIG. 2B illustrates the closure device of FIG. 2A in an intermediate state according to one example.
Figure 2C:
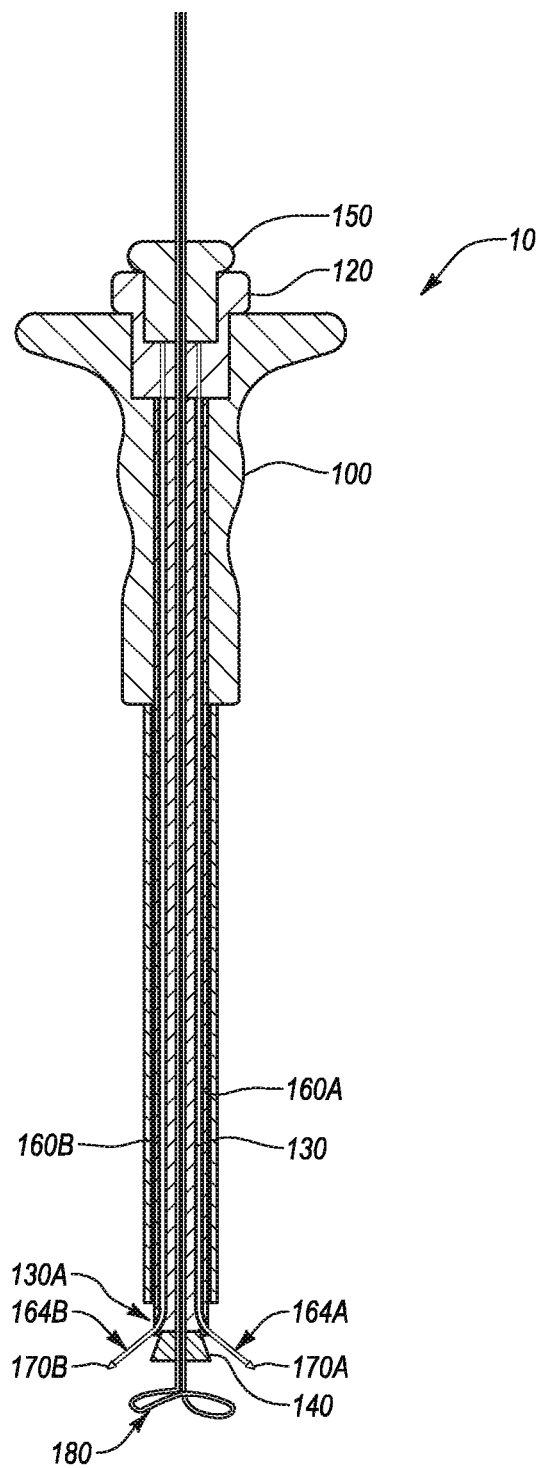
FIG. 2C illustrates the closure device of FIGS. 2A-2B in a deployed state.

FIGS. 2A-2C are cross-sectional views of the closure device 10 at various positions taken along section 2-2 of FIG. 1A. In particular, FIG. 2C is a cross-section view of the closure device 10 in the deployed state shown in FIG. 1A while FIGS. 2A and 2B show the closure device in a pre-deployed state and a location state according to one example. For ease of reference, various components will be described in which one component is being moved toward a second component. It will be appreciated that a second member can also be moved toward the first member or some combination of movement of the two can also be used to accomplish the same function.

As shown in FIG. 2A, while in a pre-deployed state the first plunger 120 is drawn proximally from the handle 100 to thereby position the distal end 130A of the guide member 130 as well as the plug 140 within the outer housing 110. While the plug 140 is thus positioned within the outer housing 110, the plug 140 may be compressed (FIG. 1B). Further, the second plunger 150 may be positioned proximally from the first plunger 120 to thereby position the distal ends 160A, 160B of the needle carriers 160A, 160B within the guide member 130. As also shown in FIG. 2A, the control members 190A, 190B may be manipulated and positioned to move the anchor member 180 to a pre-deployed position within the outer housing 110.

The closure device 10 may be moved from the pre-deployed state shown in FIG. 2A to the locator state shown in FIG. 2B by manipulating the control members 190A, 190B and moving the first plunger 120 toward the handle 100. In at least one example the second plunger 150 may move with the first plunger 120 as the first plunger 120 moves toward the handle 100. Such a configuration may allow the second plunger 150 to deploy the needle carriers 160A, 160B separately from movement of the first plunger 120.

As shown in FIG. 2B, as the first plunger 120 moves toward the handle 100, the anchor member 180, the plug 140 and/or the distal end 130A of the guide member 130 move distally from the distal end of the outer housing 110. The anchor member 180 may then be manipulated by the control members 190A, 190B to move to the deployed state shown in FIG. 2B.

More specifically, the anchor member 180 may be configured to move from an initial, contracted configuration within the outer housing 110 to a deployed, expanded configuration once deployed from the outer housing 110. To facilitate movement from an initial, contracted configuration to a deployed, expanded configuration, the anchor member 180 may include one or more superelastic or shape memory materials such as shape memory alloys.

For example, the anchor member 180 may be heat set in a deployed, expanded configuration. The anchor member 180 may then be elastically deformed into an initial, contracted configuration contracted and disposed within the outer housing 110. In its initial, contracted configuration shown in FIG. 2A, the anchor member 180 may store sufficient energy to return to its deployed, expanded configuration once released from the outer housing 110 shown in FIG. 2B.

Retracting the handle 100 in a proximal direction may position and/or anchor the anchor member 180 against a distal or inner surface of a vessel wall. In a further embodiment, further retracting the plunger member 130 in a proximal direction may retract the anchor member 180 from the vessel and/or into the outer housing 110.

Once the anchor member 180 is at a desired position, the first plunger 120 can be moved toward the handle 100 while holding the control members 190A, 190B stationary to thereby the advance the plug 140 toward the anchor member 180. The plug 140, which may have expanded from the compressed state described above upon exiting the outer housing 110, can thus be positioned relative to the anchor member 180. Such a configuration can allow the closure device 10 to engage a proximal or outer surface of the vessel's walls of varying thicknesses as the plug 140 can be advanced until it engages a vessel wall since the anchor member 180 is positioned on an opposing side of the vessel wall. Such a configuration can also place the distal end 130A of the guide member 130 in position to deploy the needle carriers 160A, 160B.

As shown in FIG. 2C, the needle carriers 160A, 160B can be deployed by moving the second plunger 150 toward the first plunger 120. As the second plunger 150 moves toward the first plunger 120, the needle carriers 160A, 160B, and the distal ends 164A, 164B in particular, move the detachable needles 170A, 170B distally and radially away from the distal end 130A of the guide member 130. Such a configuration can allow the detachable needles 170A, 170B to be moved into engagement with a vessel wall, as part of an exemplary method for closing a puncture in a vessel wall, which will now be discussed in more detail with reference to FIG. 3A-3D.

Figure 3A:
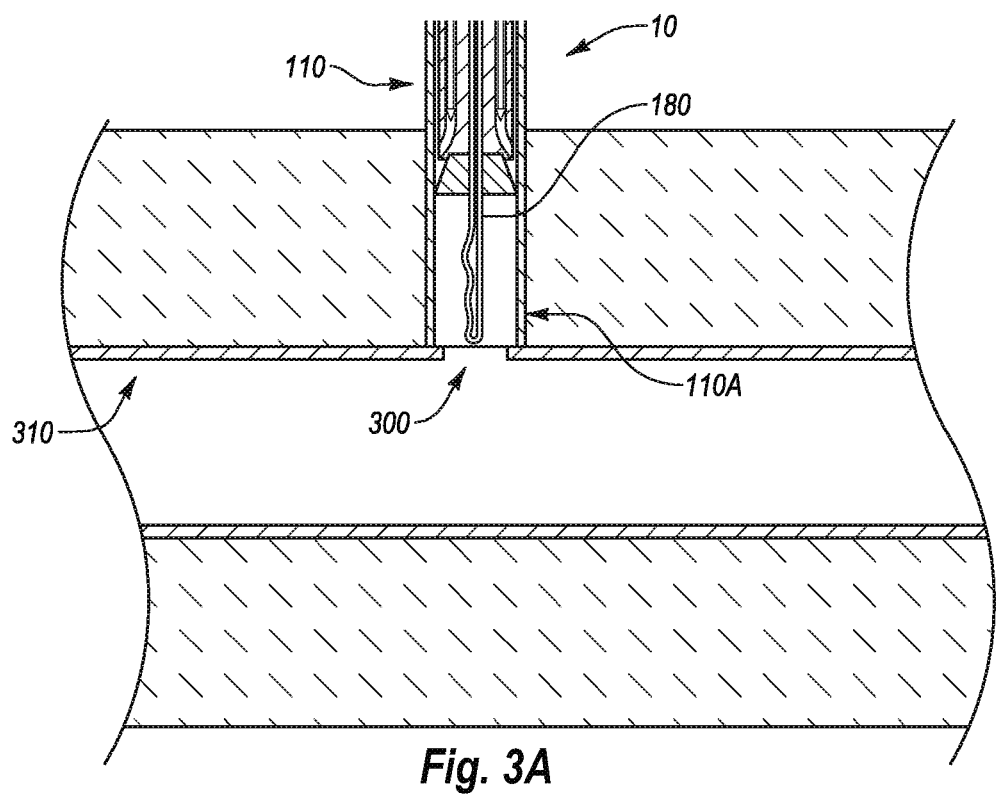
FIG. 3A illustrates steps for closing a puncture in a vessel wall in which a closure device is in a pre-deployed state and in proximity to an arteriotomy according to one example.

FIG. 3A illustrates first steps of a method for closing a puncture 300 in a vessel wall 310. For ease of reference, only the distal portion of the closure device 10 is shown and described. It will be appreciated that the distal components can be manipulated by proximal components in a similar manner as described above with reference to FIGS. 1A-2C.

Figure 3B:
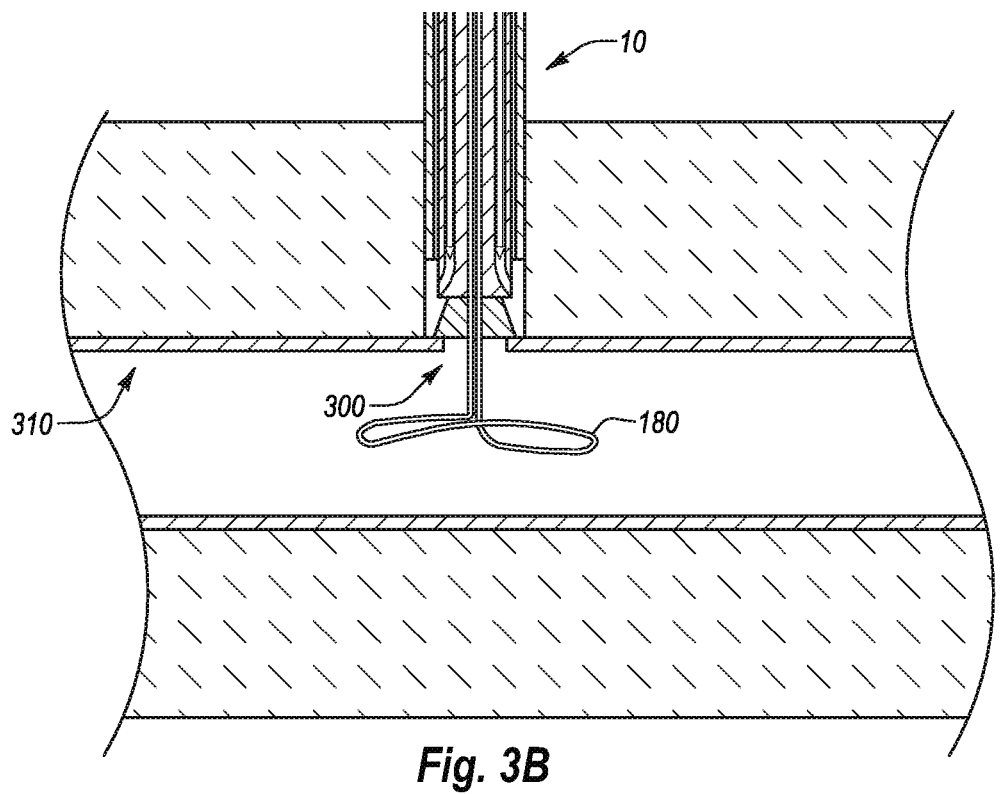
FIG. 3B illustrates steps for closing a puncture in a vessel wall in which the closure device of FIG. 3A is located relative to a vessel wall.

Referring now to FIG. 3A, the method can begin by positioning a distal end 110A of the outer housing 110 in proximity with the puncture 300 while the closure device 10 is in a pre-deployed state. With the distal end 110A of the outer housing 110 in proximity with the puncture 300, the anchor member 180 can be passed through the puncture 300 and moved to the deployed, expanded position as shown in FIG. 3B.

Figure 3C:
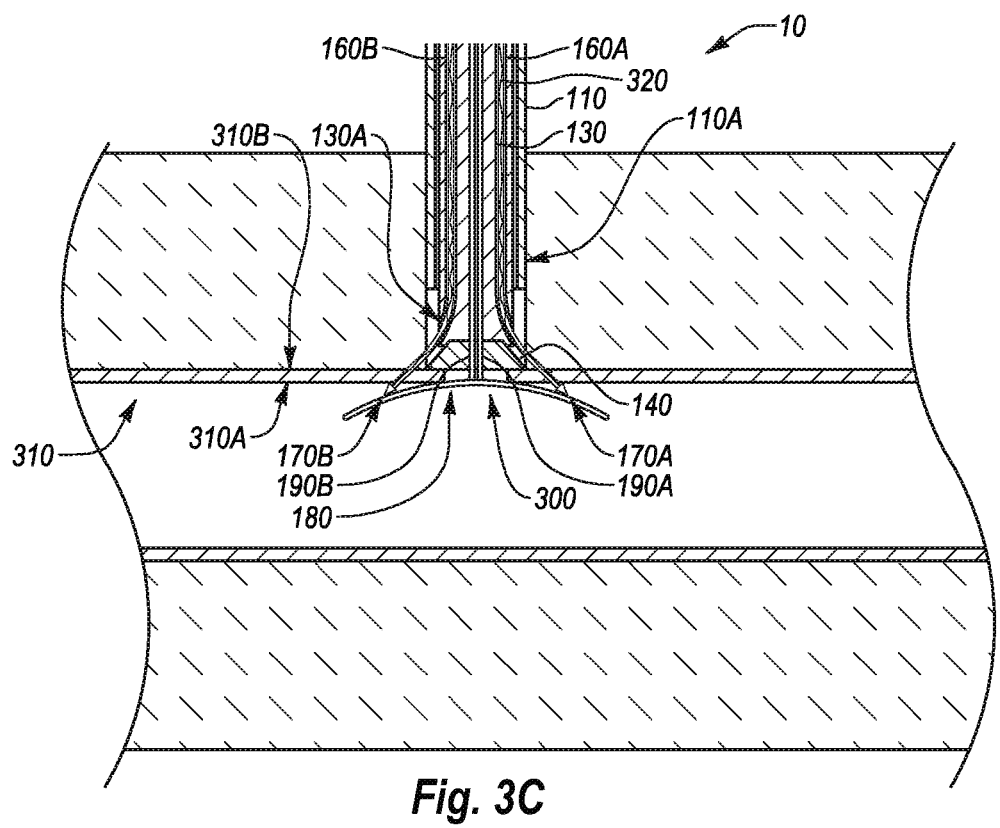
FIG. 3C illustrates steps for closing a puncture in a vessel wall in which detachable needles are deployed through the vessel wall.

As shown in FIG. 3C, the anchor member 180 can then be drawn proximally into engagement with an inner surface or posterior side 310A of the vessel wall 310 adjacent the puncture 300 and the distal end 130A of the guide member 130 can be urged distally toward the outer surface or anterior side 310B of the vessel wall 310, thereby positioning the vessel wall 310 adjacent the puncture 300 between the plug 140 and the anchor member 180. With the vessel wall 310 positioned between the anchor member 180 and the plug 140, the vessel wall 310 can be described as being located by the closure device 10 since the position of vessel wall 310 is established as being between the plug 140 and the anchor member 180. In at least one example, the expanded plug 140 can cover the puncture 300 while pressure between the plug 140 and the anchor member can provide sufficient contact between the plug 140 and the vessel wall 310 to limit the flow of fluid from the puncture 300.

As also shown in FIG. 3C, when the guide member 130 is in position with respect to the vessel wall 310, the distal end 130A of the guide member 130 can be positioned distally of the distal end 110A of the outer housing 110 to thereby expose the openings 138A, 138B (FIG. 1C) from within the outer housing 110. With the openings 138A, 138B (FIG. 1C) thus exposed, the needle carriers 160A, 160B and detachable needles 170A, 170B can be moved distally beyond and radially outward from the distal end 130A of the guide member 130 to move the detachable needles 170A, 170B at least partially through the vessel wall 310 on opposing sides of the puncture 300. As shown, the anchor member 180 in the expanded state can extend beyond the position of the detachable needles 170A, 170B in the vessel wall 310. Such a configuration can improve the ability of the anchor member 180 to support user pullback by increasing the area over which the anchor member 180 engages the inner surface of the vessel wall 300. In addition, the loop-type configuration of the anchor member 180 in the expanded state can allow the anchor member 180 to locate the vessel wall 310 without substantial interference from the detachable needles 170A, 170B. While the anchor member 180 in the expanded state is shown extending beyond the position of the detachable needle 170A, 170B, any size and/or configuration of the anchor member 180 that is suitable to support user pullback against the vessel wall 310 is possible. In one embodiment, the anchor member 180 in the expanded state can extend between the position of the detachable needles 170A, 170B and the sides of the puncture 300. In other embodiments, the anchor member 180 in the expanded state can extend considerably beyond the position of the detachable needles 170A, 170B.

Figure 3D:
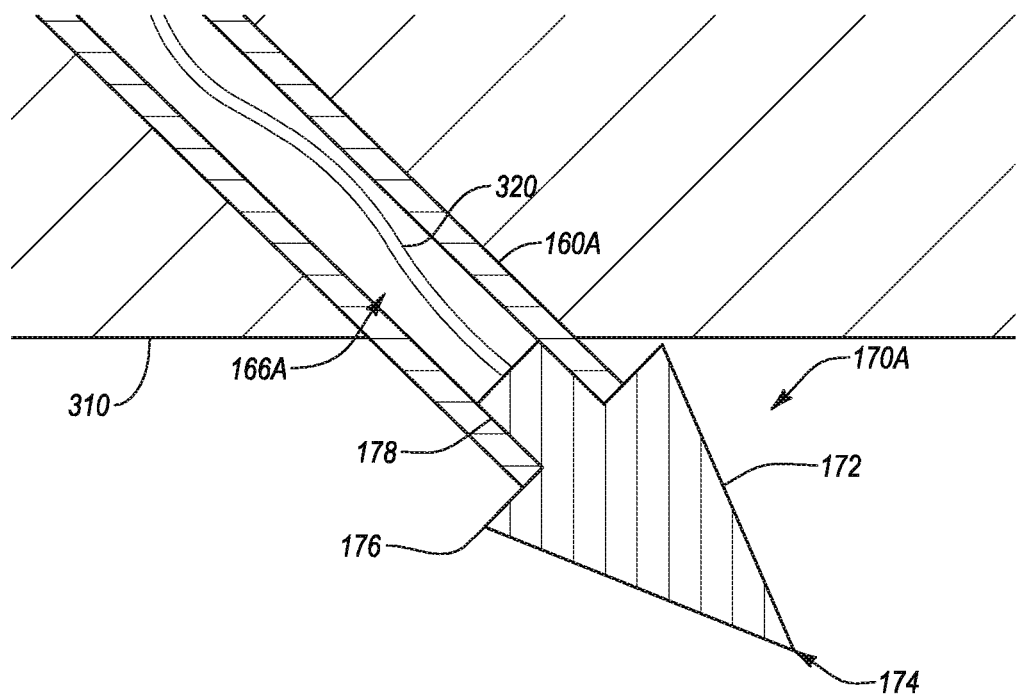
FIG. 3D illustrates a more detailed view of engagement between a detachable needle and the vessel wall of FIG. 3A.

FIG. 3D shows the detachable needle 170A in more detail. While a single detachable needle 170A is shown in FIG. 3D, it will be appreciated that the discussion of the detachable needle 170A can be equally applicable to the detachable needle 170B (FIG. 3C) as well as any number of other detachable needles. As shown in FIG. 3D, the detachable needle 170A may include features that allow it to readily pierce the vessel wall 310 while resisting retraction therefrom. In particular, the detachable needle 170A includes a generally conical body 172 having a tip 174 and a base 176. The detachable needle 170A may also include a shaft 178 coupled to the base 178.

In at least one example, the shaft 178 is configured to have a suture 320 coupled thereto. The shaft 178 can be further configured to be positioned within the suture lumen 166A to provide a slip fit between the needle carrier 160A and the shaft 178. The shaft 178 may also have a narrower aspect than the base 176. Such a configuration allows the needle carrier 160A to exert a distally acting force on the detachable needle 170A by way of the base 176. Such a distally acting force can cause the tip 174 to pierce the vessel wall 310 while the width of the base 176 anchors the detachable needle 170A to the vessel wall 310 and resists proximal retraction.

Referring again to FIG. 3C, once the detachable needles 170A, 170B are anchored in the vessel wall 310, the needle carriers 160A, 160B can be drawn proximally into the guide member 130. The engagement between the detachable needles 170A, 170B and the vessel wall 310 can be sufficient to detach the detachable needles 170A, 170B from the needle carriers 160A, 160B as the needle carriers 160A, 160B are withdrawn.

After the needle carriers 160A, 160B are drawn into the guide member 130, one of the control members 190A, 190B can be moved in one direction more than the other of the control members 190A, 190B to move the anchor member 180 into a contracted or collapsed state. The guide member 130, the plug 140, and the control member 180 can then be drawn into the outer housing 110. Thereafter, the closure device 10 can be withdrawn, leaving the detachable needles 170A, 170B engaged in the vessel wall 310 with the sutures 320 extending proximally from the detachable needles 170A, 170B as shown in FIG. 3E.

Figure 3E:
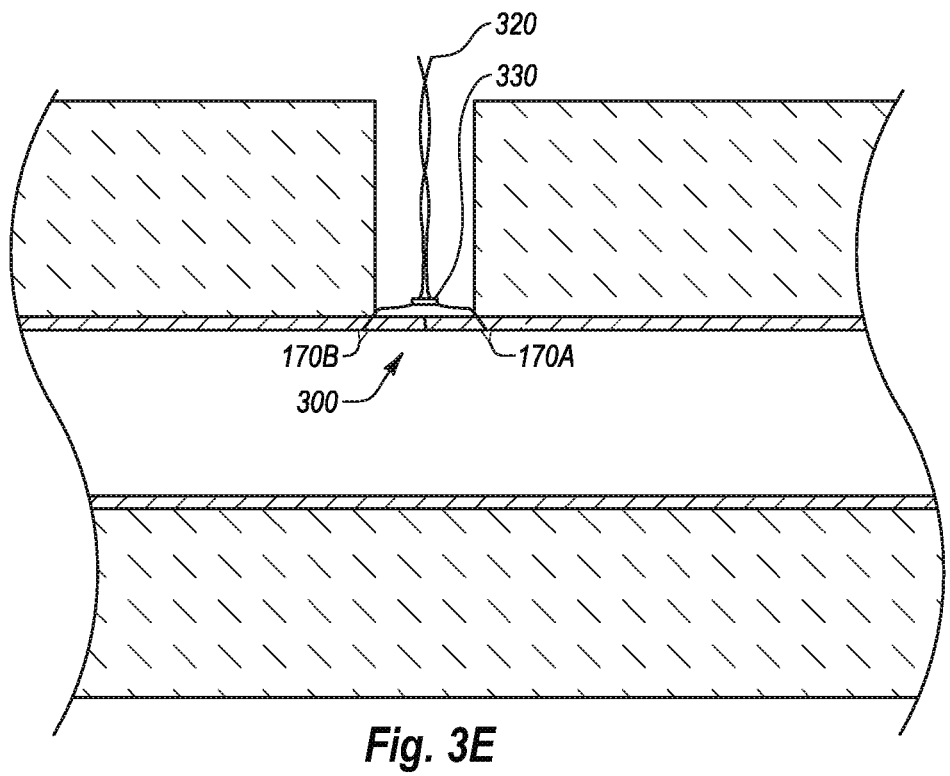
FIG. 3E illustrates steps for closing a puncture in a vessel wall in which the sutures and needles are secured in place to close the puncture in the vessel wall.

As also shown in FIG. 3E, a constrictor 330 can be passed over the sutures 320. The constrictor 330 can have a smaller diameter than the distance between the detachable needles 170A, 170B. As a result, moving the constrictor 330 over the sutures 320 while maintaining tension on the sutures 320 can act to draw the detachable needles 170A, 170B toward each other, thereby pulling the puncture 300 closed, as shown in FIG. 3E.

Once the puncture 300 is sufficiently closed, the constrictor 330 can be secured to maintain tension in the sutures 320 between the detachable needles 170A, 170B and the constrictor 330. For example, in one embodiment the constrictor 330 can be an annular member that can be crimped to maintain the tension in the sutures 320. While an annular member can be used, it will be appreciated that any constrictor can be used to establish tension in the sutures 170A, 170B. It will also be appreciated that any suitable means may also be used to maintain the tension in the sutures 170A, 170B. Thereafter, the sutures 170A, 170B can be trimmed as desired using any appropriate method and/or device.

Accordingly, as shown in FIGS. 1A-3E, the closure device 10 can be configured to deploy detachable needles 170A, 170B in a vessel wall 310. A constrictor 330 can then be used to establish tension in suture extending away from the detachable needles 170A, 170B to thereby close the puncture 300 in the vessel wall 310. In the illustrated example, two needle carriers 160A, 160B and detachable needles 170A, 170B have been described. It will be appreciated that in other examples, any number of needle carriers and detachable needles can be used, include four or more needle carriers and detachable needles.

Figure 4:
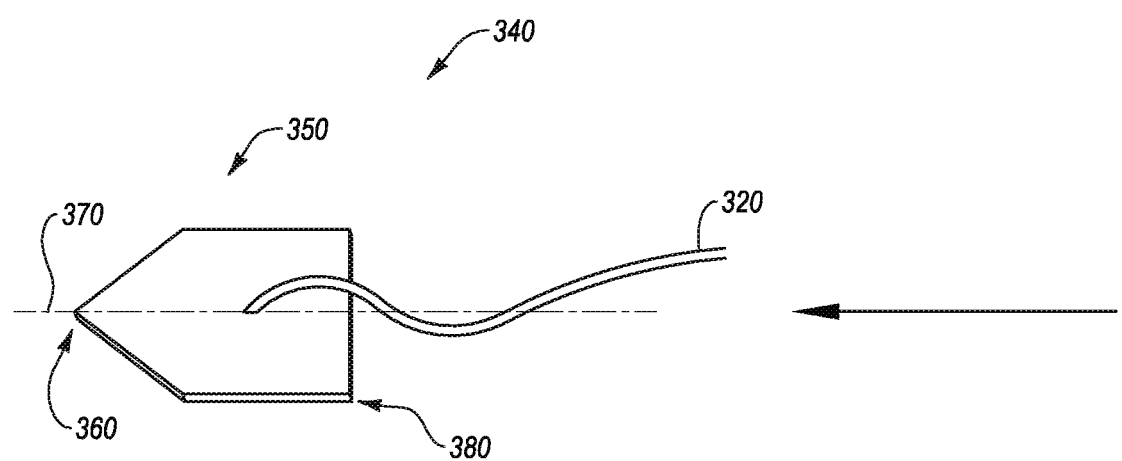
FIG. 4 illustrates a detachable needle according to one example.

In the example shown above, the detachable needles included a conical shape in which the sutures are anchored in a vessel wall by engagement with a proximal portion of the detachable needle. FIG. 4 illustrates one configuration for a detachable needle 340. The detachable needle 340 can have a body 350 having a tapered point 360. A suture 320 can be positioned in a manner that causes the detachable needle 340 to rotate when tension is applied to the suture 320 to thereby cause a lateral portion of the detachable needle 340 to engage a vessel wall to thereby anchor the detachable needle 340 thereto. For example, the suture 320 can be offset either radially from a center axis 370 of the detachable needle 340 and/or distally from a proximal end 380 of the body 350.

Figure 5A:
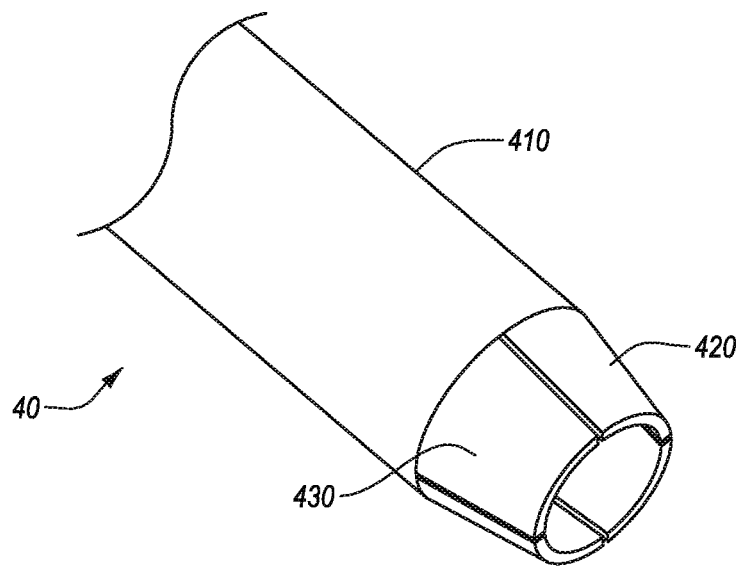
FIG. 5A illustrates a distal portion of a closure device according to one example.
Figure 5B:
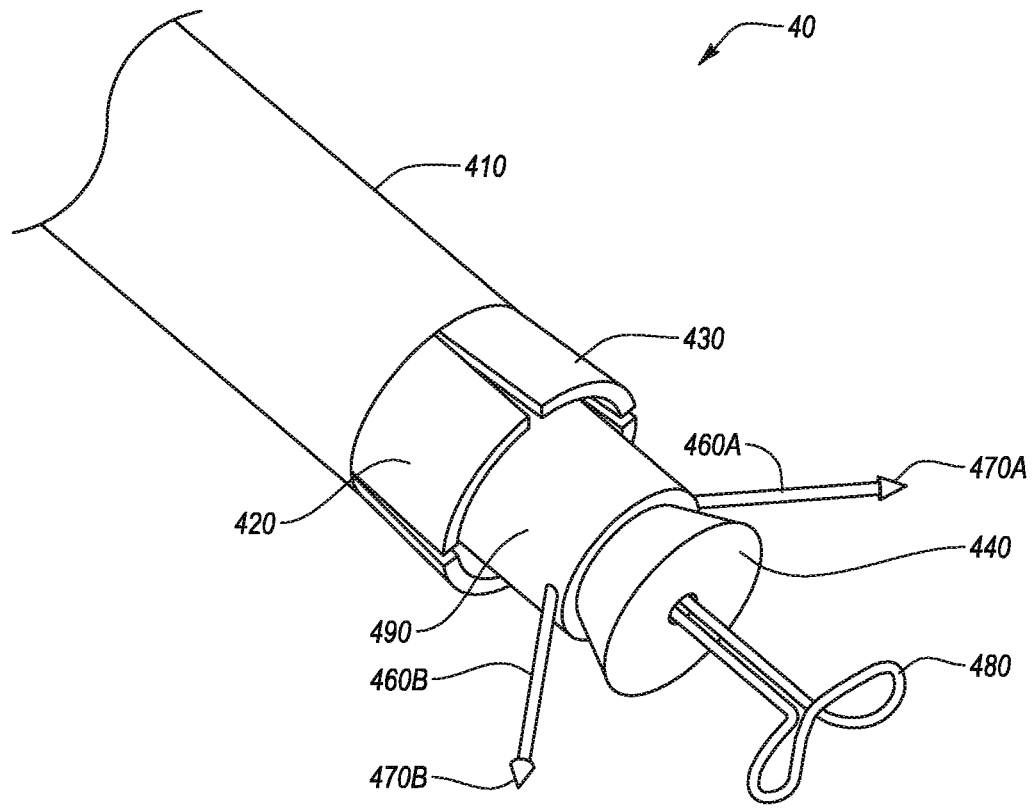
FIG. 5B illustrates the closure device shown in FIG. 5A in a deployed state.

FIGS. 5A-6B illustrate a vessel closure device 40 according to one example. The closure device 40 may be similar in many respects to the closure device 10 previously described above in FIGS. 1A-4, wherein certain features will not be described in relation to this configuration wherein those components may function in the manner as described above and are hereby incorporated into this additional configuration described below. As shown in FIG. 5A, the closure device 40 may include an outer sheath 410 having a distal end with a tapered tip portion 420. The tapered tip portion 420 may be formed of a polymer or any other suitable biocompatible material. The tapered tip portion 420 may be coupled to the outer sheath 410 or may be integrally formed on the outer sheath 410. In one embodiment, the tapered tip portion 420 may include slits radially spaced about the tapered tip portion 420 and extending proximally from a distal end of the tapered tip portion 420. The slits 430 may define intermediate portions of the tapered tip portion 420, each intermediate portion having a free end and a fixed end. The slits 430 may be elongated, triangular, diamond shaped, oval, or any other configuration and/or shape suitable to define the intermediate portions of the tapered tip portion 420. As shown in FIG. 5B, the slits 430 may allow the intermediate portions of the tapered tip portion 420 to expand or open up as a guide member 490, a plug 440, an anchor member 480, or needle guides 460A, 460B and detachable needles 470A, 470B are advanced from within the outer sheath 410. Such a configuration can help protect the guide member 490, the plug 440, the anchor member 480, the needle guides 460A, 460B and the detachable needles 470A, 470B, and/or the access tract. For example, the tapered tip portion 420 may help protect the access tract from damage that may be caused by the guide member 490, the plug 440, the anchor member 480, the needle guides 460A, 460B and the detachable needles 470A, 470B by enclosing them within the outer sheath 410 up until immediately adjacent a puncture 300. In addition, enclosing the same components within the outer sheath 410 up until immediately adjacent the puncture may help protect and improve the implementation of the guide member 490, the plug 440, the anchor member 480, the needle guides 460A, 460B and the detachable needles 470A, 470B by limiting interference from the access tract and/or other biological materials. Moreover, the conical shape of the tapered tip portion 420 can help ease advancement of the outer sheath 410 through the access tract.

Figure 6A:
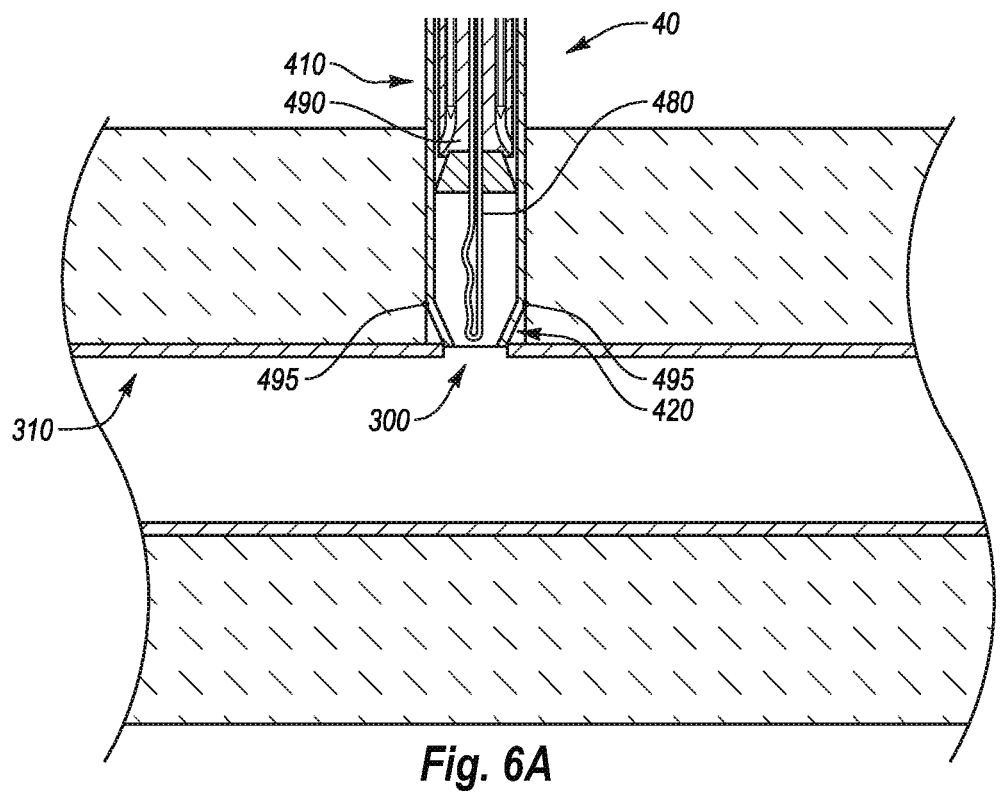
FIG. 6A illustrates a cross-sectional view of the closure device shown in FIG. 5A located relative to a vessel wall in a pre-deployed state.
Figure 6B:
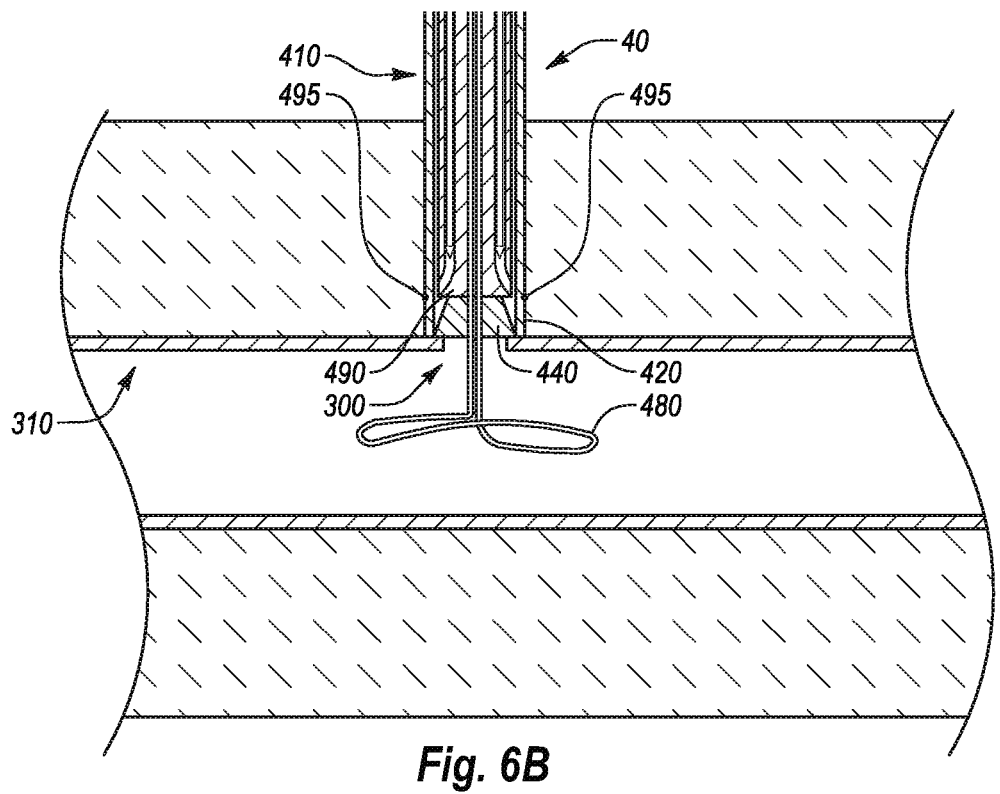
FIG. 6B illustrates a cross-sectional view of the closure device shown in FIG. 5A located relative to a vessel wall in a semi-deployed state.

FIGS. 6A and 6B illustrate the tapered tip portion 420 in a first configuration and an expanded or open configuration over a puncture in a vessel wall 310. As shown in FIG. 6A, the distal portion of the outer sheath 410 may be advanced through the access tract and the tapered tip portion 420 may be positioned slightly within the puncture 300. With the tapered tip portion 420 positioned in the puncture 300, the anchor member 480 can be passed directly into the puncture 300. The anchor member 480 can then be moved to a deployed expanded position as shown in FIG. 6B. The guide member 490 and plug 440 can then be urged through the tapered tip portion 420 and distally toward an outer surface of a vessel wall 310. As shown in FIG. 6B, urging the guide member 490 and the plug 440 through the tapered tip portion 420 can rotate the intermediate portions of the tapered tip portion 420 about pivot points 495 which in turn can cause the tapered tip portion 420 to expand or open up. In other embodiments, the intermediate portions of the tapered tip portion 420 can be flexed outward by the plug 440 and/or the guide member 490 to cause the tapered tip portion to expand or open up. In one embodiment, once the plug 440 and the anchor member 480 are positioned on opposite sides of the vessel wall 310, the outer housing 410 may be retracted distally a predetermined distance to allow for deployment of the needle guides 460A, 460B and the detachable needles 470A, 470B from the guide member 490.

Accordingly, as shown in FIGS. 5A-6B, the tapered tip portion 420 of the closure device may be configured to ease the advancement of the closure device 40 through an access tract; aid in the protection of the access tract, the closure device 40 and components thereof; and improve implementation of the closure device's components within the access tract.

Embodiments of the anchor, detachable needles and the like may include a material made from any of a variety of known suitable biocompatible materials, such as a biocompatible shape memory material (SMM). For example, the SMM may be shaped in a manner that allows for a delivery orientation while within the tube set, but may automatically retain the memory shape of the detachable needles once deployed into the tissue to close the opening. SMMs have a shape memory effect in which they may be made to remember a particular shape. Once a shape has been remembered, the SMM may be bent out of shape or deformed and then returned to its original shape by unloading from strain or heating. Typically, SMMs may be shape memory alloys (SMA) comprised of metal alloys, or shape memory plastics (SMP) comprised of polymers. The materials may also be referred to as being superelastic.

Usually, an SMA may have an initial shape that may then be configured into a memory shape by heating the SMA and conforming the SMA into the desired memory shape. After the SMA is cooled, the desired memory shape may be retained. This allows for the SMA to be bent, straightened, twisted, compacted, and placed into various contortions by the application of requisite forces; however, after the forces are released, the SMA may be capable of returning to the memory shape. The main types of SMAs are as follows: copper-zinc-aluminum; copper-aluminum-nickel; nickel-titanium (NiTi) alloys known as nitinol; nickel-titanium platinum; nickel-titanium palladium; and cobalt-chromium-nickel alloys or cobalt-chromium-nickel-molybdenum alloys known as elgiloy alloys. The temperatures at which the SMA changes its crystallographic structure are characteristic of the alloy, and may be tuned by varying the elemental ratios or by the conditions of manufacture. This may be used to tune the detachable needles so that it reverts to the memory shape to close the arteriotomy when deployed at body temperature and when being released from the tube set.

For example, the primary material of an anchor, detachable needles, and/or ring may be of a NiTi alloy that forms superelastic nitinol. In the present case, nitinol materials may be trained to remember a certain shape, retained within the tube set, and then deployed from the tube set so that the tines penetrate the tissue as it returns to its trained shape and closes the opening. Also, additional materials may be added to the nitinol depending on the desired characteristic. The alloy may be utilized having linear elastic properties or non-linear elastic properties.

An SMP is a shape-shifting plastic that may be fashioned into a detachable needles in accordance with the present disclosure. Also, it may be beneficial to include at least one layer of an SMA and at least one layer of an SMP to form a multilayered body; however, any appropriate combination of materials may be used to form a multilayered device. When an SMP encounters a temperature above the lowest melting point of the individual polymers, the blend makes a transition to a rubbery state. The elastic modulus may change more than two orders of magnitude across the transition temperature (Ttr). As such, an SMP may be formed into a desired shape of an endoprosthesis by heating it above the Ttr, fixing the SMP into the new shape, and cooling the material below Ttr. The SMP may then be arranged into a temporary shape by force and then resume the memory shape once the force has been released. Examples of SMPs include, but are not limited to, biodegradable polymers, such as oligo($\epsilon$-caprolactone)diol, oligo($\rho$-dioxanone)diol, and non-biodegradable polymers such as, polynorborene, polyisoprene, styrene butadiene, polyurethane-based materials, vinyl acetate-polyester-based compounds, and others yet to be determined. As such, any SMP may be used in accordance with the present disclosure.

An anchor, detachable needles, ring and the like may have at least one layer made of an SMM or suitable superelastic material and other suitable layers may be compressed or restrained in its delivery configuration within the garage tube or inner lumen, and then deployed into the tissue so that it transforms to the trained shape. For example, a detachable needles transitions to close the opening in the body lumen while an anchor may expand to anchor the closure device.

Also, the anchor, detachable needles, ring, or other aspects or components of the closure device may be comprised of a variety of known suitable deformable materials, including stainless steel, silver, platinum, tantalum, palladium, nickel, titanium, nitinol, nitinol having tertiary materials (U.S. 2005/0038500, which is incorporated herein by reference, in its entirety), niobium-tantalum alloy optionally doped with a tertiary material (U.S. 2004/0158309, 2007/0276488, and 2008/0312740, which are each incorporated herein by reference, in their entireties) cobalt-chromium alloys, or other known biocompatible materials. Such biocompatible materials may include a suitable biocompatible polymer in addition to or in place of a suitable metal. The polymeric detachable needles may include biodegradable or bioabsorbable materials, which may be either plastically deformable or capable of being set in the deployed configuration.

In one embodiment, the detachable needles, anchor, and/or ring may be made from a superelastic alloy such as nickel-titanium or nitinol, and includes a ternary element selected from the group of chemical elements consisting of iridium, platinum, gold, rhenium, tungsten, palladium, rhodium, tantalum, silver, ruthenium, or hafnium. The added ternary element improves the radiopacity of the nitinol detachable needles. The nitinol detachable needles has improved radiopacity yet retains its superelastic and shape memory behavior and further maintains a thin body thickness for high flexibility.

In one embodiment, the anchor, detachable needles, and/or ring may be made at least in part of a high strength, low modulus metal alloy comprising Niobium, Tantalum, and at least one element selected from the group consisting of Zirconium, Tungsten, and Molybdenum.

In further embodiments, the detachable needles, anchor, and/or ring may be made from or be coated with a biocompatible polymer. Examples of such biocompatible polymeric materials may include hydrophilic polymer, hydrophobic polymer biodegradable polymers, bioabsorbable polymers, and monomers thereof. Examples of such polymers may include nylons, poly(alpha-hydroxy esters), polylactic acids, polylactides, poly-L-lactide, poly-DL-lactide, poly-L-lactide-co-DL-lactide, polyglycolic acids, polyglycolide, poly-lactic-co-glycolic acids, polyglycolide-co-lactide, polyglycolide-co-DL-lactide, polyglycolide-co-L-lactide, polyanhydrides, polyanhydride-co-imides, polyesters, polyorthoesters, polycaprolactones, polyesters, polyanydrides, polyphosphazenes, polyester amides, polyester urethanes, polycarbonates, polytrimethylene carbonates, polyglycolide-co-trimethylene carbonates, poly(PBA-carbonates), polyfumarates, polypropylene fumarate, poly(p-dioxanone), polyhydroxyalkanoates, polyamino acids, poly-L-tyrosines, poly(beta-hydroxybutyrate), polyhydroxybutyrate-hydroxyvaleric acids, polyethylenes, polypropylenes, polyaliphatics, polyvinylalcohols, polyvinylacetates, hydrophobic/hydrophilic copolymers, alkylvinylalcohol copolymers, ethylenevinylalcohol copolymers (EVAL), propylenevinylalcohol copolymers, polyvinylpyrrolidone (PVP), combinations thereof, polymers having monomers thereof, or the like.

In yet a further embodiment, a closure device 50 may include needle guides that can be deployed from the closure device 50 at varying angles. The closure device 50 may be similar in many respects to the closure devices 10 and 40 previously described above in FIGS. 1A-6B, wherein certain features will not be described in relation to this configuration wherein those components may function in the manner as described above and are hereby incorporated into this additional configuration described below.

FIG. 7A shows a side view of the closure device 50. As shown, the closure device 50 may include a guide member 520, needle guides 510A, 510B deployable from the guide member 520, a needle guide activation handle 620 coupled to the needle guides 510A, 510B, and an angle adjustment member 630 movably attached to the guide member 520. FIG. 7B shows the needle guides 510A, 510B removed from the closure device 50. While features of a single needle guide 510A are discussed, it will be appreciated that any discussion of the features of the needle guide 510A can be equally applicable to the features of the needle guide 510B as well as any number of other needle guides.

The needle guides 510A, 510B may comprise a substantially flexible or semi-rigid body 530 having a proximal portion 540 and a distal portion 550. The proximal portions 540 are substantially parallel to or axially aligned with one another, whereas the distal portions 550 of the needle guides 510A, 510B may be angled or curved to extend laterally outward from the proximal portions 540. In one embodiment, the distal portions 550 of the needle guides 510A, 510B may be self-biased to extend laterally outward from the proximal portions 540. In another embodiment, the needle guides 510A, 510B may have a memory shape where the distal portions 550 extend laterally outward from the proximal portions 540. The needle guides 510A, 510B can be configured such that the needle guides 510A, 510B can be forcibly straightened but return to their curved or angled shape upon release from external forces.

As discussed in more detail below, the design of the needle guides 510A, 510B allows the angle adjustment member 630 to be configured to adjust a deployment angle "α" of the needle guides 510A, 510B. The deployment angle "α" is defined as the greatest acute angle between the needle guides 510A, 510B and a longitudinal axis of the guide member 520. In one configuration, the deployment angle "α" is in a range between about 20 degrees and about 60 degrees, while in another configuration the deployment angle "α" is between about 30 degrees and 50 degrees. One skilled in the art will understand that the deployment angle "α" can range between any puncture angle commonly used to suture an body lumen opening. Adjusting the deployment angle "α" allows the closure device 50 to be used on body lumen openings of varying sizes.

It will be understood by those skilled in the art that various other configurations of the needle guides 510A, 510B are possible. For example, although the needle guides 510A, 510B have at least an angled or curved portion 545, the body 530 of the needle guides 510A, 510B being entirely curved or substantially angled is possible. Moreover, the needle guides 510A, 510B may include a substantially rigid portion, a flexible portion and/or a semi-rigid portion. The needle guides 510A, 510B may be comprised of a biocompatible material such as one or more polymers, elastomers, plastics, metals, composites, other similar materials, or any combination thereof. The needle guides 510A, 510B may also include one or more superelastic or shape memory materials such as shape memory alloys. The needle guides 510A, 510B may have a cross-sectional configuration that is rectangular, circular, elliptical, triangular, uniform, varying, substantially solid, substantially hollow, or any other cross-sectional configuration suitable for deployment through a vessel wall (not shown in FIG. 7A). In one embodiment, the needle guides 510A, 510B may be configured to hold a suture (not shown) and/or a suture securing device (not shown). For example, the needle guides 510A, 510B can include a suture lumen 560 defined between the proximal portion 540 and the distal portion 550. The suture lumens 560 can be sized, shaped and/or configured to hold the suture and/or the suture securing device. Further, although two needle guides 510A, 510B are shown, one needle guide or a plurality of needle guides is possible. The needle guides 510A, 510B can also be configured to form a penetration path though a vessel wall 570 immediately surrounding a body lumen opening. As shown, the distal portion 550 of the needle guides 510A, 510B may include a penetrator tip 580. In another embodiment, the needle guides 510A, 510B may include a detachable penetrator tip disposed on the distal portion 550. In a further example, the penetrator tip 580 may comprise one or more sharpened edges on the distal portion 550 of the needle guides 510A, 510B.

As illustrated in FIG. 7A, the needle guides 510A, 510B can extend longitudinally along the length of the guide member 520 toward openings 610A, 610B near the distal end 670 of the guide member 520 (as shown by hidden lines in FIG. 7A). While the needle guides 510A, 510B are shown disposed within the guide member 520, the needle guides 510A, 510B disposed on the guide member 520 are possible. For example, the needle guides 510A, 510B may be positioned in between the outer surface of the guide member 520 and the inner surface of the angle adjustment member 630 in longitudinal grooves (not shown) formed on the outer surface of the guide member 520.

The needle guide activation plunger or handle 620 can be coupled to the needle guides 510A, 510B such that movement of the needle guide activation handle 620 can deploy the needle guides 510A, 510B though openings the 610A, 610B and distally of the guide member 520. While a needle activation plunger or handle is shown, any number of mechanisms can deploy the needle guides 510A, 510B distally of the guide member 520 such as a release button, a trigger, an actuator, or other mechanisms capable of deploying the needle guides 510A, 510B.

The angle adjustment member 630 may include a proximal end 640 and a distal end 650 and concentrically surround the guide member 520. The angle adjustment member 630 can be configured to support the needle guide activation handle 620 and move relative to the length of the guide member 520. In another embodiment, the guide member 520 may move relative to the angle adjustment member 630. The angle adjustment member 630 may be further configured so that the angle adjustment member 630 can adjust the deployment angle "α" of the needle guides 510A, 510B. While the angle adjustment member 630 is shown as a sheath, the angle adjustment member 630 may comprise elongate members moveably attached to opposing sides of the guide member 520, or an annular member moveably attached to the guide member 520 having one or more deflector rods aligned with the openings 610A, 610B, or any other configuration suitable to adjust the deployment angle "α" of the needle guides 510A.

Figure 8A:
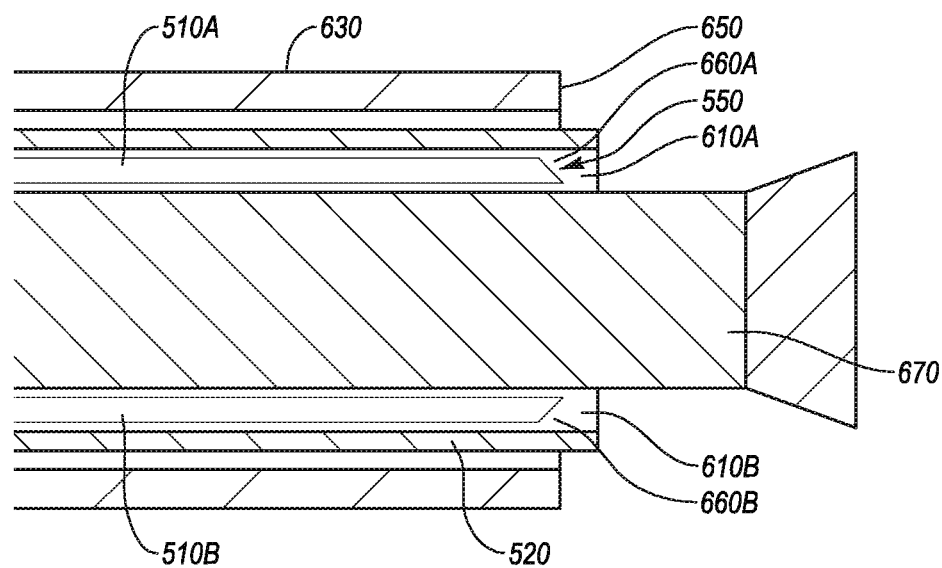
FIG. 8A illustrates a cross-section view of the closure device taken along section 6-6 of FIG. 7A with the needle guides in a pre-deployed state and an angle adjustment member in a retracted position.

FIGS. 8A-8D are cross-sectional views of the closure device 50 taken at various positions along section 6-6 of FIG. 7A to illustrate adjustment of the deployment angle "α" by the angle adjustment member 630. As shown in FIG. 8A, while in a pre-deployed state the needle guides 510A, 510B may be positioned within the guide member 520. Again, while the needle guides 510A, 510B are shown disposed within the guide member 520, needle guides 510A, 510B disposed on the guide member 520 are possible. As shown, the guide member 520 may include a plurality of lumens 660A, 660B extending distally toward the openings 610A, 610B of the guide member 520. The lumens 660A, 660B may be sized to receive at least one of the needle guides 510A, 510B. The lumens 660A, 660B may extend parallel to the longitudinal axis of the guide member 520. The needle guides 510A, 510B may be forcibly straightened within the lumens 660A, 660B. This facilitates low-profile storage of the needle guides 510A, 510B and the closure device 10 generally. Moreover, storage of the needle guides 510A, 510B within the lumens 660A, 660B can help prevent contamination of the needle guides 510A, 510B.

The openings 610A, 610B may be aligned along the longitudinal axis of the guide member 520 and be in fluid communication with the lumens 660A, 660B. As shown, the openings 610A, 610B may be located near a distal end 670 of the guide member 520. Although the openings 610A, 610B in the guide member 520 are shown parallel to the longitudinal axis of the guide member 520, the openings 610A, 610B can be oriented at any desirable angle relative to the guide member 520. For example, the openings 610A, 610B may be oriented substantially non-parallel to the longitudinal axis of the guide member 520 such that the openings 610A, 610B direct the needle guides 510A, 510B radially away from the guide member 520. Moreover, while the openings 610A, 610B are shown formed on the end of the guide member 520, the openings 610A, 610B may be formed on the sidewalls of the guide member 520. The needle guides 510A, 510B can be advanced through the openings 610A, 610B by manipulation of the needle guide activation handle 620 (not shown).

Figure 8B:
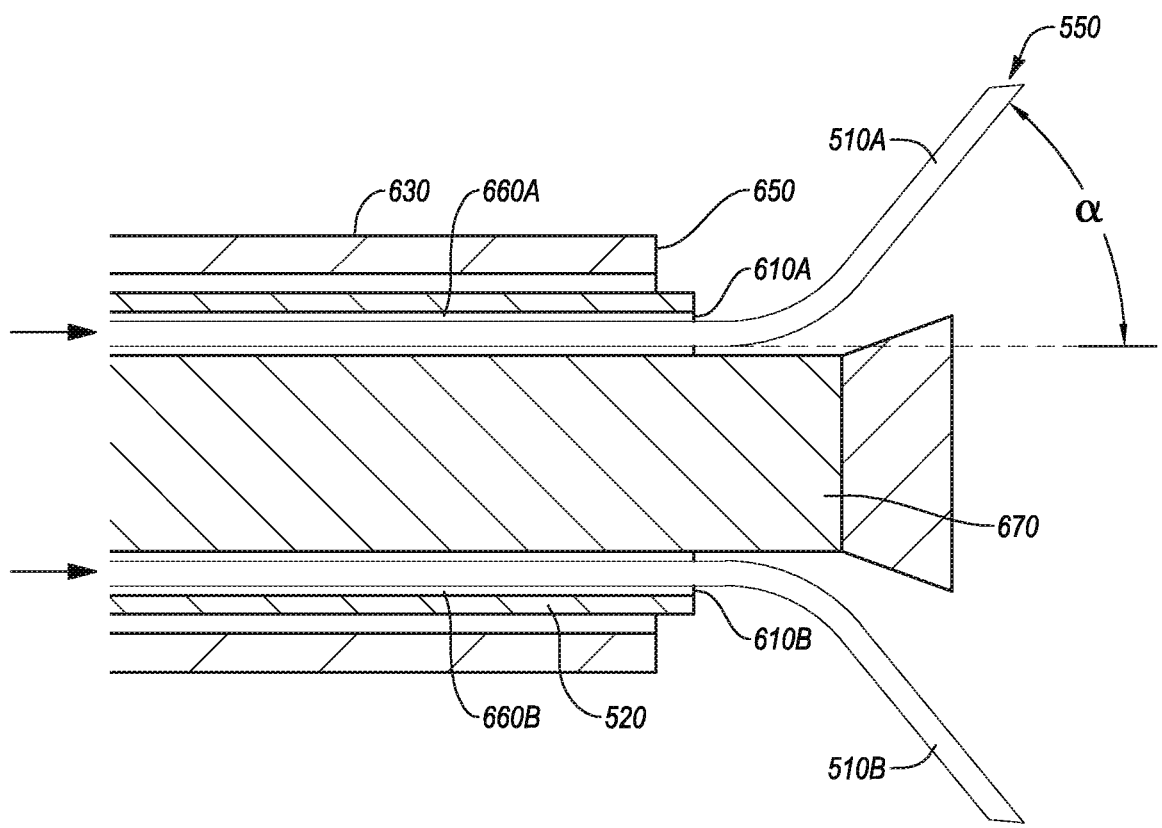
FIG. 8B illustrates the closure device shown in FIG. 8A with the needle guides deployed from the closure device and the angle adjustment member in the retracted position.

FIG. 8B shows the needle guides 510A, 510B deployed from the guide member 520 with the angle adjustment member 630 in a retracted position. As shown, the angle adjustment member 630 can be advanced along and relative to the guide member 520 such that the distal end 650 of the angle adjustment member 630 is positioned proximal to the openings 610A, 610B in the guide member 520. Consequently, the needle guides 510A, 510B may form a penetration path through the vessel wall 570 without being biased toward the longitudinal axis of the guide member 520 by the angle adjustment member 630. With the angle adjustment member 630 in the retracted position, the primary deployment angle "α" of the needle guides 510A, 510B may be approximately 60 degrees relative to the longitudinal axis of the guide member 520, as determined primarily by the configuration of the needle guides 510A, 510B. The primary deployment angle "α" minimizes the deployment depth, thereby minimizing the possibility of overshooting the vessel. Moreover, the primary deployment angle "α" maximizes the radial span of the needle guides 510A, 510B, thereby maximizing the size of the body lumen opening the needle guides 510A, 510B can close.

Figure 8C:
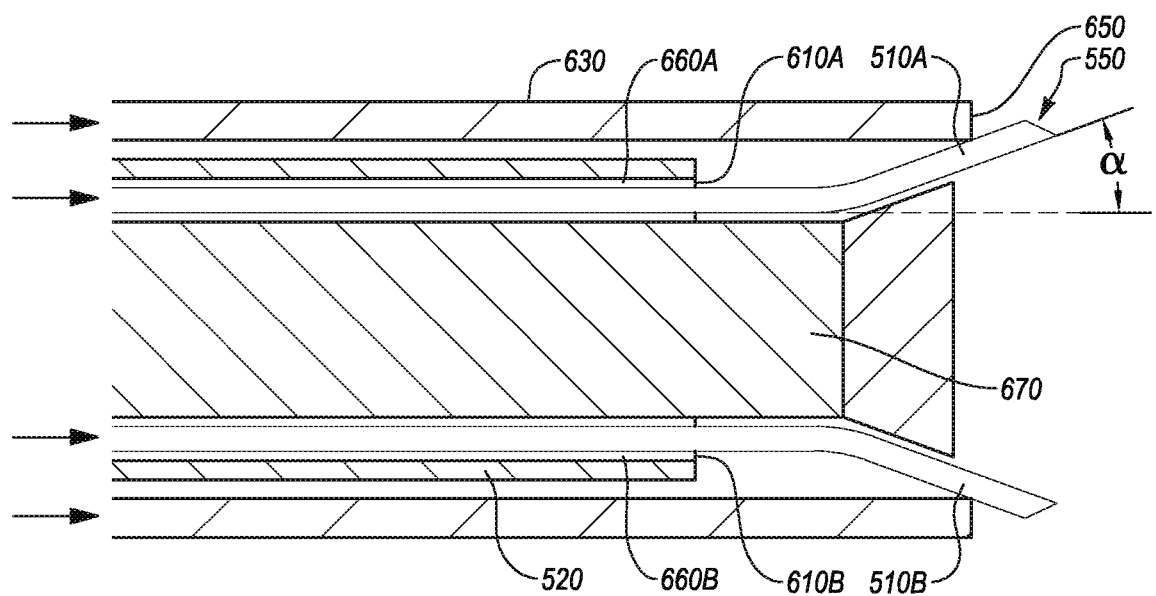
FIG. 8C illustrates the closure device shown in FIG. 8A with the needle guides deployed from the closure device and the angle adjustment member in an extended position.

FIG. 8C shows the needle guides 510A, 510B deployed from the guide member 520 with the angle adjustment member 630 positioned in an extended position. As shown, the angle adjustment member 630 can be advanced along and relative to the guide member 520 until the distal end 650 of the angle adjustment member 630 is distal of the openings 610A, 610B. The angle adjustment member 630 may be substantially aligned or proximal to the distal end 670 of the guide member 520. In the extended position, the angle adjustment member 630 may deflect the needle guides 510A, 510B toward the deployment angle "α" of approximately 20 degrees relative to the guide member 520. With the angle adjustment member 630 in the extended position, the needle guides 510A, 510B can close a smaller body lumen opening.

Figure 8D:
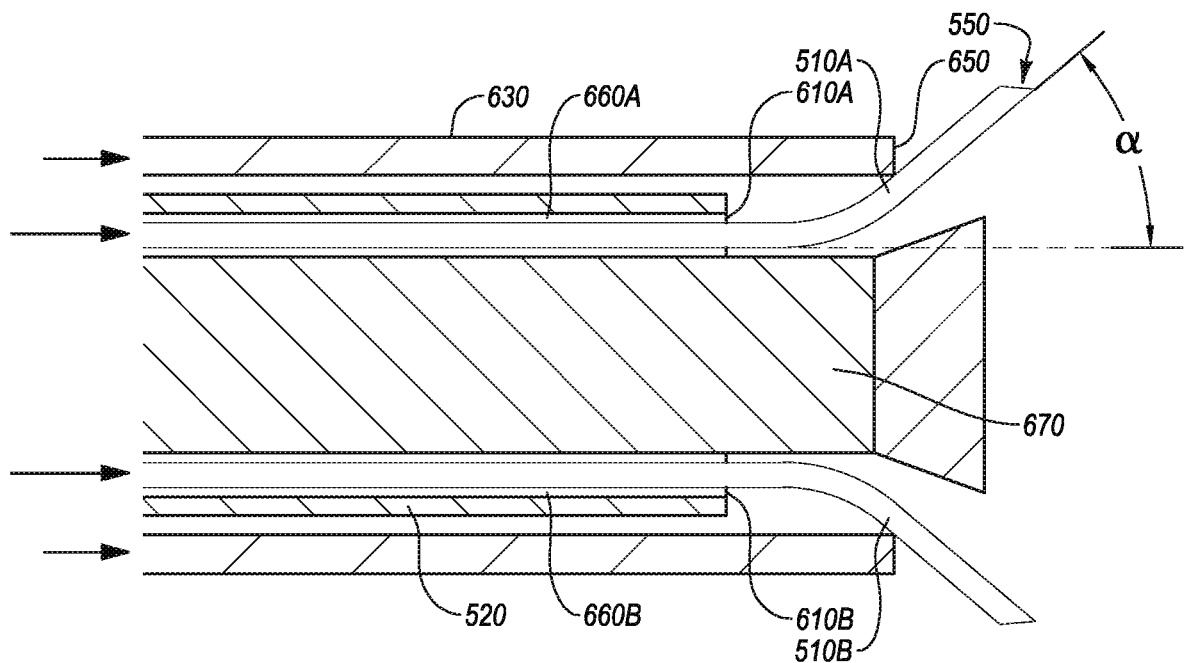
FIG. 8D illustrates the closure device shown in FIG. 8A with the needle guides deployed from the vessel closure device and the angle adjustment member in an intermediate position.

FIG. 8D shows the needle guides 510A, 510B deployed from the guide member 520 with the angle adjustment member 630 positioned in an intermediate position. The intermediate position is defined between the retracted position and the extended position. In the intermediate position, the angle adjustment member 630 may be advanced along and relative to the guide member 520 such that the distal end 650 of the angle adjustment member 630 is positioned distal to the openings 610A, 610B but proximal to the position of the angle adjustment member 630 in the extended position. With the angle adjustment member 630 in the intermediate position, the angle adjustment member 630 may deflect the needle guides 510A, 510B toward the deployment angle "α" between about 20 degrees and about 60 degrees. Distal movement of the angle adjustment member 630 beyond the openings 610A, 610B will reduce the deployment angle "α" toward about 20 degrees until the angle adjustment member 630 reaches the extended position. Proximal movement of the angle adjustment member 630 beyond the openings 610A, 610B will increase the deployment angle "α" toward about 60 degrees until the angle adjustment member 630 reaches the retracted position. Thus, a user can adjust the deployment angle of the needle guides 510A, 510B anywhere between about 20 degrees and about 60 degrees by moving the angle adjustment member 630 between the retracted position and the extended position.

Figure 9A:
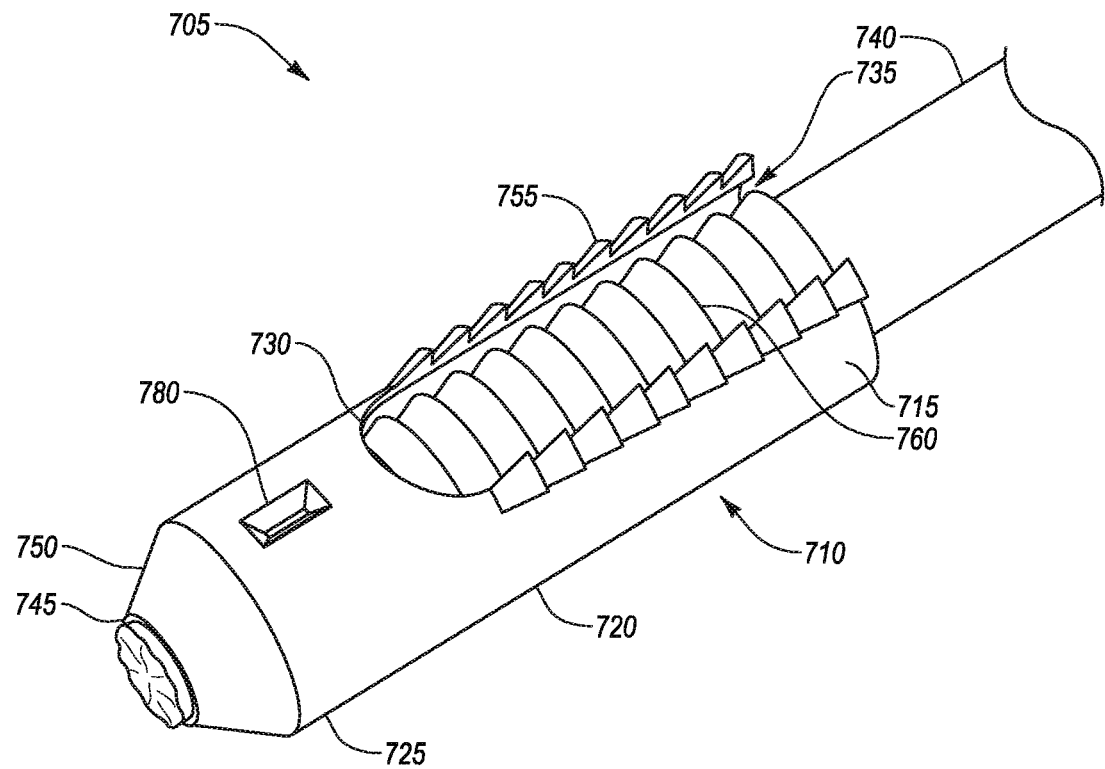
FIG. 9A shows a perspective view of a suture securing device according to one example.

In another embodiment, the closure device 10, closure device 40, or closure device 50 may employ an articulating suture securing device having a low-profile configuration and an expanded configuration. FIG. 9A shows a perspective view of a suture securing device 705 according to one example. As shown, the suture securing device 705 may comprise a tubular body 710, a cutout 730 formed in the tubular body 710, and a suture 740 attached to the tubular body 710.

The tubular body 710 may be elongated and have a proximal end 715, an intermediate portion 720, and a distal end 725. The tubular body 710 can include a first opening 735 at the proximal end 715 for receiving an end of the suture 740. The suture 740 may extend into the interior of the tubular body 710 along its length. The suture 740 may exit the tubular body 710 through a second opening 745 located near the distal end 725. While the suture 740 is shown exiting the tubular body through the second opening 745 located near the distal end 725, the suture 740 may exit the tubular body 710 at any number of locations. For example, a second opening may be located near the intermediate portion 720 of the tubular body 710 such that the suture may exit the tubular body 710 near the intermediate portion 720. In another example, a third opening (not shown) may be located between the intermediate portion 720 and the distal end 725 such that the suture 740 may exit through the third opening.

The tubular body 710 may be crimped, as shown at 780, about the suture 740 to mechanically affix the suture 740 to the suture securing device 705. In other embodiments, the tubular body 710 can be crimped in a plurality of locations. In addition and or instead to mechanical crimping, the suture 740 may be bonded to the suture securing device 705 using an adhesive, heat, fasteners, knots or the like. The tubular body 710 may also include a swaged portion 750 adjacent the second opening 745 to help retain the suture 740 in the tubular body 710. The tubular body 710 may include any number of rigid or semi-rigid materials. For example, the tubular body 710 may include one or more polymers, elastomers, plastics, metals, composites, other similar materials, or combinations thereof. The tubular body 710 may also include one or more superelastic or shape memory materials such as shape memory alloys.

The cutout 730 may extend distally from the proximal end 715 of the tubular body 120. In other embodiments, more than one cutout 730 is possible. While the cutout 730 is shown having being u-shaped, a rectangular, triangular, elliptical, oval, or any other suitable shape is possible. The cutout 730 may include a plurality of tissue-engaging elements 755 extending along each side of the cutout 730. In other embodiments, the tissue-engaging elements 755 may also be formed on other portions of the tubular body 710. For example, the tissue-engaging elements 755 may be formed over the entire outer surface of the tubular body. In a further example, the tissue-engaging elements 755 may be formed between the proximal end 715 and the intermediate portion 720 of the tubular body 710. In yet a further example, the tissue-engaging elements 755 may be formed between the proximal end 715 and the distal end 725 on the same surface as the cutout 730. In other embodiments, the cutout 730 may include one or more tissue-engaging elements.

The tissue-engaging elements 755 extend from opposing sides of the cutout 730 and may comprise teeth, serrations, tilted trapezoidal bodies, or any other shape or configuration suitable to increase friction when engaged against a vessel wall. It will be apparent to one skilled in the art that a variety of tissue-engaging element configurations may be possible. For example, the tissue-engaging elements 755 may have tapered bodies. The tissue-engaging elements 755 may have generally circular disc-shaped bodies. The tissue-engaging elements 755 may have setaceous bodies. The tissue-engaging elements 755 may have hook shaped bodies. The tissue-engaging elements 755 may have tine shaped bodies. The tissue-engaging elements 755 may comprise notches formed in the tubular body 710. The orientation of the tissue-engaging elements 755 may also vary. For example, the tissue-engaging elements 755 may be angled toward or away from the cutout 730. The tissue-engaging elements 755 may be curved inwardly or outwardly relative to the cutout 730. The tissue-engaging elements 755 may alternate between extending inward and outward from the cutout 730.

In another embodiment, at least a portion of the suture 740 may include friction producing structures 760. The friction producing structures 760 may include a plurality of annular vanes formed in the outer surface of the suture 740. In another embodiment, the friction producing structures 760 may include raised helically formed or threaded portions on or in the suture 740. In another embodiment, the friction producing structures 760 may include one or more annular grooves formed in the suture 740. In another embodiment, the friction producing structures 760 may be formed on a substantially rigid portion of the suture 740. In a further embodiment, the friction producing structures 760 may be non-uniformly distributed on the suture 740. In yet a further embodiment, the friction producing structures 760 may include a plurality of raised portions and a plurality of recessed portions.

Figure 9B:
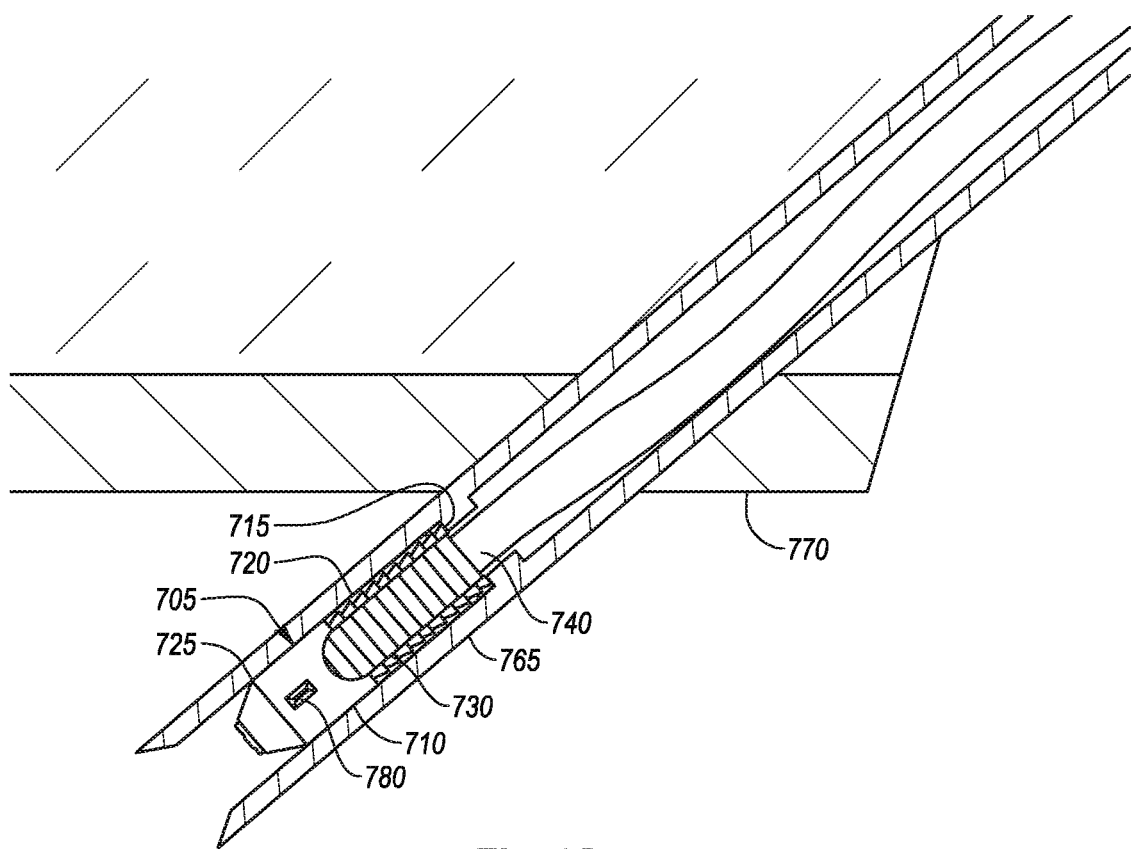
FIG. 9B shows the suture securing device shown in FIG. 9A deployed through a vessel wall in a low-profile configuration within a needle guide.
Figure 9C:
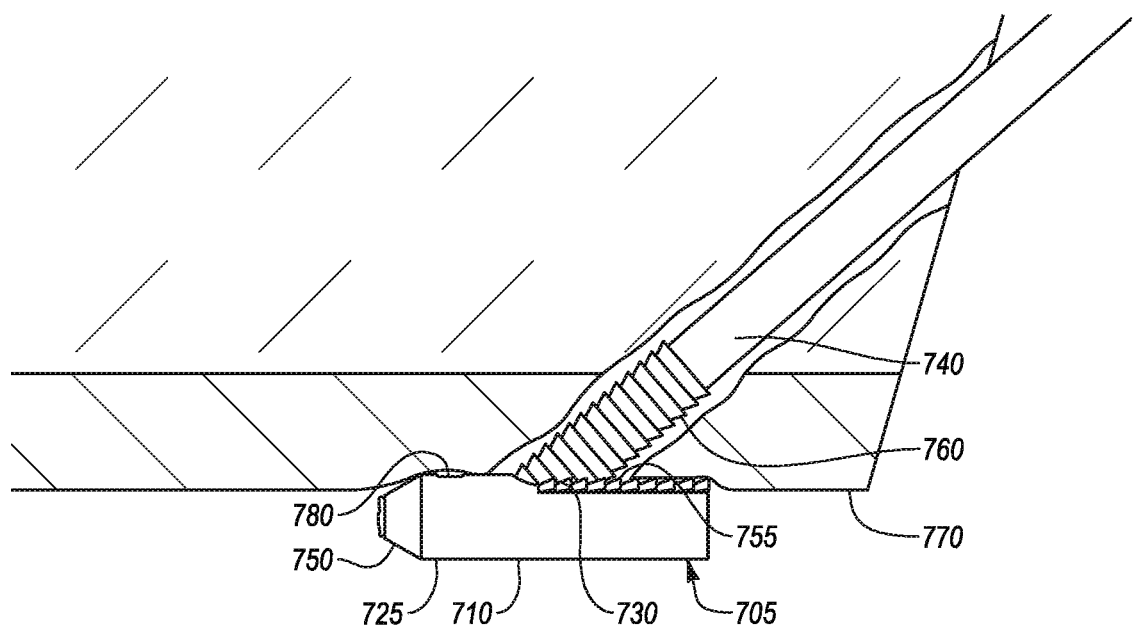
FIG. 9C shows the suture securing device shown in FIG. 9B released from the needle guide in an expanded configuration.

FIGS. 9B and 9C show the suture securing device 705 in a low-profile configuration (FIG. 9B) and an expanded configuration (FIG. 9C). As shown in FIG. 9B, the suture securing device 705 may have a low-profile configuration in which the tubular body 710 is substantially aligned along the axis of the suture 740. The low-profile configuration shown in FIG. 9B facilitates storage and delivery of the suture securing device 705. For example, a needle guide 765 may hold the suture securing device 705 and the suture 740 as the needle guide 765 forms a penetration path through the vessel wall 770 immediately adjacent a body lumen opening. In another embodiment, the suture securing device 705 can be configured to penetrate the vessel wall 770 rather than the needle guide 765. For example, the suture securing device 705 can be disposed on the needle guide 765 with a penetrator tip (not shown) attached to the distal end 725 of the suture securing device 705.

As shown in FIG. 9C, the suture securing device 705 may have an expanded configuration. In one embodiment, the needle guide 765 may be retracted depositing or releasing the suture securing device 705 distally of the vessel wall 770. The tubular body 710 may then rotate relative to the suture 740 such that the suture 740 is received within the cutout 730 and the tubular body 710 is positioned substantially non-parallel to the suture 740 and substantially parallel to the vessel wall 770. In another embodiment, the tubular body 710 may include more than one cutout configured to receive the suture 740 such that the tubular body 710 may rotate relative to the suture 740 in a plurality of directions. For example, the tubular body 710 may include a second cutout (not shown) formed opposing the cutout 730 such that the tubular body 710 may rotate clockwise or counterclockwise about the suture 740. In a further embodiment, the cutout 730 may include a receptacle (not shown) configured to fix the orientation of the suture 740 relative to the tubular body 710 once the suture securing device 705 moves into the expanded configuration. In yet a further embodiment, the cutout 730 may include a locking clip (not shown) to fix the orientation of the suture 740 relative to the tubular body 710 once the suture securing device 705 moves into the expanded configuration. In yet a further embodiment, the cutout 730 may include a catch member (not shown) to fix the orientation of the suture 740 relative to the tubular body 710 once the suture securing device 705 moves into the expanded configuration.

Figure 10A:
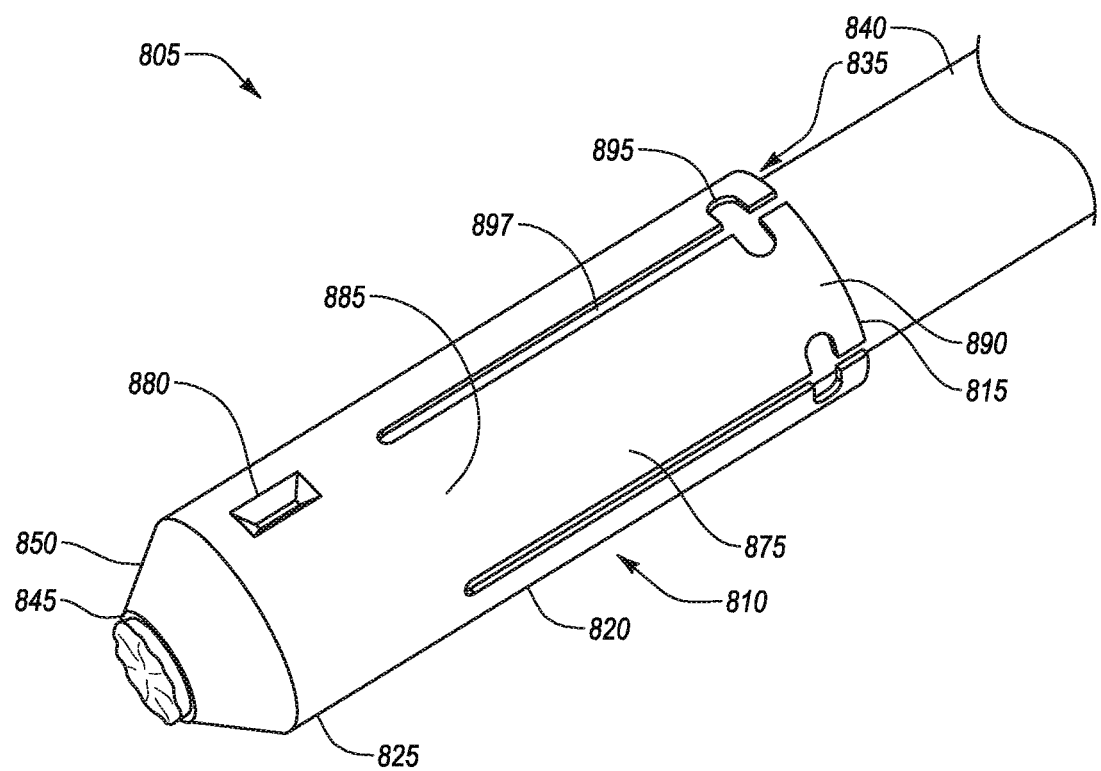
FIG. 10A shows a perspective view of a suture securing device according to one example.
Figure 10B:
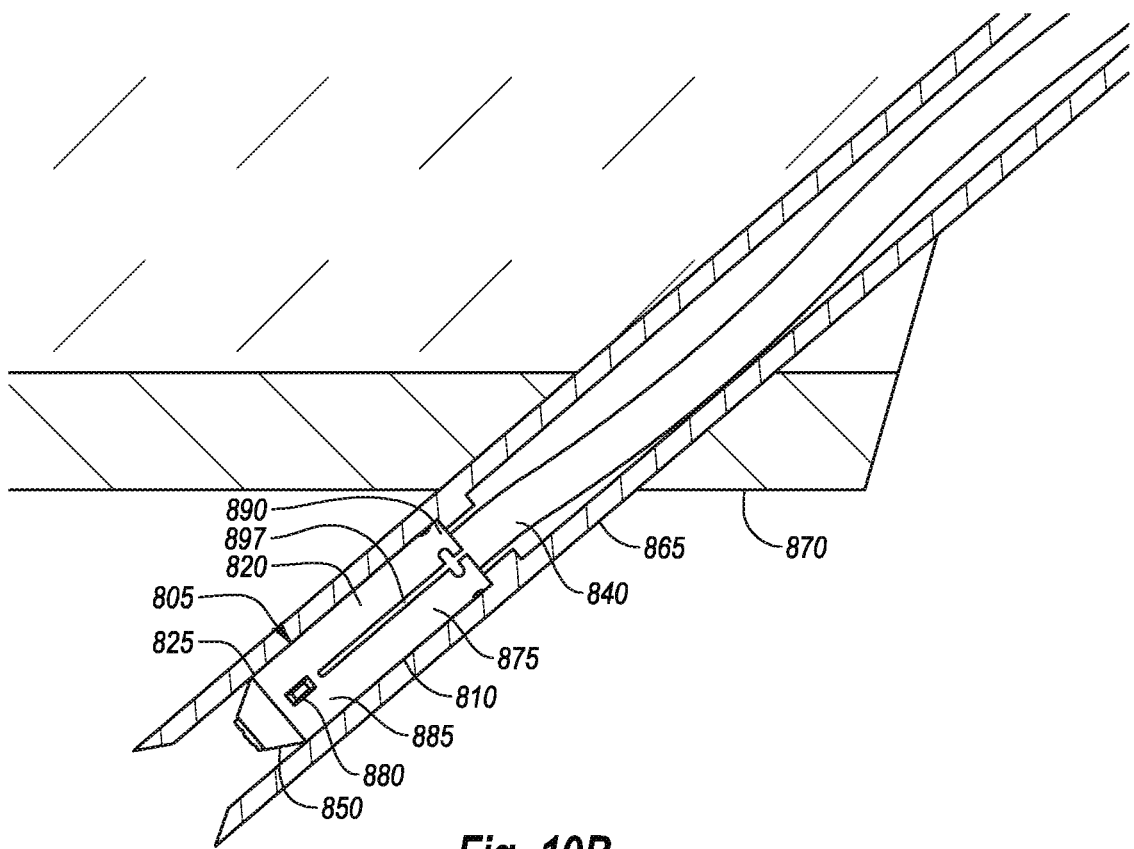
FIG. 10B shows the suture securing device shown in FIG. 10A deployed through a vessel wall in a collapsed configuration within a needle guide.
Figure 10C:
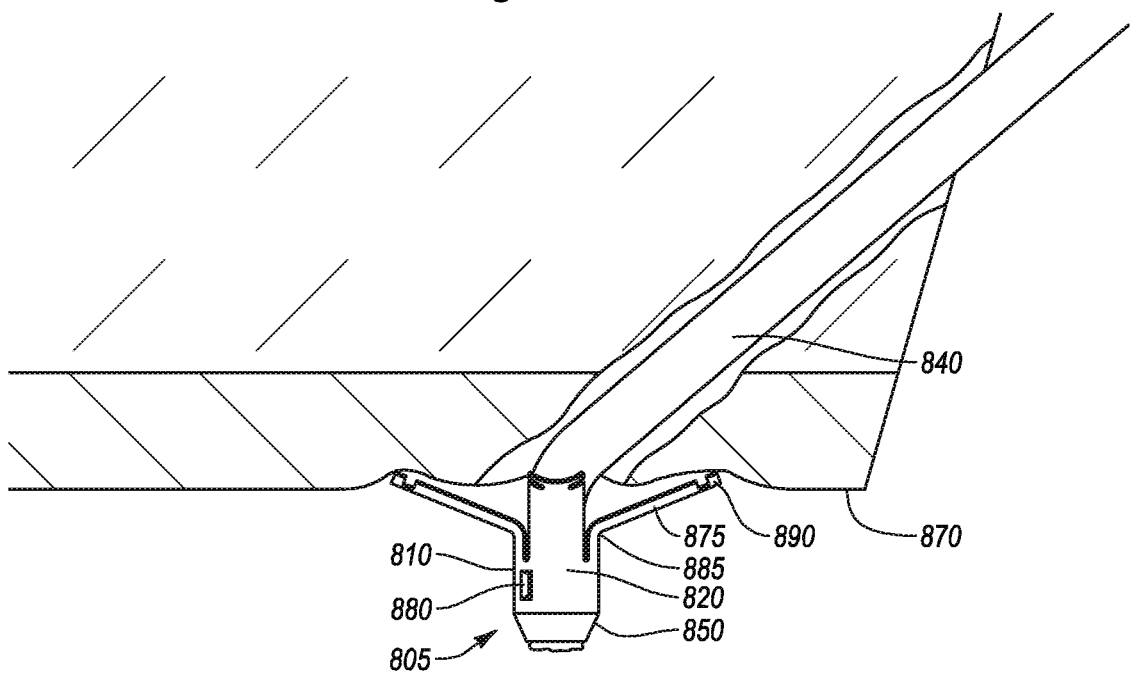
FIG. 10C shows the suture securing device shown in FIG. 10B released from the needle guide in an expanded configuration.

Reference is now made to FIGS. 10A-10C which illustrates an additional example suture securing device 805. The suture securing device 805 may be similar in many respects to the suture securing device 705 previously described above in FIGS. 9A-9C. To the extent features or components of this configuration function in a manner similar to that as described above, such disclosure is hereby incorporated into the following additional configuration. Like structures and/or components are given like reference numerals. Additionally, the suture securing device 805 may incorporate at least one component of the suture securing device 705 described in FIGS. 9A-9C.

As shown in FIG. 10A, the suture securing device 805 may include a tubular body 810 having a proximal end 815, a mid-point 820, and a distal end 825. The tubular body 810 can include a first opening 835 at the proximal end 815 for receiving an end of a suture 840. The suture 840 may extend distally within the tubular body 810 along its length. The suture 840 can also exit the tubular body 810 through a second opening 845 located near the distal end 825. As shown, the tubular body 810 may be crimped 880 about the suture 840 near the distal end 825 to mechanically affix the suture 840 to the suture securing device 805. In other embodiments, the tubular body 810 can be crimped in a plurality of locations. In addition and or instead to mechanical crimping, the suture 840 may be bonded to the suture securing device 805 using an adhesive, heat, fasteners, knots or the like. The tubular body 810 may also include a swaged portion 850 adjacent the second opening 845 to help retain the suture 840 in the tubular body 710.

The tubular body 810 may include a plurality of elongated slots 897 radially spaced about the tubular body, and extending distally from the proximal end 815. The slots 897 may define a plurality of projections 875 therebetween. In one embodiment, each projection 875 may have a wire, strip-like, or ribbon like shape with a fixed end 885 and a free end 890. The projections 875 of the tubular body 810 may be formed by one of more strips of material. In one embodiment, the projections 875 may include notches 895 formed near the free end 890. The notches 895 may be sized, shaped, and configured to help anchor the projections 875 against a vessel wall 870. In another embodiment, the projections 875 may include tissue-engaging elements formed near the free end 890. For example, the projections 875 may include one or more teeth shaped elements, tines, and/or barbs that are oriented to engage the vessel wall 870. The free end 890 of the projections 875 may also be forked such that the free end 890 can penetrate the vessel wall 870.

In one embodiment, the tubular body 810 may have four projections 875. In another embodiment, the tubular 810 may have six projections 875. In a further embodiment, the projections 875 may be spaced evenly about the tubular body 810. In a further embodiment, the projections 875 may form a shape similar to an 'x'. In yet further embodiment, the tubular body 810 may have multiple layers of projections 875. For example, the tubular body 810 may include a first set of projections 875a and a second set of projections 875b. Each set may include any number of projections 875 desired for a particular application. In further embodiments, each projection 875 may have any shape, size, or configuration desired for a particular application.

As shown in FIG. 10B, the suture securing device 805 may have a collapsed configuration in which the projections 875 are substantially parallel with a longitudinal axis of the tubular body 810. The collapsed configuration shown in FIG. 10B may facilitate storage and delivery of the suture securing device 805. A needle carrier 865 may hold the suture securing device 805 in the collapsed configuration as the needle carrier 865 forms a penetration path through the vessel wall 870 immediately adjacent a body lumen opening. In another embodiment, the suture securing device 805 can be configured to penetrate the vessel wall 870 rather than the needle guide 865. For example, the suture securing device 805 can be disposed on the needle guide 865 with a penetrator tip (not shown) attached to the distal end 825 of the suture securing device 805.

As shown in FIG. 10C, the suture securing device 805 may have an expanded configuration. In one embodiment, the needle guide 865 may be retracted from the penetration path depositing or releasing the suture securing device 805 distally of the vessel wall 870. The projections 875 may then move to the expanded configuration wherein the projections 875 are substantially non-parallel with the longitudinal axis of the tubular body 810. In one embodiment, the projections 875 may include one or more elastic or shape memory materials, such as spring steel, nitinol, and/or other shape memory alloys, and may be heat set to have a memory shape. For example, the projections 875 may be heat set in their expanded configuration. As a result, when the suture securing device 805 is deployed, it may superelastically move to an expanded configuration. A user may apply a force to the suture securing device 805 to deform the projections 875 away from their memory shape and move the suture securing device 805 into a collapsed configuration, as shown in FIG. 10B. Alternatively, the projections 875 may be resiliently biased towards the expanded configuration. As a result, when the suture securing device 805 is released from an external force such as the needle guide 865, the projections 875 may move to their expanded configuration. In another embodiment, the projections 875 may be pivotally connected to the tubular body 810. In a further embodiment, the projections 875 may be pivotally connected to the proximal end 815 of the tubular body 810. When the suture securing device 805 is stored within the needle guide 865, the projections 875 may be rotated to the collapsed configuration. As shown, when the suture securing device 810 is deployed from the needle guide 865, the projections 875 can rotate to the expanded configuration.

The present disclosure may be embodied in other specific forms without departing from its spirit or essential characteristics. The described embodiments are to be considered in all respects only as illustrative and not restrictive. The scope of the disclosure is, therefore, indicated by the appended claims rather than by the foregoing description. All changes which come within the meaning and range of equivalency of the claims are to be embraced within their scope.

What is claimed is:

1. A method for closing a puncture in tissue, the method comprising:
   advancing a guide member into proximity with the tissue, the guide member having a needle guide;
   positioning a distal end of the guide member with the needle guide toward the tissue to present an opening of the needle guide toward the tissue, the distal end of the guide member with the needle guide maintaining a position proximal to an anterior side of the tissue, the needle guide cooperating with a suture securing device that is slidably coupled to the guide member, and a suture attached to the suture securing device;
   deploying the suture securing device in a distal direction, the suture securing device comprising a body with an anchor point for the suture and features that allow the suture securing device to pierce the tissue and resist retraction through the tissue;
   wherein during deployment of the suture securing device, the features that allow the suture securing device to pierce the tissue and resist retraction are moved distally beyond and radially outward from the distal end of the guide member and then through the tissue on opposing sides of the puncture; and
   establishing tension in the suture to move the suture securing device toward another suture securing device to thereby close the puncture in the tissue.

2. The method of claim 1, wherein the needle guide is deployed distally from the guide member and advanced through the tissue by moving an activation handle relative to the guide member.

3. The method of claim 1, further comprising positioning a plug against the vessel wall.

4. The method of claim 1, wherein the suture securing device comprises a tapered body.

5. A method for closing a puncture in tissue, the method comprising:
   advancing a guide member into proximity with a puncture in tissue, a distal end of the guide member maintaining a position proximal to an anterior side of a vessel wall of the tissue;
   positioning a distal end of a needle guide toward the tissue to present an opening of the needle guide toward the tissue, the needle guide cooperating with an anchor;
   deploying the anchor in a distal direction, the anchor comprising a body with an anchor point for a suture and detachable needles, the detachable needles configured to selectively engage the needle guide, allowing the anchor to pierce the tissue and resist retraction through the tissue, the anchor point being at a location proximal an intermediate location of the anchor;
   wherein during deployment of the anchor, the detachable needles are moved distally beyond and radially outward from the distal end of the guide member to move the detachable needles through the tissue and on opposing sides of the puncture;
   withdrawing the needle guide in a proximal direction, thereby releasing the detachable needles from the needle guide; and
   moving the anchor toward a longitudinal axis of the guide member to close the puncture in the tissue.

6. The method of claim 5, further comprising actuating a handle relative to the guide member to deploy the needle guide distally.

7. The method of claim 5, further comprising advancing the anchor through the guide member to a deployment location within the tissue.

8. The method of claim 7, further comprising expanding the anchor to laterally extend beyond a deployment location of the anchor advanced through the tissue.

9. The method of claim 5, further comprising positioning a plug against the vessel wall.

10. The method of claim 5, wherein the anchor comprises a conical body.

11. A method for closing a puncture in tissue, the method comprising:
   advancing a distal end of a guide member in a distal direction to position openings near the distal end into proximity with a puncture in tissue, the distal end of the guide member maintaining a position proximal to an anterior side of the tissue;
   deploying a plurality of anchors, each of the plurality of anchors comprising a body with an anchor point for a suture and features that allow the anchors to pierce the tissue and resist retraction through the tissue, the anchor point being at a location proximal an intermediate location of the anchor;
   wherein during deployment of the plurality of anchors, the features that allow the plurality of anchors to pierce the tissue and resist retraction are first moved distally beyond and radially outward from the distal end of the guide member and then through the vessel wall on opposing sides of the puncture; and
   advancing a constricting member in a distal direction along a length of the suture to constrict the suture and move the plurality of anchors toward the longitudinal axis of the guide member to close the puncture in the tissue.

12. The method of claim 11, further comprising actuating a handle relative to the guide member to deploy the plurality of anchors.

13. The method of claim 11, further comprising advancing a locator through the guide member to a deployment location within the blood vessel.

14. The method of claim 13, further comprising expanding the locator to laterally extend beyond a deployment location of the anchors advanced through the tissue.

15. The method of claim 11, further comprising positioning a plug against the vessel wall.

16. The method of claim 11, wherein the anchor comprises a conical body.

\* \* \* \* \*

UNITED STATES PATENT AND TRADEMARK OFFICE
CERTIFICATE OF CORRECTION

PATENT NO.         : 11,439,378 B2
APPLICATION NO.    : 16/737604
DATED              : September 13, 2022
INVENTOR(S)        : Marc G. Gianotti and Aaron M. Fortson Page 1 of 1

It is certified that error appears in the above-identified patent and that said Letters Patent is hereby corrected as shown below:

On the Title Page

Item (73), Assignee:
Change "ABBOTT CARDIOVASCULAR SYSTEMS, INC." to --ABBOTT VASCULAR, INC.--

Signed and Sealed this
Twenty-ninth Day of July, 2025

Coke Morgan Stewart
*Acting Director of the United States Patent and Trademark Office*